United States Patent
Degenhardt et al.

(10) Patent No.: US 11,479,607 B2
(45) Date of Patent: Oct. 25, 2022

(54) ANTIGEN BINDING PROTEINS

(71) Applicant: GLAXOSMITHKLINE INTELLECTUAL PROPERTY DEVELOPMENT LIMITED, Brentford (GB)

(72) Inventors: Yan Y. Degenhardt, Collegeville, PA (US); Jun Guan, Collegeville, PA (US); Kenneth William Hance, Collegeville, PA (US); Peter Joseph Morley, Stevenage (GB)

(73) Assignee: GlaxoSmithKline Intellectual Property Development Limited, Brentford (GB)

( * ) Notice: Subject to any disclaimer, the term of this patent is extended or adjusted under 35 U.S.C. 154(b) by 0 days.

(21) Appl. No.: 17/530,849

(22) Filed: Nov. 19, 2021

(65) Prior Publication Data
US 2022/0089728 A1    Mar. 24, 2022

Related U.S. Application Data

(63) Continuation of application No. PCT/EP2020/076834, filed on Sep. 25, 2020.

(60) Provisional application No. 63/057,508, filed on Jul. 28, 2020, provisional application No. 62/906,876, filed on Sep. 27, 2019.

(51) Int. Cl.
*A61K 39/00* (2006.01)
*C07K 16/28* (2006.01)
*A61P 35/00* (2006.01)

(52) U.S. Cl.
CPC .......... *C07K 16/2803* (2013.01); *A61P 35/00* (2018.01); *A61K 2039/505* (2013.01); *C07K 2317/21* (2013.01); *C07K 2317/24* (2013.01); *C07K 2317/76* (2013.01); *C07K 2317/77* (2013.01); *C07K 2317/92* (2013.01)

(58) Field of Classification Search
CPC .............................................. A61K 2039/505
See application file for complete search history.

(56) References Cited

FOREIGN PATENT DOCUMENTS

| WO | WO 2008/073316 | 6/2008 |
|---|---|---|
| WO | WO2009/126688 A2 | 10/2009 |
| WO | WO2014/089169 A2 | 6/2014 |
| WO | WO2015/009856 A2 | 1/2015 |
| WO | WO2015/024060 A1 | 2/2015 |
| WO | WO2019/030377 A1 | 2/2019 |
| WO | WO2019/091449 A1 | 5/2019 |
| WO | WO2020/132034 A1 | 6/2020 |
| WO | WO2021/042019 A1 | 3/2021 |
| WO | WO2021058711 A2 * | 4/2021 |

OTHER PUBLICATIONS

Van den Beucken et al. (J. Mol. Biol. Jul. 13, 2001; 310 (3): 591-601).*
Ellis et al. (J. Immunol. Apr. 15, 1996; 156 (8): 2700-9).*
Holmes et al. (J. Immunol. Mar. 1, 1997; 158 (5): 2192-201).*
Blake, et al., "Molecular Pathways: Targeting CD96 and TIGIT for Cancer Immunotherapy", *Clinical Cancer Research*, 22(21):5183-5188 (2016).
PCT/EP2020/076834 International Search Report and Written Opinion, dated May 4, 2021.
Blake, et al.,"Suppression of Metastases Using New Lymphocyte Checkpoint Target for Cancer Immunotherapy", *Cancer Discovery*, 6(4): 446-459 (2016).
Brooks, J. et al. Perioperative, Spatiotemporally Coordinated Activation of T and NK Cells Prevents Recurrence of Pancreatic Cancer. Cancer Res 78, 475-488, doi:10.1158/0008-5472.CAN-17-2415 (2018).
Chan, et al., "Receptors that interact with nectin and nectin-like proteins in the immunosurveillance and immunotherapy of cancer," *Curr Opin Immunol.*, 24(2):246-51 (2012).
Chan, et al., "The receptors CD96 and CD226 oppose each other in the regulation of natural killer cell functions," *Nature Immunology*, 15(5): 431-438 (2014).
Chiang, et al., "CD96 functions as a co-stimulatory receptor to enhance CD8+ T cell activation and effector responses," *Eur. J. Immunol.*, 50: 891-902 (2020).
Cluxton, C. D. et al. Suppression of Natural Killer cell NKG2D and CD226 anti-tumour cascades by platelet cloaked cancer cells: Implications for the metastatic cascade. PLoS One 14, e0211538, doi:10.1371/journal.pone.0211538(2019).
Eriksson, et al., "Differential expression of CD96 surface molecule represents CD8+ T cells with dissimilar effector function during HIV-1 infection," *Plos One*, (2012).
Fuchs, "The role of NK cell recognition of nectin and nectin-like proteins in tumor immunosurveillance," *Seminars in Cancer Biology*, 16(5): 359-366 (2006).
Fuchs, et al., "Cutting Edge: CD96 (TACTILE) Promotes NK Cell-Target Cell Adhesion by Interacting with the Poliovirus receptor (CD155)," *J. Immunol.*, 172(7): 3994-3998 (2004).
Georgiev, et al., "Coming of Age: CD96 Emerges as Modulator of Immune Responses," *Frontiers in Immunology*, 9:1072 (2018).
Gong, J. et al. Establishment of an enzyme-linked immunosorbent assay system for determining soluble CD96 and its application in the measurement of sCD96 in patients with viral hepatitis B and hepatic cirrhosis. Clin Exp Immunol 155, 207-215, doi:10.1111/j.1365-2249.2008.03829.x (2009).
Gramatzki, et al., "Antibodies TC-12 ("unique") and TH-111 (CD96) characterize T-cell acute lymphoblastic leukemia and a subgroup of acute myeloid leukemia," Exp Hematol., 13:1209-14 (1998).
Harjunpaa, H. et al. Deficiency of host CD96 and PD-1 or TIGIT enhances tumor immunity without significantly compromising immune homeostasis. Oncoimmunology 7(7), e1445949, doi:10.1080/2162402X.2018.1445949 (2018).
Hosen, N. et al. CD96 is a leukemic stem cell-specific marker in human acute myeloid leukemia. Proc Natl Acad Sci U S A 104, 11008-11013, doi:10.1073/pnas.0704271104 (2007).

(Continued)

*Primary Examiner* — Stephen L Rawlings
(74) *Attorney, Agent, or Firm* — Romit Majumdar

(57) ABSTRACT

The present disclosure relates to compositions for treating CD96 mediated diseases, and related methods.

20 Claims, 36 Drawing Sheets

Specification includes a Sequence Listing.

(56) References Cited

OTHER PUBLICATIONS

Jin, et al., "Hitting the complexity of the TIGIT-CD96-CD112R-CD226 axis for next-generation cancer immunotherapy," *BMB Reports*, 54(1):2-11 (2021).

Kirchgessner, H. et al. The transmembrane adaptor protein TRIM regulates T cell receptor (TCR) expression and TCR-mediated signaling via an association with the TCR zeta chain. J Exp Med 193, 1269-1284, doi:10.1084/jem.193.11.1269 (2001).

Lepletier, A. et al. The immune checkpoint CD96 defines a distinct lymphocyte phenotype and is highly expressed on tumor-infiltrating T cells. Immunol Cell Biol 97, 152-164, doi: 10.1111/imcb.12205 (2019).

Maier, et al., "The adhesion receptor CD 155 determines the magnitude of humoral immune responses against orally ingested antigens," *Eur. J. Immunol.*, 37:2214-2225 (2007).

Martinet, et al., "Balancing natural killer cell activation through paired receptors," *Nature Reviews Immunology*, 15:243 (2015).

Meisen, J. E. et al. Human Bone Marrow-Resident Natural Killer Cells Have a Unique Transcriptional Profile and Resemble Resident Memory CD8(+) T Cells. Front Immunol 9, 1829, doi:10.3389/fimmu.2018.01829 (2018).

Meyer, et al., "CD96 interaction with CD 155 via its first Ig-like domain is modulated by alternative splicing or mutations in distal Ig-like domains," *Journal of Biol. Chem.*, 284(4):2235-2244 (2009).

Mittal, et al., "CD96 is an Immune Checkpoint that Regulates CD8+ T-cell Antitumor function," *Cancer Immunology Research*, (2019).

Nodehi, et al., "Enhanced ADCC activity of affinity matured and Fc-engineered mini-antibodies directed against the AML stem cell antigen CD96," *PLoS One*, 7(8) e42426 (2012).

Roman Aguilera, A. et al. CD96 targeted antibodies need not block CD96-CD155 interactions to promote NK cell anti-metastatic activity. Oncoimmunology 7, e1424677, doi: 10.1080/2162402X.2018.1424677 (2018).

Rudd, C. E. & Schneider, H. Unifying concepts in CD28, Icos and CTLA4 co-receptor signalling. Nat Rev Immunol 3, 544-556, doi:10.1038/nri1131 (2003).

Seth, et al., "The murine pan T cell marker CD96 is an adhesion receptor for CD 155 and nectin-1," *Biochem Biophys Res Comm*, 364, 959-965 (2007).

Stanietsky, "Paired NK cell receptors controlling NK cytotoxicity," *FEBS Letters*. (2010).

Sun, H. et al. Accumulation of Tumor-Infiltrating CD49a(+) NK Cells Correlates with Poor Prognosis for Human Hepatocellular Carcinoma. *Cancer Immunol Res* 7, 1535-1546, doi:10.1158/2326-6066.CIR-18-0757 (2019).

Sun, H. et al. Human CD96 Correlates to Natural Killer Cell Exhaustion and Predicts the Prognosis of Human Hepatocellular Carcinoma. *Hepatology* 70, 168-183, doi:10.1002/hep.30347 (2019).

Wang, et al., "Identification and molecular cloning of tactile. A novel human T cell activation antigen that is a member of the Ig gene superfamily," *J. Immunology*, 148(8), 2600-2608 (1992).

Wu, M., Mei, F., Liu, W. & Jiang, J. Comprehensive characterization of tumor infiltrating natural killer cells and clinical significance in hepatocellular carcinoma based on gene expression profiles. Biomed Pharmacother 121, 109637, doi:10.1016/j.biopha.2019.109637 (2020).

Zhang, W. et al. Expressions of CD96 and CD123 in Bone Marrow Cells of Patients with Myelodysplastic Syndromes. Clin Lab 61, 1429-1434, doi:10.7754/clin.lab.2015.141240 (2015).

\* cited by examiner

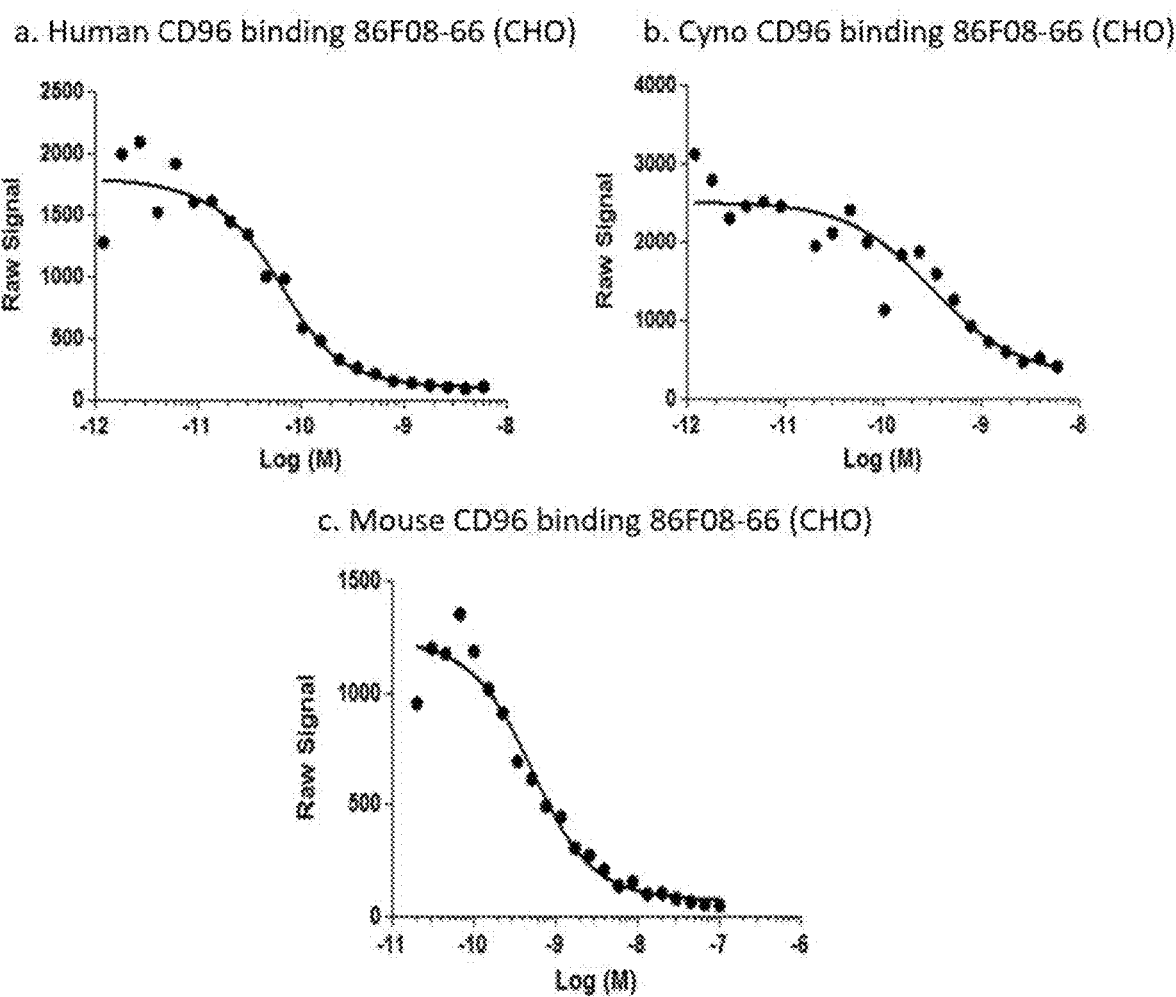

FIG. 6
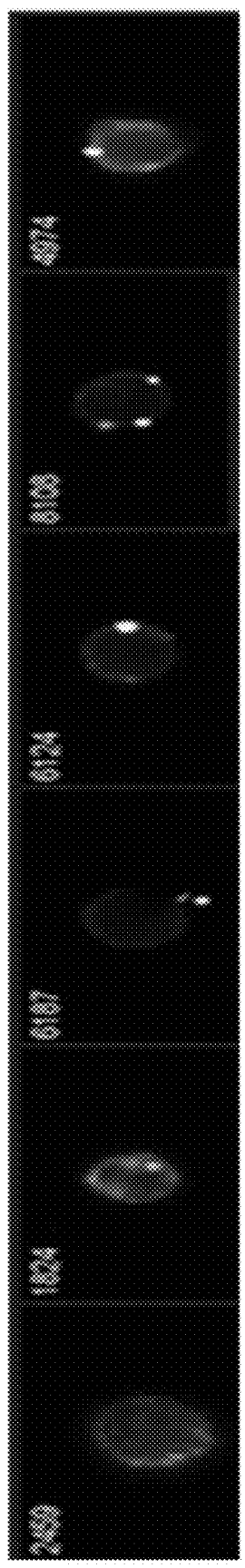
86F08-66 (CHO) staining on CD8 T cells at 0 hours
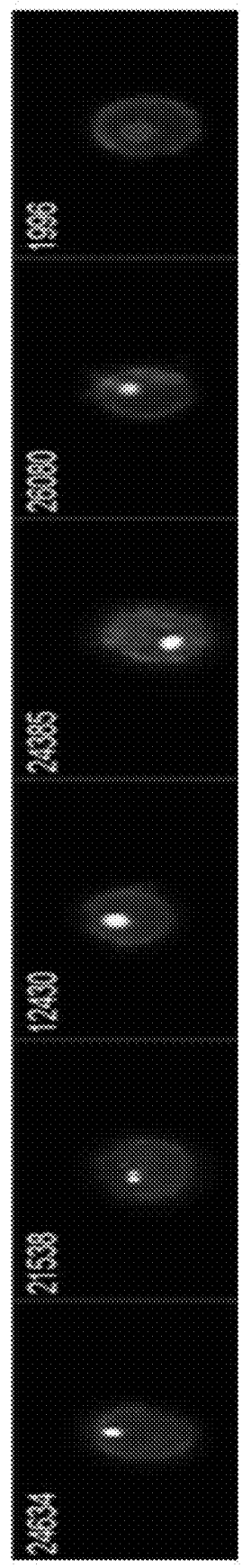
86F08-66 (CHO) staining on CD8 T cells at 45 hours

FIG. 12

|  | Exp. 1 EC50 | | Exp. 2 EC50 | |
| --- | --- | --- | --- | --- |
|  | µg/ml | pM | µg/ml | pM |
| 42Y073-86F08-66 (CHO) | 0.0027 | 18 pM | 0.0033 | 22 pM |
| 42Y073-86F08-66 (HEK) | 0.0013 | 9 pM | 0.0015 | 10 pM |
| Tecentriq | 0.0073 | 49 pM | 0.0210 | 140 pM |

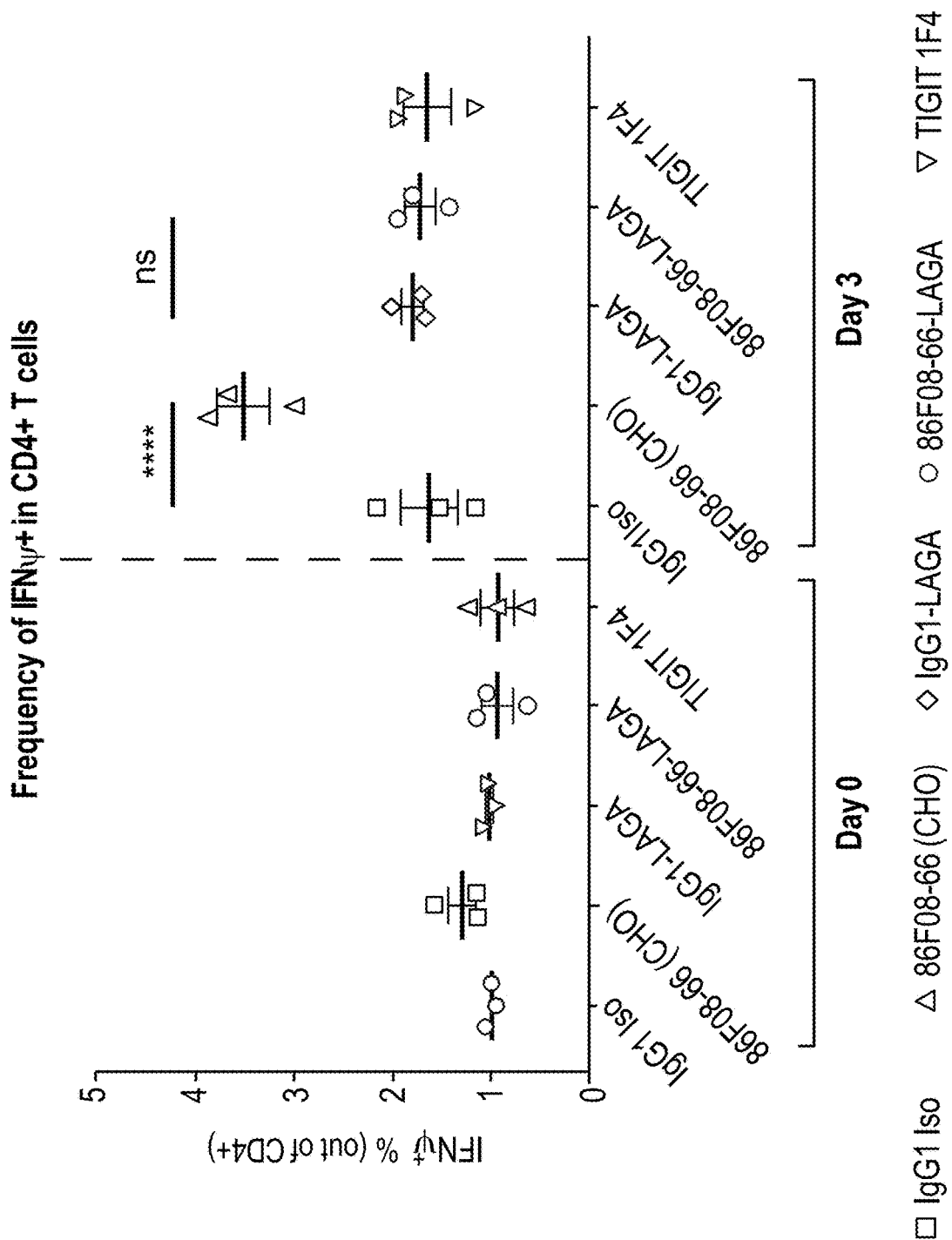

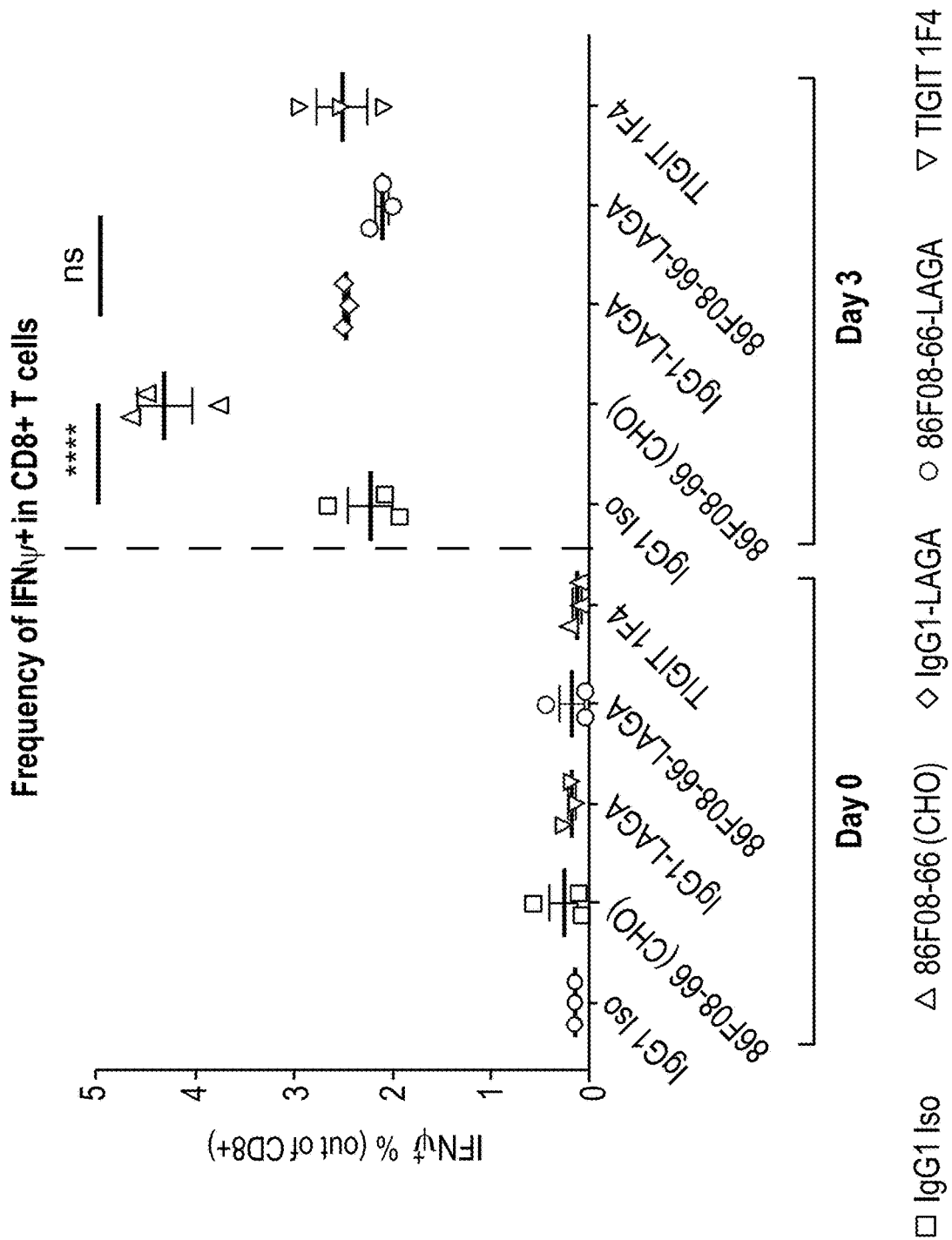

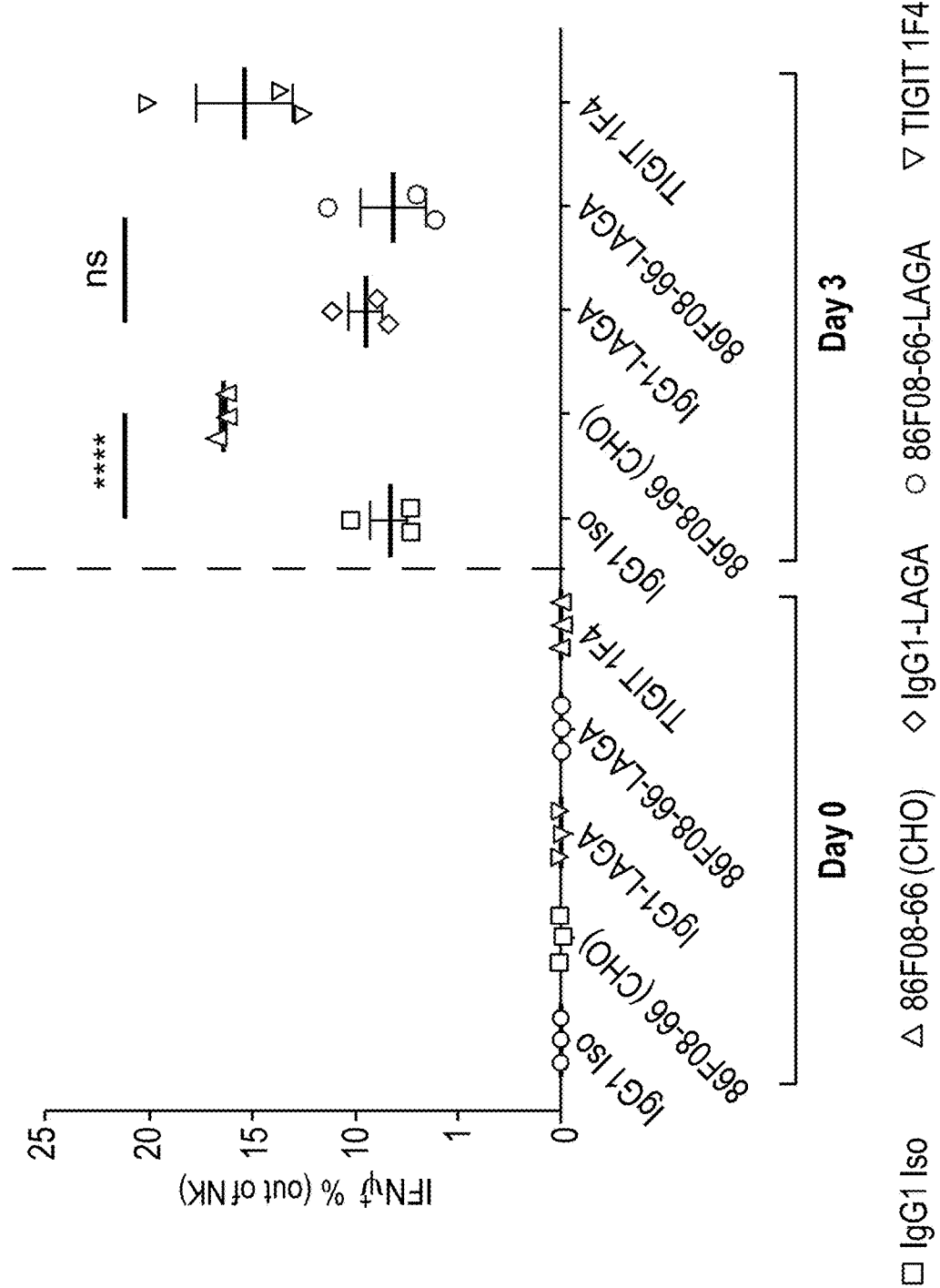

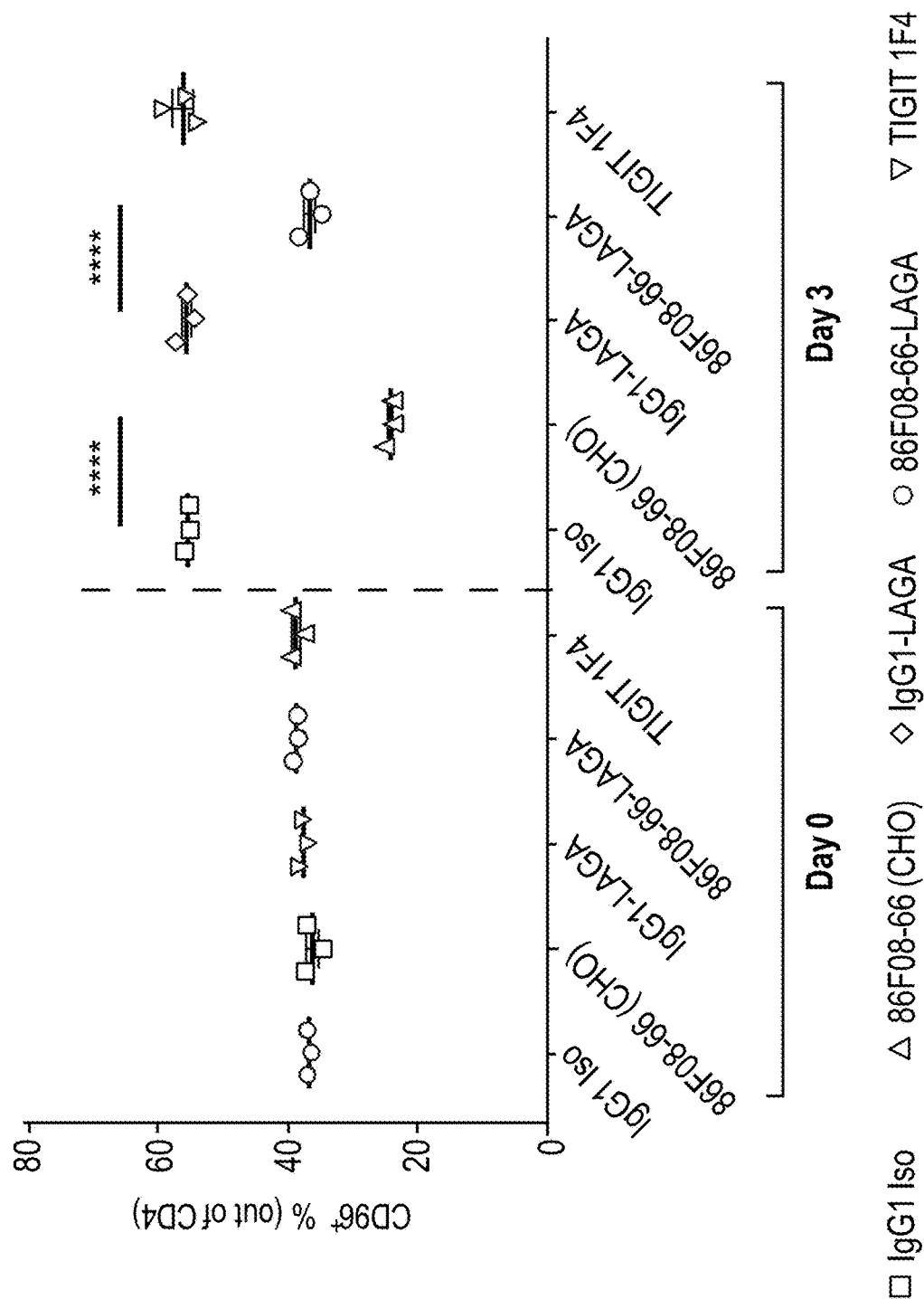

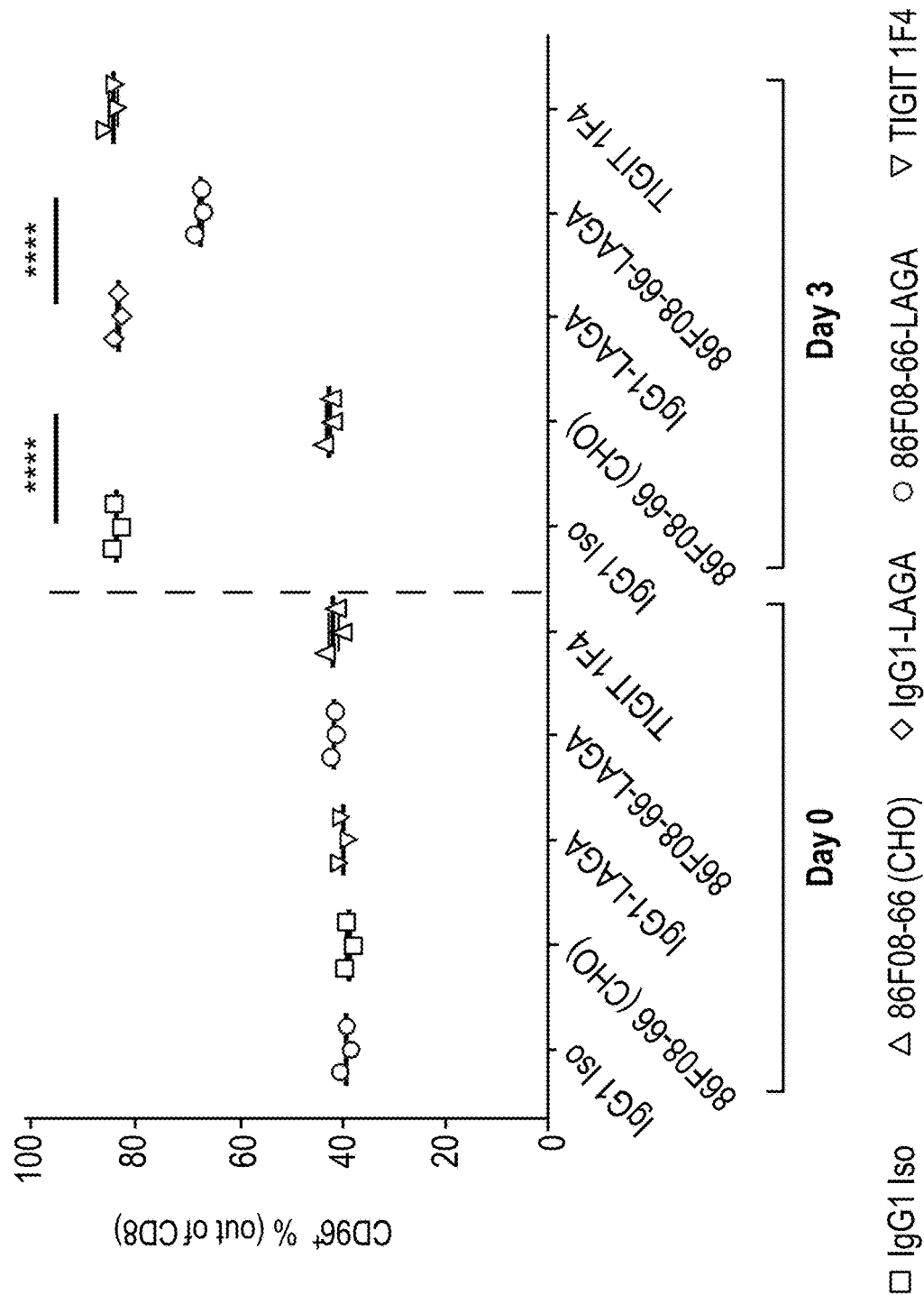

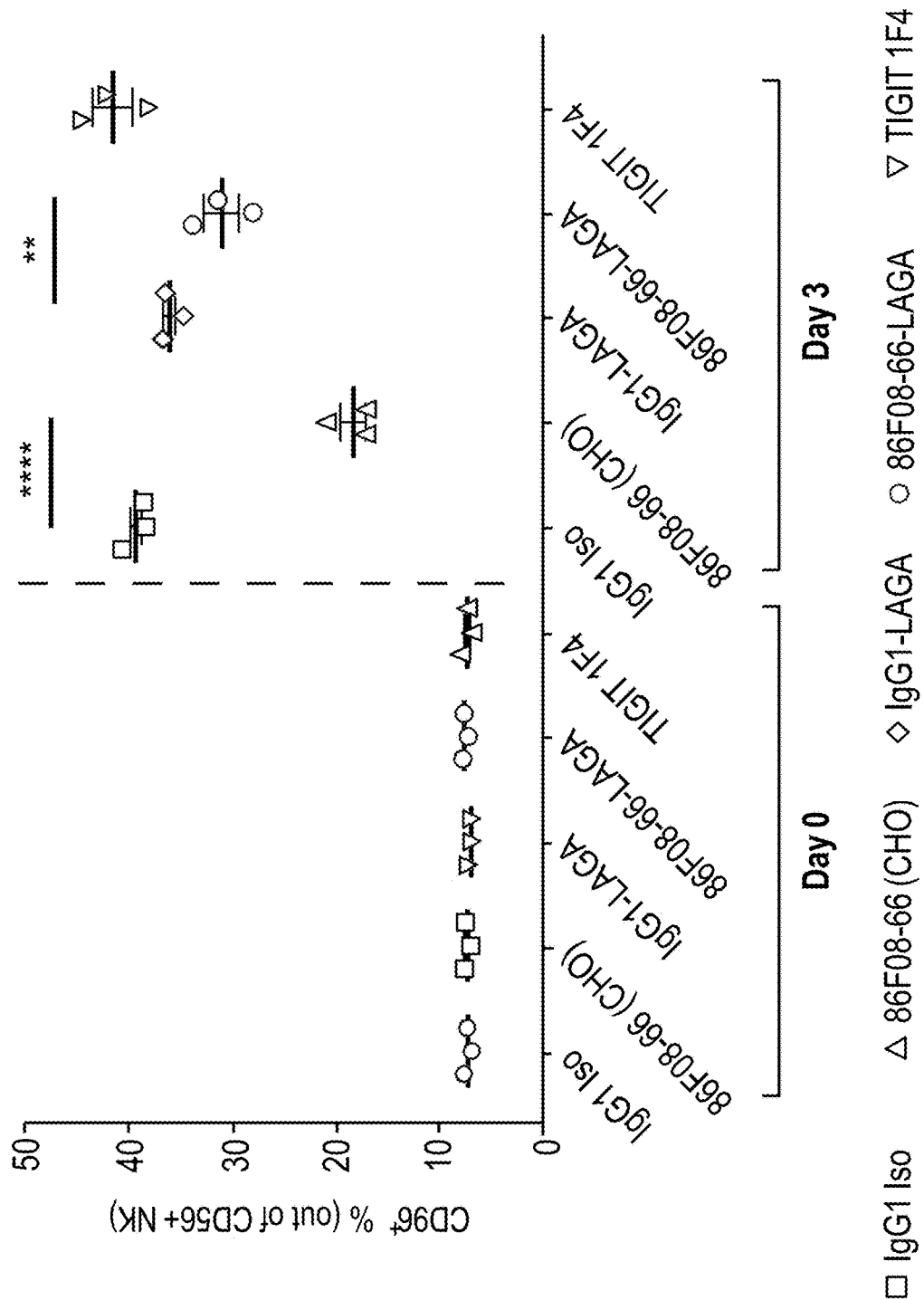

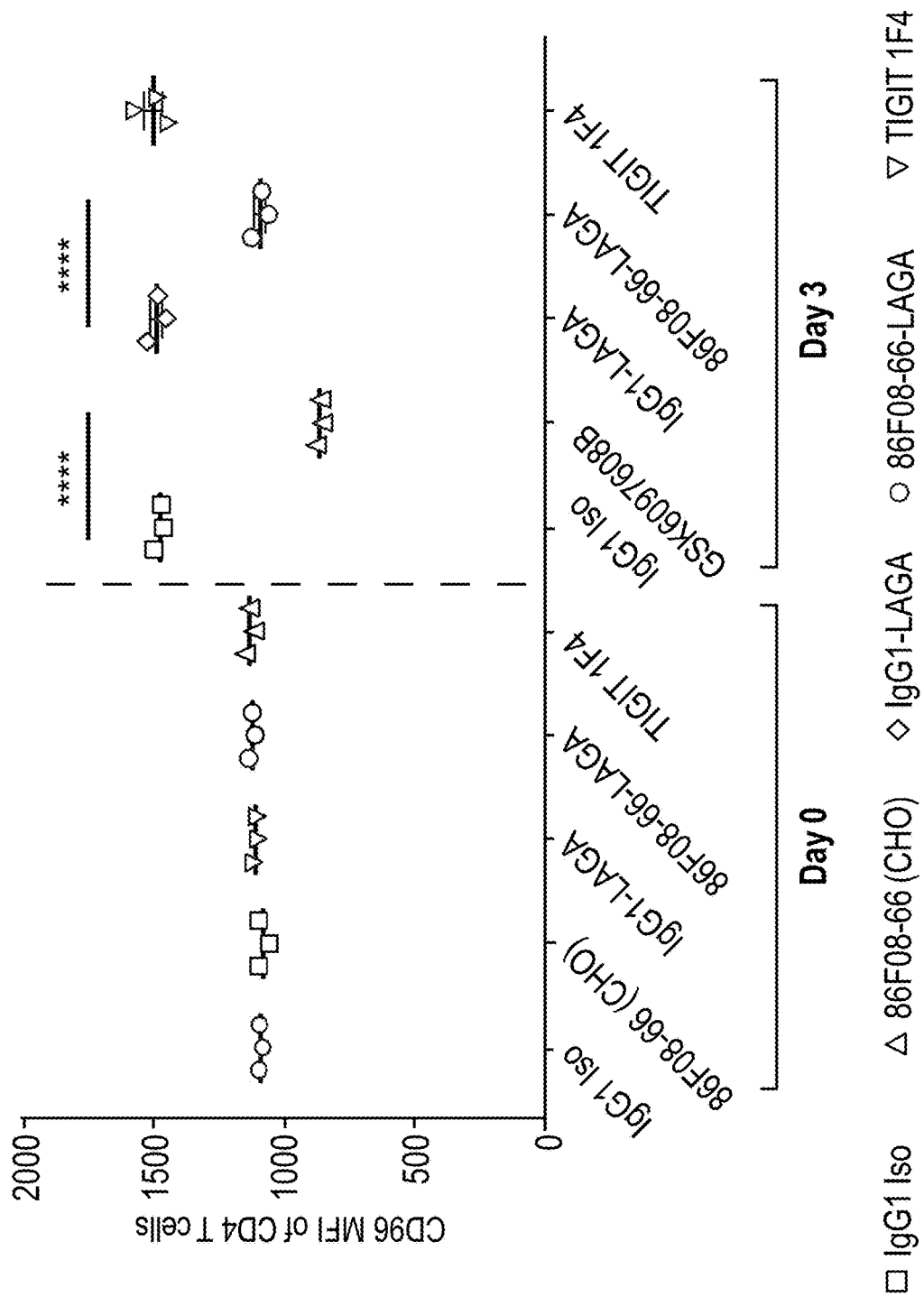

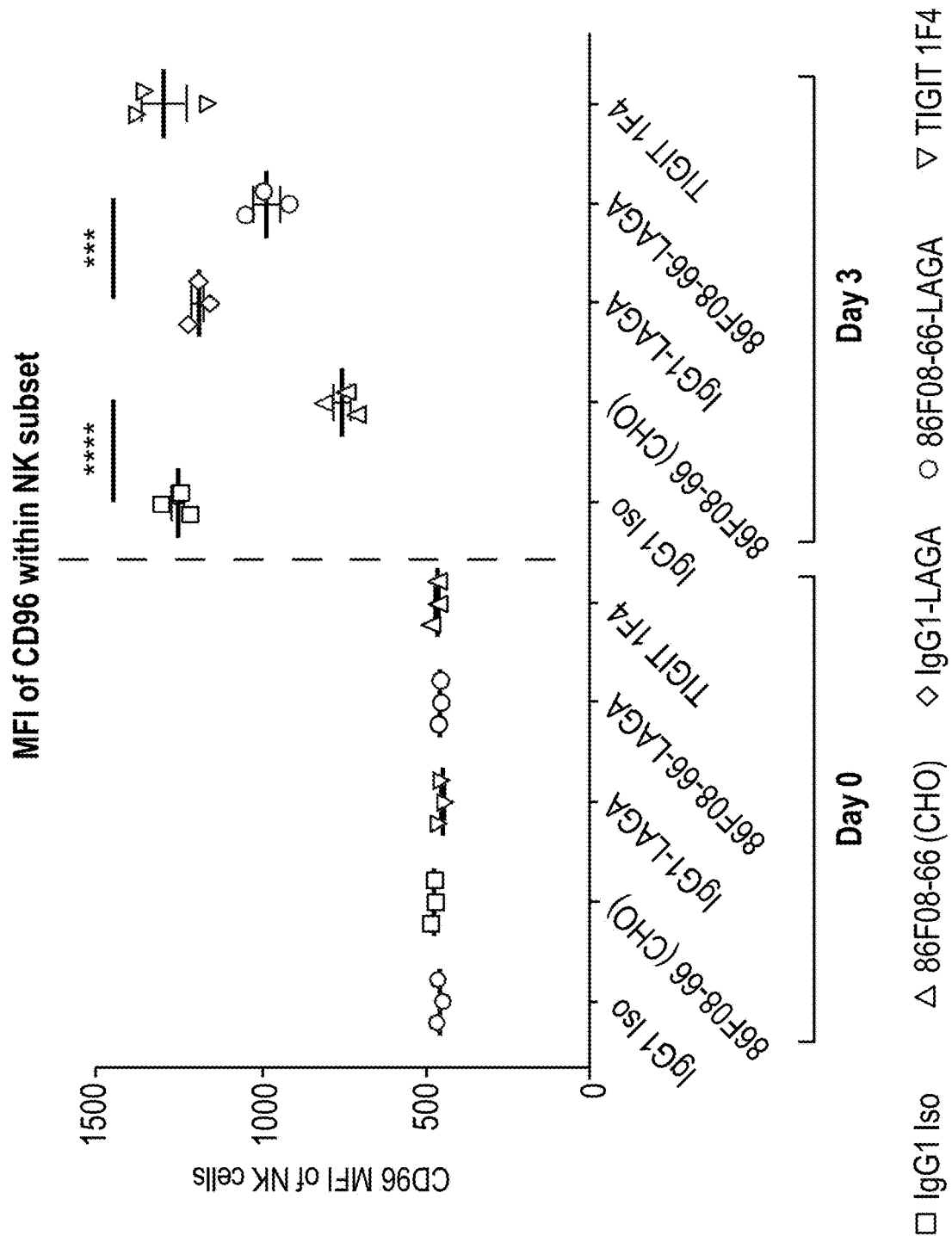

FIG. 25
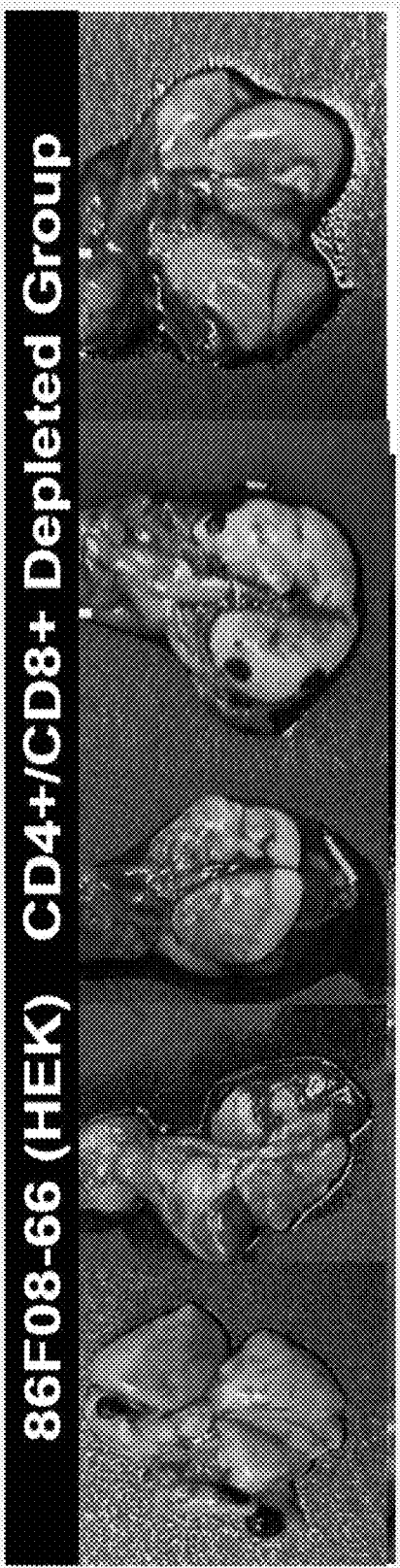

SEQUENCE LISTING

```
<160> NUMBER OF SEQ ID NOS: 180

<210> SEQ ID NO 1
<211> LENGTH: 106
<212> TYPE: PRT
<213> ORGANISM: Artificial
<220> FEATURE:
<223> OTHER INFORMATION: 42Y073-86F08-1 variable light chain amino acid
      sequence

<400> SEQUENCE: 1

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Leu His Thr Ile Thr
                85                  90                  95

Phe Gly Gly Gly Thr Lys Val Glu Ile Lys
            100                 105

<210> SEQ ID NO 2
<211> LENGTH: 122
<212> TYPE: PRT
<213> ORGANISM: Artificial
<220> FEATURE:
<223> OTHER INFORMATION: 42Y073-86F08-1 variable heavy chain amino acid
      sequence

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Ser Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Gly Tyr Tyr Gly Asp Lys Asp Pro Met Asp Val Trp
            100                 105                 110
```

Gly Gln Gly Thr Thr Val Thr Val Ser Ser
        115                 120

```
<210> SEQ ID NO 3
<211> LENGTH: 318
<212> TYPE: DNA
<213> ORGANISM: Artificial
<220> FEATURE:
<223> OTHER INFORMATION: 42Y073-86F08-1 variable light chain nucleic
      acid sequence

<400> SEQUENCE: 3
gacatccagc tgacccagag ccctagcagc ctgagcgcca gcgtgggaga cagggtgacc      60
atcacctgca gggccagcca gtccatcagc agctacctga actggtacca gcagaagccc     120
ggcaaggccc ccaagctgct gatctacgcc gcaagctcac tgcagagcgg cgtgccctct     180
aggtttagcg gcagcggcag cggcaccgac ttcaccctga ccatcagcag cctccagccc     240
gaggacttcg ccacctacta ctgccagcag gtgctgcaca ccatcacttt cggcggcggc     300
accaaggtgg agattaag                                                   318

<210> SEQ ID NO 4
<211> LENGTH: 366
<212> TYPE: DNA
<213> ORGANISM: Artificial
<220> FEATURE:
<223> OTHER INFORMATION: 42Y073-86F08-1 variable heavy chain nucleic
      acid sequence

<400> SEQUENCE: 4
caggtgcagc tggtgcagag cggcgccgag gtgaaaaagc ccggcagcag cgtgaaggtg      60
agctgcaagg cctccggcgg gaccttcagc agctacgcca tcagctgggt gaggcaggct     120
cccggacagg gcctggagtg gatgggcggc atcatcccca ttttcggcac cgccagctac     180
gcccagaagt tccagggaag ggtcaccatc accgccacg agagcaccag caccgcctac     240
atggaactca gcagcctgag gagcgaggac accgccgtgt actattgcgc caggggcgcc     300
ggctactacg cgacaaggac ccccatggac gtgtggggcc agggcaccac cgtgactgtg     360
agcagc                                                               366

<210> SEQ ID NO 5
<211> LENGTH: 107
<212> TYPE: PRT
<213> ORGANISM: Artificial
<220> FEATURE:
<223> OTHER INFORMATION: 42Y073-86F04-3 variable light chain amino acid
      sequence

<400> SEQUENCE: 5
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Tyr Phe Ser Pro Pro
                85                  90                  95

```
Thr Phe Gly Gly Gly Thr Lys Val Glu Ile Lys
            100                 105

<210> SEQ ID NO 6
<211> LENGTH: 118
<212> TYPE: PRT
<213> ORGANISM: Artificial
<220> FEATURE:
<223> OTHER INFORMATION: 42Y073-86F04-3 variable heavy chain amino acid
      sequence

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Tyr Asn
            20                  25                  30

Ala Ile Ser Trp Val Arg Gln Ala Pro Gly Gln Gly Leu Glu Trp Met
        35                  40                  45

Gly Gly Ile Ile Pro Ile Met Gly Thr Ala Arg Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Gly Glu Ser Gly Met Asp Val Trp Gly Gln Gly Thr
            100                 105                 110

Thr Val Thr Val Ser Ser
        115

<210> SEQ ID NO 7
<211> LENGTH: 321
<212> TYPE: DNA
<213> ORGANISM: Artificial
<220> FEATURE:
<223> OTHER INFORMATION: 42Y073-86F04-3 variable light chain nucleic
      acid sequence

<400> SEQUENCE: 7
gacatccaga tgacccagag ccctagcagc ctgagcgcca gcgtgggaga cagggtgacc      60
atcacctgca gggccagcca gtccatcagc agctacctga actggtacca gcagaagccc     120
ggcaaggccc ccaagctgct gatctacgcc gcaagctcac tgcagagcgg cgtgccctct     180
aggtttagcg gcagcggcag cggcaccgac ttcaccctga ccatcagcag cctccagccc     240
gaggacttcg ccacctacta ctgccagcag ccctacttca gccccccac tttcggcggc      300 ggcaccaagg tggagattaa g                                               321

<210> SEQ ID NO 8
<211> LENGTH: 354
<212> TYPE: DNA
<213> ORGANISM: Artificial
<220> FEATURE:
<223> OTHER INFORMATION: 42Y073-86F04-3 variable heavy chain nucleic
      acid sequence

<400> SEQUENCE: 8
caggtgcagc tggtgcagag cggcgccgag gtgaaaaagc ccggcagcag cgtgaaggtg      60
agctgcaagg cctccggcgg gaccttcagc tacaacgcca tcagctgggt gaggcaggct     120
cccggacagg gcctggagtg gatgggcggc atcatcccca ttatgggcac cgccaggtac     180
```

```
gcccagaagt tccagggaag ggtcaccatc accgccgacg agagcaccag caccgcctac    240
atggaactca gcagcctgag gagcgaggac accgccgtgt actattgcgc caggctgctg    300
ggcgagagcg gcatggacgt gtggggccag ggcaccaccg tgactgtgag cagc          354
```

<210> SEQ ID NO 9
<211> LENGTH: 107
<212> TYPE: PRT
<213> ORGANISM: Artificial
<220> FEATURE:
<223> OTHER INFORMATION: 42Y073-86F04-4 variable light chain amino acid
      sequence

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Tyr Phe Ser Pro Pro
                85                  90                  95

Thr Phe Gly Gly Gly Thr Lys Val Glu Ile Lys
            100                 105
```

<210> SEQ ID NO 10
<211> LENGTH: 118
<212> TYPE: PRT
<213> ORGANISM: Artificial
<220> FEATURE:
<223> OTHER INFORMATION: 42Y073-86F04-4 variable heavy chain amino acid
      sequence

<400> SEQUENCE: 10

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Glu Ser Glu
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Arg Ala Arg Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Gly Glu Ser Gly Met Asp Val Trp Gly Gln Gly Thr
            100                 105                 110

Thr Val Thr Val Ser Ser
        115
```

<210> SEQ ID NO 11
<211> LENGTH: 321
<212> TYPE: DNA
<213> ORGANISM: Artificial
<220> FEATURE:

<223> OTHER INFORMATION: 42Y073-86F04-4 variable light chain nucleic
       acid sequence

<400> SEQUENCE: 11
gacatccaga tgacccagag ccctagcagc ctgagcgcca gcgtgggaga cagggtgacc    60
atcacctgca gggccagcca gtccatcagc agctacctga actggtacca gcagaagccc   120
ggcaaggccc ccaagctgct gatctacgcc gcaagctcac tgcagagcgg cgtgccctct   180
aggtttagcg gcagcggcag cggcaccgac ttcaccctga ccatcagcag cctccagccc   240
gaggacttcg ccacctacta ctgccagcag ccctacttca gcccccccac tttcggcggc   300
ggcaccaagg tggagattaa g                                              321

<210> SEQ ID NO 12
<211> LENGTH: 354
<212> TYPE: DNA
<213> ORGANISM: Artificial
<220> FEATURE:
<223> OTHER INFORMATION: 42Y073-86F04-4 variable heavy chain nucleic
       acid sequence

<400> SEQUENCE: 12
caggtgcagc tggtgcagag cggcgccgag gtgaaaaagc ccggcagcag cgtgaaggtg    60
agctgcaagg cctccggcgg gaccttcgag agcgaggcca tcagctgggt gaggcaggct   120 cccgacagg gcctggagtg gatgggcggc atcatcccca ttttcggcag ggccaggtac   180
gcccagaagt tccagggaag ggtcaccatc accgccgacg agagcaccag caccgcctac   240
atggaactca gcagcctgag gagcgaggac accgccgtgt actattgcgc caggctgctg   300
ggcgagagcg gcatggacgt gtggggccag ggcaccaccg tgactgtgag cagc          354

<210> SEQ ID NO 13
<211> LENGTH: 107
<212> TYPE: PRT
<213> ORGANISM: Artificial
<220> FEATURE:
<223> OTHER INFORMATION: 42Y073-86F04-5 variable light chain amino acid
       sequence

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Tyr Phe Ser Pro Pro
                85                  90                  95

Thr Phe Gly Gly Gly Thr Lys Val Glu Ile Lys
            100                 105

<210> SEQ ID NO 14
<211> LENGTH: 118
<212> TYPE: PRT
<213> ORGANISM: Artificial
<220> FEATURE:
<223> OTHER INFORMATION: 42Y073-86F04-5 variable heavy chain amino acid sequence

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Arg Gly Lys Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Gly Glu Ser Gly Met Asp Val Trp Gly Gln Gly Thr
            100                 105                 110

Thr Val Thr Val Ser Ser
        115

<210> SEQ ID NO 15
<211> LENGTH: 321
<212> TYPE: DNA
<213> ORGANISM: Artificial
<220> FEATURE:
<223> OTHER INFORMATION: 42Y073-86F04-5 variable light chain nucleic
      acid sequence

<400> SEQUENCE: 15
gacatccaga tgacccagag ccctagcagc ctgagcgcca gcgtgggaga cagggtgacc      60
atcacctgca gggccagcca gtccatcagc agctacctga actggtacca gcagaagccc    120
ggcaaggccc ccaagctgct gatctacgcc gcaagctcac tgcagagcgg cgtgccctct    180
aggtttagcg gcagcggcag cggcaccgac ttcaccctga ccatcagcag cctccagccc    240
gaggacttcg ccacctacta ctgccagcag ccctacttca gcccccccac tttcggcggc    300
ggcaccaagg tggagattaa g                                              321

<210> SEQ ID NO 16
<211> LENGTH: 354
<212> TYPE: DNA
<213> ORGANISM: Artificial
<220> FEATURE:
<223> OTHER INFORMATION: 42Y073-86F04-5 variable heavy chain nucleic
      acid sequence

<400> SEQUENCE: 16
caggtgcagc tggtgcagag cggcgccgag gtgaaaaagc ccggcagcag cgtgaaggtg      60
agctgcaagg cctccggcgg gaccttcagc agccacgcca tcagctgggt gaggcaggct    120
cccggacagg gcctggagtg gatgggcggc atcatcccca ttttcggcag ggcaagtac     180
gcccagaagt tccagggaag ggtcaccatc accgccgacg agagcaccag caccgcctac    240
atggaactca gcagcctgag gagcgaggac accgccgtgt actattgcgc caggctgctg    300
ggcgagagcg gcatggacgt gtggggccag ggcaccaccg tgactgtgag cagc          354

<210> SEQ ID NO 17
<211> LENGTH: 107
<212> TYPE: PRT
<213> ORGANISM: Artificial

<220> FEATURE:
<223> OTHER INFORMATION: 42Y073-86F04-6 variable light chain amino acid
      sequence

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Tyr Phe Ser Pro Pro
                85                  90                  95

Thr Phe Gly Gly Gly Thr Lys Val Glu Ile Lys
            100                 105

<210> SEQ ID NO 18
<211> LENGTH: 118
<212> TYPE: PRT
<213> ORGANISM: Artificial
<220> FEATURE:
<223> OTHER INFORMATION: 42Y073-86F04-6 variable heavy chain amino acid
      sequence

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Gly His
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Arg Ala Arg Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Gly Glu Ser Gly Met Asp Val Trp Gly Gln Gly Thr
            100                 105                 110

Thr Val Thr Val Ser Ser
        115

<210> SEQ ID NO 19
<211> LENGTH: 321
<212> TYPE: DNA
<213> ORGANISM: Artificial
<220> FEATURE:
<223> OTHER INFORMATION: 42Y073-86F04-6 variable light chain nucleic
      acid sequence

<400> SEQUENCE: 19
gacatccaga tgacccagag ccctagcagc ctgagcgcca gcgtgggaga cagggtgacc        60
atcacctgca gggccagcca gtccatcagc agctacctga actggtacca gcagaagccc       120
ggcaaggccc ccaagctgct gatctacgcc gcaagctcac tgcagagcgg cgtgccctct       180

```
aggtttagcg gcagcggcag cggcaccgac ttcaccctga ccatcagcag cctccagccc    240
gaggacttcg ccacctacta ctgccagcag ccctacttca gcccccccac tttcggcggc    300
ggcaccaagg tggagattaa g                                              321
```

<210> SEQ ID NO 20
<211> LENGTH: 354
<212> TYPE: DNA
<213> ORGANISM: Artificial
<220> FEATURE:
<223> OTHER INFORMATION: 42Y073-86F04-6 variable heavy chain nucleic
      acid sequence <400> SEQUENCE: 20

```
caggtgcagc tggtgcagag cggcgccgag gtgaaaaagc ccggcagcag cgtgaaggtg    60
agctgcaagg cctccggcgg gaccttcagc ggccacgcca tcagctgggt gaggcaggct   120
cccggacagg gcctggagtg gatgggcggc atcatcccca ttttcggcag ggccaggtac   180
gcccagaagt tccagggaag ggtcaccatc accgccgacg agagcaccag caccgcctac   240
atggaactca gcagcctgag gagcgaggac accgccgtgt actattgcgc caggctgctg   300
ggcgagagcg gcatggacgt gtggggccag ggcaccaccg tgactgtgag cagc         354
```

<210> SEQ ID NO 21
<211> LENGTH: 107
<212> TYPE: PRT
<213> ORGANISM: Artificial
<220> FEATURE:
<223> OTHER INFORMATION: 42Y073-86F04-18 variable light chain amino acid
      sequence <400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Tyr Phe Ser Pro Pro
                85                  90                  95

Thr Phe Gly Gly Gly Thr Lys Val Glu Ile Lys
            100                 105
```

<210> SEQ ID NO 22
<211> LENGTH: 118
<212> TYPE: PRT
<213> ORGANISM: Artificial
<220> FEATURE:
<223> OTHER INFORMATION: 42Y073-86F04-18 variable heavy chain amino acid
      sequence <400> SEQUENCE: 22

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Arg
            20                  25                  30

Ala Ile Ser Trp Val Arg Gln Ala Pro Gly Gln Gly Leu Glu Trp Met
```

```
                    35                  40                  45
Gly Gly Ile Ile Pro Ile Met Gly Thr Ala Arg Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                     85                  90                  95

Ala Arg Leu Leu Gly Glu Ser Gly Met Asp Val Trp Gly Gln Gly Thr
                100                 105                 110

Thr Val Thr Val Ser Ser
            115

<210> SEQ ID NO 23
<211> LENGTH: 321
<212> TYPE: DNA
<213> ORGANISM: Artificial
<220> FEATURE:
<223> OTHER INFORMATION: 42Y073-86F04-18 variable light chain nucleic
      acid sequence

<400> SEQUENCE: 23
gacatccaga tgacccagag ccctagcagc ctgagcgcca gcgtgggaga cagggtgacc      60
atcacctgca gggccagcca gtccatcagc agctacctga actggtacca gcagaagccc    120
ggcaaggccc ccaagctgct gatctacgcc gcaagctcac tgcagagcgg cgtgccctct    180
aggtttagcg gcagcggcag cggcaccgac ttcaccctga ccatcagcag cctccagccc    240
gaggacttcg ccacctacta ctgccagcag ccctacttca gccccccac tttcggcggc    300 ggcaccaagg tggagattaa g                                              321

<210> SEQ ID NO 24
<211> LENGTH: 354
<212> TYPE: DNA
<213> ORGANISM: Artificial
<220> FEATURE:
<223> OTHER INFORMATION: 42Y073-86F04-18 variable heavy chain nucleic
      acid sequence

<400> SEQUENCE: 24
caggtgcagc tggtgcagag cggcgccgag gtgaaaaagc ccggcagcag cgtgaaggtg      60
agctgcaagg cctccggcgg gaccttcagc agcagggcca tcagctgggt gaggcaggct    120
cccggacagg gcctggagtg gatgggcggc atcatcccca ttatgggcac cgccaggtac    180
gcccagaagt tccagggaag ggtcaccatc accgccgacg agagcaccag caccgcctac    240
atggaactca gcagcctgag gagcgaggac accgccgtgt actattgcgc caggctgctg    300
ggcgagagcg gcatggacgt gtggggccag ggcaccaccg tgactgtgag cagc           354

<210> SEQ ID NO 25
<211> LENGTH: 107
<212> TYPE: PRT
<213> ORGANISM: Artificial
<220> FEATURE:
<223> OTHER INFORMATION: 42Y073-86F04-33 variable light chain amino acid
      sequence

<400> SEQUENCE: 25

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30
```

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Tyr Phe Ser Pro Pro
                85                  90                  95

Thr Phe Gly Gly Gly Thr Lys Val Glu Ile Lys
            100                 105

<210> SEQ ID NO 26
<211> LENGTH: 118
<212> TYPE: PRT
<213> ORGANISM: Artificial
<220> FEATURE:
<223> OTHER INFORMATION: 42Y073-86F04-33 variable heavy chain amino acid
      sequence

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Leu Pro Ile Phe Gly Arg Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Gly Glu Ser Gly Met Asp Val Trp Gly Gln Gly Thr
            100                 105                 110

Thr Val Thr Val Ser Ser
        115

<210> SEQ ID NO 27
<211> LENGTH: 321
<212> TYPE: DNA
<213> ORGANISM: Artificial
<220> FEATURE:
<223> OTHER INFORMATION: 42Y073-86F04-33 variable light chain nucleic
      acid sequence

<400> SEQUENCE: 27
gacatccaga tgacccagag ccctagcagc ctgagcgcca gcgtgggaga cagggtgacc      60
atcacctgca gggccagcca gtccatcagc agctacctga actggtacca gcagaagccc    120
ggcaaggccc ccaagctgct gatctacgcc gcaagctcac tgcagagcgg cgtgccctct    180
aggtttagcg gcagcggcag cggcaccgac ttcaccctga ccatcagcag cctccagccc    240
gaggacttcg ccacctacta ctgccagcag ccctacttca gcccccccac tttcggcggc    300
ggcaccaagg tggagattaa g                                              321

<210> SEQ ID NO 28
<211> LENGTH: 354
<212> TYPE: DNA
<213> ORGANISM: Artificial

```
<220> FEATURE:
<223> OTHER INFORMATION: 42Y073-86F04-33 variable heavy chain nucleic
      acid sequence

<400> SEQUENCE: 28
caggtgcagc tggtgcagag cggcgccgag gtgaaaaagc ccggcagcag cgtgaaggtg      60
agctgcaagg cctccggcgg gaccttcagc agctacgcca tcagctgggt gaggcaggct     120
cccggacagg gcctggagtg gatgggcggc atcctgccca ttttcggcag ggccaactac     180
gcccagaagt tccagggaag ggtcaccatc accgccgacg agagcaccag caccgcctac     240
atggaactca gcagcctgag gagcgaggac accgccgtgt actattgcgc caggctgctg     300
ggcgagagcg gcatggacgt gtggggccag ggcaccaccg tgactgtgag cagc           354

<210> SEQ ID NO 29
<211> LENGTH: 107
<212> TYPE: PRT
<213> ORGANISM: Artificial
<220> FEATURE:
<223> OTHER INFORMATION: 42Y073-86F04-88 variable light chain amino acid
      sequence

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Tyr Phe Ser Pro Pro
                85                  90                  95

Thr Phe Gly Gly Gly Thr Lys Val Glu Ile Lys
            100                 105

<210> SEQ ID NO 30
<211> LENGTH: 118
<212> TYPE: PRT
<213> ORGANISM: Artificial
<220> FEATURE:
<223> OTHER INFORMATION: 42Y073-86F04-88 variable heavy chain amino acid
      sequence

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Ser
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Arg Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Leu Leu Gly Glu Ser Gly Met Asp Val Trp Gly Gln Gly Thr
            100                 105                 110

Thr Val Thr Val Ser Ser
        115

<210> SEQ ID NO 31
<211> LENGTH: 321
<212> TYPE: DNA
<213> ORGANISM: Artificial
<220> FEATURE:
<223> OTHER INFORMATION: 42Y073-86F04-88 variable light chain nucleic
      acid sequence

<400> SEQUENCE: 31
gacatccaga tgacccagag ccctagcagc ctgagcgcca gcgtgggaga cagggtgacc    60
atcacctgca gggccagcca gtccatcagc agctacctga actggtacca gcagaagccc   120
ggcaaggccc ccaagctgct gatctacgcc gcaagctcac tgcagagcgg cgtgccctct   180
aggtttagcg gcagcggcag cggcaccgac ttcaccctga ccatcagcag cctccagccc   240
gaggacttcg ccacctacta ctgccagcag ccctacttca gccccccac tttcggcggc    300 ggcaccaagg tggagattaa g                                             321

<210> SEQ ID NO 32
<211> LENGTH: 354
<212> TYPE: DNA
<213> ORGANISM: Artificial
<220> FEATURE:
<223> OTHER INFORMATION: 42Y073-86F04-88 variable heavy chain nucleic
      acid sequence

<400> SEQUENCE: 32
caggtgcagc tggtgcagag cggcgccgag gtgaaaaagc ccggcagcag cgtgaaggtg    60
agctgcaagg cctccggcgg gaccttcagc agcagcgcca tcagctgggt gaggcaggct   120
cccggacagg gcctggagtg gatgggcggc atcatcccca ttttcggcag ggccaactac   180
gcccagaagt tccaggggaag ggtcaccatc accgccgacg agagcaccag caccgcctac   240
atggaactca gcagcctgag gagcgaggac accgccgtgt actattgcgc caggctgctg   300
ggcgagagcg gcatggacgt gtggggccag ggcaccaccg tgactgtgag cagc         354

<210> SEQ ID NO 33
<211> LENGTH: 106
<212> TYPE: PRT
<213> ORGANISM: Artificial
<220> FEATURE:
<223> OTHER INFORMATION: 42Y073-86F08-3 variable light chain amino acid
      sequence

<400> SEQUENCE: 33

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Leu His Thr Ile Thr

```
                        85                  90                  95
Phe Gly Gly Gly Thr Lys Val Glu Ile Lys
                    100                 105

<210> SEQ ID NO 34
<211> LENGTH: 122
<212> TYPE: PRT
<213> ORGANISM: Artificial
<220> FEATURE:
<223> OTHER INFORMATION: 42Y073-86F08-3 variable heavy chain amino acid
      sequence

<400> SEQUENCE: 34

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Val Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ala Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Gly Tyr Tyr Gly Asp Lys Asp Pro Met Asp Val Trp
            100                 105                 110

Gly Gln Gly Thr Thr Val Thr Val Ser Ser
        115                 120

<210> SEQ ID NO 35
<211> LENGTH: 318
<212> TYPE: DNA
<213> ORGANISM: Artificial
<220> FEATURE:
<223> OTHER INFORMATION: 42Y073-86F08-3 variable light chain nucleic
      acid sequence

<400> SEQUENCE: 35
gacatccagc tgacccagag ccctagcagc ctgagcgcca gcgtgggaga cagggtgacc      60
atcacctgca gggccagcca gtccatcagc agctacctga actggtacca gcagaagccc     120
ggcaaggccc ccaagctgct gatctacgcc gcaagctcac tgcagagcgg cgtgccctct     180
aggtttagcg gcagcggcag cggcaccgac ttcaccctga ccatcagcag cctccagccc     240
gaggacttcg ccacctacta ctgccagcag gtgctgcaca ccatcacttt cggcggcggc     300
accaaggtgg agattaag                                                   318

<210> SEQ ID NO 36
<211> LENGTH: 366
<212> TYPE: DNA
<213> ORGANISM: Artificial
<220> FEATURE:
<223> OTHER INFORMATION: 42Y073-86F08-3 variable heavy chain nucleic
      acid sequence

<400> SEQUENCE: 36
caggtgcagc tggtgcagag cggcgccgag gtgaaaaagc ccggcagcag cgtgaaggtg      60
agctgcaagg cctccggcgg gaccttcgtg aactacgcca tcagctgggt gaggcaggct     120
cccggacagg gcctggagtg gatgggcggc atcatccccg ccctgggcac cgccaactac     180
```

```
gcccagaagt tccagggaag ggtcaccatc accgccgacg agagcaccag caccgcctac    240
atggaactca gcagcctgag gagcgaggac accgccgtgt actattgcgc caggggcgcc    300
ggctactacg gcgacaagga ccccatggac gtgtggggcc agggcaccac cgtgactgtg    360
agcagc                                                               366
```

```
<210> SEQ ID NO 37
<211> LENGTH: 106
<212> TYPE: PRT
<213> ORGANISM: Artificial
<220> FEATURE:
<223> OTHER INFORMATION: 42Y073-86F08-4 variable light chain amino acid
      sequence

<400> SEQUENCE: 37

Asp Ile Gln Leu Thr Gln Ser Pro Ser Ser Leu Ser Ala Ser Val Gly
1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Leu His Thr Ile Thr
                85                  90                  95

Phe Gly Gly Gly Thr Lys Val Glu Ile Lys
            100                 105

<210> SEQ ID NO 38
<211> LENGTH: 122
<212> TYPE: PRT
<213> ORGANISM: Artificial
<220> FEATURE:
<223> OTHER INFORMATION: 42Y073-86F08-4 variable heavy chain amino acid
      sequence

<400> SEQUENCE: 38

Gln Val Gln Leu Val Gln Ser Gly Ala Glu Val Lys Lys Pro Gly Ser
1               5                  10                  15

Ser Val Lys Val Ser Cys Lys Ala Ser Gly Gly Thr Phe Ser Glu Tyr
            20                  25                  30

Ala Ile His Trp Val Arg Gln Ala Pro Gly Gln Gly Leu Glu Trp Met
        35                  40                  45

Gly Asn Ile Ile Pro Ile Phe Gly Thr Ala Gly Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Gly Tyr Tyr Gly Asp Lys Asp Pro Met Asp Val Trp
            100                 105                 110

Gly Gln Gly Thr Thr Val Thr Val Ser Ser
        115                 120

<210> SEQ ID NO 39
<211> LENGTH: 318
```

```
<212> TYPE: DNA
<213> ORGANISM: Artificial
<220> FEATURE:
<223> OTHER INFORMATION: 42Y073-86F08-4 variable light chain nucleic
      acid sequence

<400> SEQUENCE: 39
gacatccagc tgacccagag ccctagcagc ctgagcgcca gcgtgggaga cagggtgacc     60
atcacctgca gggccagcca gtccatcagc agctacctga actggtacca gcagaagccc    120
ggcaaggccc ccaagctgct gatctacgcc gcaagctcac tgcagagcgg cgtgccctct    180
aggtttagcg gcagcggcag cggcaccgac ttcaccctga ccatcagcag cctccagccc    240
gaggacttcg ccacctacta ctgccagcag gtgctgcaca ccatcacttt cggcggcggc    300
accaaggtgg agattaag                                                  318

<210> SEQ ID NO 40
<211> LENGTH: 366
<212> TYPE: DNA
<213> ORGANISM: Artificial
<220> FEATURE:
<223> OTHER INFORMATION: 42Y073-86F08-4 variable heavy chain nucleic
      acid sequence

<400> SEQUENCE: 40
caggtgcagc tggtgcagag cggcgccgag gtgaaaaagc ccggcagcag cgtgaaggtg     60
agctgcaagg cctccggcgg gaccttcagc gagtacgcca tccactgggt gaggcaggct    120
cccggacagg gcctggagtg gatgggcaac atcatcccca ttttcggcac cgccggctac    180
gcccagaagt tccagggaag ggtcaccatc accgccgacg agagcaccag caccgcctac    240
atggaactca gcagcctgag gagcgaggac accgccgtgt actattgcgc caggggcgcc    300
ggctactacg gcgacaagga ccccatggac gtgtggggcc agggcaccac cgtgactgtg    360
agcagc                                                               366

<210> SEQ ID NO 41
<211> LENGTH: 106
<212> TYPE: PRT
<213> ORGANISM: Artificial
<220> FEATURE:
<223> OTHER INFORMATION: 42Y073-86F08-8 variable light chain amino acid
      sequence

<400> SEQUENCE: 41

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Leu His Thr Ile Thr
                85                  90                  95

Phe Gly Gly Gly Thr Lys Val Glu Ile Lys
            100                 105

<210> SEQ ID NO 42
```

```
<211> LENGTH: 122
<212> TYPE: PRT
<213> ORGANISM: Artificial
<220> FEATURE:
<223> OTHER INFORMATION: 42Y073-86F08-8 variable heavy chain amino acid
      sequence

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Trp Leu Tyr
            20                  25                  30

Ala Ile Ser Trp Val Arg Gln Ala Pro Gly Gln Gly Leu Glu Trp Met
        35                  40                  45

Gly Gly Ile Ile Pro Gln Leu Gly Thr Ala Asn Tyr Ala Gln Lys Phe
    50                  55                  60

Gln Gly Arg Val Thr Ile Thr Ala Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Gly Tyr Tyr Gly Asp Lys Asp Pro Met Asp Val Trp
            100                 105                 110

Gly Gln Gly Thr Thr Val Thr Val Ser Ser
        115                 120

<210> SEQ ID NO 43
<211> LENGTH: 318
<212> TYPE: DNA
<213> ORGANISM: Artificial
<220> FEATURE:
<223> OTHER INFORMATION: 42Y073-86F08-8 variable light chain nucleic
      acid sequence

<400> SEQUENCE: 43
gacatccagc tgacccagag ccctagcagc ctgagcgcca gcgtgggaga cagggtgacc      60
atcacctgca gggccagcca gtccatcagc agctacctga actggtacca gcagaagccc     120
ggcaaggccc ccaagctgct gatctacgcc gcaagctcac tgcagagcgg cgtgccctct     180
aggtttagcg gcagcggcag cggcaccgac ttcaccctga ccatcagcag cctccagccc     240
gaggacttcg ccacctacta ctgccagcag gtgctgcaca ccatcacttt cggcggcggc     300
accaaggtgg agattaag                                                   318

<210> SEQ ID NO 44
<211> LENGTH: 366
<212> TYPE: DNA
<213> ORGANISM: Artificial
<220> FEATURE:
<223> OTHER INFORMATION: 42Y073-86F08-8 variable heavy chain nucleic
      acid sequence

<400> SEQUENCE: 44
caggtgcagc tggtgcagag cggcgccgag gtgaaaaagc ccggcagcag cgtgaaggtg      60
agctgcaagg cctccggcgg gaccttctgg ctgtacgcca tcagctgggt gaggcaggct     120
cccggacagg gcctggagtg gatgggcggc atcatccccc agctgggcac cgccaactac     180
gcccagaagt tccagggaag ggtcaccatc accgccgacg agagcaccag caccgcctac     240
atggaactca gcagcctgag gagcgaggac accgccgtgt actattgcgc cagggggcgcc    300 ggctactacg gcgacaagga ccccatggac gtgtggggcc agggcaccac cgtgactgtg     360
``` agcagc 366

<210> SEQ ID NO 45
<211> LENGTH: 106
<212> TYPE: PRT
<213> ORGANISM: Artificial
<220> FEATURE:
<223> OTHER INFORMATION: 42Y073-86F08-17 variable light chain amino acid
      sequence

<400> SEQUENCE: 45

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Leu His Thr Ile Thr
                85                  90                  95

Phe Gly Gly Gly Thr Lys Val Glu Ile Lys
            100                 105
```

<210> SEQ ID NO 46
<211> LENGTH: 122
<212> TYPE: PRT
<213> ORGANISM: Artificial
<220> FEATURE:
<223> OTHER INFORMATION: 42Y073-86F08-17 variable heavy chain amino acid
      sequence

<400> SEQUENCE: 46

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Glu Tyr
            20                  25                  30

Ala Ile Ser Trp Val Arg Gln Ala Pro Gly Gln Gly Leu Glu Trp Met
        35                  40                  45

Gly Gly Ile Ile Pro Val Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Gly Tyr Tyr Gly Asp Lys Asp Pro Met Asp Val Trp
            100                 105                 110

Gly Gln Gly Thr Thr Val Thr Val Ser Ser
            115                 120
```

<210> SEQ ID NO 47
<211> LENGTH: 318
<212> TYPE: DNA
<213> ORGANISM: Artificial
<220> FEATURE:
<223> OTHER INFORMATION: 42Y073-86F08-17 variable light chain nucleic
      acid sequence

<400> SEQUENCE: 47

```
gacatccagc tgacccagag ccctagcagc ctgagcgcca gcgtgggaga cagggtgacc        60
atcacctgca gggccagcca gtccatcagc agctacctga actggtacca gcagaagccc       120
ggcaaggccc ccaagctgct gatctacgcc gcaagctcac tgcagagcgg cgtgccctct       180
aggtttagcg gcagcggcag cggcaccgac ttcaccctga ccatcagcag cctccagccc       240
gaggacttcg ccacctacta ctgccagcag gtgctgcaca ccatcacttt cggcggcggc       300
accaaggtgg agattaag                                                      318
```

<210> SEQ ID NO 48
<211> LENGTH: 366
<212> TYPE: DNA
<213> ORGANISM: Artificial
<220> FEATURE:
<223> OTHER INFORMATION: 42Y073-86F08-17 variable heavy chain nucleic
      acid sequence

<400> SEQUENCE: 48

```
caggtgcagc tggtgcagag cggcgccgag gtgaaaaagc ccggcagcag cgtgaaggtg        60
agctgcaagg cctccggcgg gaccttcagg gagtacgcca tcagctgggt gaggcaggct       120
cccggacagg gcctggagtg gatgggcggc atcatcccg tgttcggcac cgccaactac       180
gcccagaagt tccagggaag ggtcaccatc accgccgacg agagccacag caccgcctac       240
atggaactca gcagcctgag gagcgaggac accgccgtgt actattgcgc caggggcgcc       300
ggctactacg gcgacaagga ccccatggac gtgtggggcc agggcaccac cgtgactgtg       360
agcagc                                                                   366
```

<210> SEQ ID NO 49
<211> LENGTH: 106
<212> TYPE: PRT
<213> ORGANISM: Artificial
<220> FEATURE:
<223> OTHER INFORMATION: 42Y073-86F08-22 variable light chain amino acid
      sequence

<400> SEQUENCE: 49

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Leu His Thr Ile Thr
                85                  90                  95

Phe Gly Gly Gly Thr Lys Val Glu Ile Lys
            100                 105
```

<210> SEQ ID NO 50
<211> LENGTH: 122
<212> TYPE: PRT
<213> ORGANISM: Artificial
<220> FEATURE:
<223> OTHER INFORMATION: 42Y073-86F08-22 variable heavy chain amino acid
      sequence

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asp Ser Tyr
            20                  25                  30

Ala Met His Trp Val Arg Gln Ala Pro Gly Gln Gly Leu Glu Trp Met
        35                  40                  45

Gly Gly Ile Ile Pro Ile Phe Gly Thr Ala Trp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Gly Tyr Tyr Gly Asp Lys Asp Pro Met Asp Val Trp
            100                 105                 110

Gly Gln Gly Thr Thr Val Thr Val Ser Ser
        115                 120

<210> SEQ ID NO 51
<211> LENGTH: 318
<212> TYPE: DNA
<213> ORGANISM: Artificial
<220> FEATURE:
<223> OTHER INFORMATION: 42Y073-86F08-22 variable light chain nucleic
      acid sequence

<400> SEQUENCE: 51
gacatccagc tgacccagag ccctagcagc ctgagcgcca gcgtgggaga cagggtgacc      60
atcacctgca gggccagcca gtccatcagc agctacctga actggtacca gcagaagccc     120
ggcaaggccc ccaagctgct gatctacgcc gcaagctcac tgcagagcgg cgtgccctct     180
aggtttagcg gcagcggcag cggcaccgac ttcaccctga ccatcagcag cctccagccc     240
gaggacttcg ccacctacta ctgccagcag gtgctgcaca ccatcacttt cggcggcggc     300
accaaggtgg agattaag                                                   318

<210> SEQ ID NO 52
<211> LENGTH: 366
<212> TYPE: DNA
<213> ORGANISM: Artificial
<220> FEATURE:
<223> OTHER INFORMATION: 42Y073-86F08-22 variable heavy chain nucleic
      acid sequence

<400> SEQUENCE: 52
caggtgcagc tggtgcagag cggcgccgag gtgaaaaagc ccggcgccag cgtgaaggtg      60
agctgcaagg cctccggcta caccttcgac agctacgcca tgcactgggt gaggcaggct     120
cccggacagg gcctggagtg gatgggcggc atcatcccca ttttcggcac cgcctggtac     180
gcccagaagt tccagggaag ggtcaccatc accgccgacg agagcaccag caccgcctac     240
atggaactca gcagcctgag gagcgaggac accgccgtgt actattgcgc caggggcgcc     300
ggctactacg gcgacaagga ccccatggac gtgtggggcc agggcaccac cgtgactgtg     360
agcagc                                                                366

<210> SEQ ID NO 53
<211> LENGTH: 106
<212> TYPE: PRT
<213> ORGANISM: Artificial

<220> FEATURE:
<223> OTHER INFORMATION: 42Y073-86F08-47 variable light chain amino acid
     sequence

<400> SEQUENCE: 53

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Leu His Thr Ile Thr
                85                  90                  95

Phe Gly Gly Gly Thr Lys Val Glu Ile Lys
            100                 105

<210> SEQ ID NO 54
<211> LENGTH: 122
<212> TYPE: PRT
<213> ORGANISM: Artificial
<220> FEATURE:
<223> OTHER INFORMATION: 42Y073-86F08-47 variable heavy chain amino acid
     sequence

<400> SEQUENCE: 54

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Gln Tyr
            20                  25                  30

Ala Ile His Trp Val Arg Gln Ala Pro Gly Gln Gly Leu Glu Trp Met
        35                  40                  45

Gly Val Ile Ile Pro Ile Phe Gly Lys Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Gly Tyr Tyr Gly Asp Lys Asp Pro Met Asp Val Trp
            100                 105                 110

Gly Gln Gly Thr Thr Val Thr Val Ser Ser
        115                 120

<210> SEQ ID NO 55
<211> LENGTH: 318
<212> TYPE: DNA
<213> ORGANISM: Artificial
<220> FEATURE:
<223> OTHER INFORMATION: 42Y073-86F08-47 variable light chain nucleic
     acid sequence

<400> SEQUENCE: 55
gacatccagc tgacccagag ccctagcagc ctgagcgcca gcgtgggaga cagggtgacc      60
atcacctgca gggccagcca gtccatcagc agctacctga actggtacca gcagaagccc     120
ggcaaggccc ccaagctgct gatctacgcc gcaagctcac tgcagagcgg cgtgccctct     180

```
aggtttagcg gcagcggcag cggcaccgac ttcaccctga ccatcagcag cctccagccc    240
gaggacttcg ccacctacta ctgccagcag gtgctgcaca ccatcacttt cggcggcggc    300
accaaggtgg agattaag                                                  318
```

<210> SEQ ID NO 56
<211> LENGTH: 366
<212> TYPE: DNA
<213> ORGANISM: Artificial
<220> FEATURE:
<223> OTHER INFORMATION: 42Y073-86F08-47 variable heavy chain nucleic
    acid sequence

<400> SEQUENCE: 56

```
caggtgcagc tggtgcagag cggcgccgag gtgaaaaagc ccggcagcag cgtgaaggtg     60
agctgcaagg cctccggcgg gaccttcagc cagtacgcca tccactgggt gaggcaggct    120
cccggacagg gcctggagtg gatgggcgtg atcatcccca ttttcggcaa ggccaactac    180
gcccagaagt tccagggaag ggtcaccatc accgccgacg agagcaccag caccgcctac    240
atggaactca gcagcctgag gagcgaggac accgccgtgt actattgcgc caggggcgcc    300
ggctactacg cgacaaggga ccccatggac gtgtggggcc agggcaccac cgtgactgtg    360
agcagc                                                               366
```

<210> SEQ ID NO 57
<211> LENGTH: 107
<212> TYPE: PRT
<213> ORGANISM: Artificial
<220> FEATURE:
<223> OTHER INFORMATION: 42Y073-2B04-46 variable light chain amino acid
    sequence

<400> SEQUENCE: 57

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Leu Asp Asn Trp Pro Ile
                85                  90                  95

Thr Phe Gly Gly Gly Thr Lys Val Glu Ile Lys
            100                 105
```

<210> SEQ ID NO 58
<211> LENGTH: 126
<212> TYPE: PRT
<213> ORGANISM: Artificial
<220> FEATURE:
<223> OTHER INFORMATION: 42Y073-2B04-46 variable heavy chain amino acid
    sequence

<400> SEQUENCE: 58

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Arg Arg Tyr
            20                  25                  30
```

Tyr Trp Ser Trp Ile Arg Gln Pro Pro Gly Lys Gly Leu Glu Trp Ile
         35                  40                  45

Gly Glu Ile Asp Gly Trp Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Gly Ser Val Asp Phe Trp Ser Gly Ser Asp Tyr Tyr Tyr Tyr
                100                 105                 110

Met Asp Val Trp Gly Lys Gly Ala Thr Val Thr Val Ser Ser
            115                 120                 125

<210> SEQ ID NO 59
<211> LENGTH: 321
<212> TYPE: DNA
<213> ORGANISM: Artificial
<220> FEATURE:
<223> OTHER INFORMATION: 42Y073-2B04-46 variable light chain nucleic
      acid sequence

<400> SEQUENCE: 59
gagatcgtgc tgacccagag ccccgcaacc ctgtccctga gccccggcga aagggccact        60
ctgagctgca gggccagcca gagcgtgagc agctacctcg cctggtacca gcagaagccc       120
ggccaggccc ctaggctgct gatctacgac gccagcaaga gggccaccgg cattcccgcc       180
aggttcagcg gcagcggcag cggcaccgac ttcaccctga ccatcagcag cctggagccc       240
gaggacttcg ccgtctacta ctgccagcag ctggacaact ggcccatcac cttcggggc       300 ggcaccaagg tggagatcaa g                                                 321

<210> SEQ ID NO 60
<211> LENGTH: 377
<212> TYPE: DNA
<213> ORGANISM: Artificial
<220> FEATURE:
<223> OTHER INFORMATION: 42Y073-2B04-46 variable heavy chain nucleic
      acid sequence

<400> SEQUENCE: 60
caggtgcagc tgcagcagtg gggcgccgga ctgctgaagc ccagcgagac cctgagcctg        60
acctgcgccg tgtacggcgg gtccttcagg aggtactact ggagctggat caggcagccc       120
cccggcaaag gcctggagtg gatcggcgag atcgacggct ggggcagcac caactacaac       180
cccagcctca agagcagggt gaccatcagc gtggacacca gcaagaacca gttcagcctg       240
aagctgagca gcgtgaccgc cgccgacacc gccgtgtact attgcgccag ggcggcagc        300 gtggacttct ggagcggcag cgactactac tactacatgg acgtgtgggg caagggcgcc       360
accgtcaccg tgagcag                                                      377

<210> SEQ ID NO 61
<211> LENGTH: 107
<212> TYPE: PRT
<213> ORGANISM: Artificial
<220> FEATURE:
<223> OTHER INFORMATION: 42Y073-1A01-85 variable light chain amino acid
      sequence

<400> SEQUENCE: 61

Asp Ile Gln Met Thr Gln Ser Pro Ser Ser Leu Ser Ala Ser Val Gly

```
               1               5                  10                 15
Asp Arg Val Thr Ile Thr Cys Arg Ala Ser Gln Ser Ile Ser Ser Tyr
                     20                 25                 30

Leu Asn Trp Tyr Gln Gln Lys Pro Gly Lys Ala Pro Lys Leu Leu Ile
             35                 40                 45

Tyr Ala Ala Ser Ser Leu Gln Ser Gly Val Pro Ser Arg Phe Ser Gly
         50                 55                 60

Ser Gly Ser Gly Thr Asp Phe Thr Leu Thr Ile Ser Ser Leu Gln Pro
65                  70                 75                 80

Glu Asp Phe Ala Thr Tyr Tyr Cys Gln Gln Ser Leu Tyr Pro Pro Arg
                 85                 90                 95

Thr Phe Gly Gly Gly Thr Lys Val Glu Ile Lys
                100                105
```

<210> SEQ ID NO 62
<211> LENGTH: 123
<212> TYPE: PRT
<213> ORGANISM: Artificial
<220> FEATURE:
<223> OTHER INFORMATION: 42Y073-1A01-85 variable heavy chain amino acid
      sequence

<400> SEQUENCE: 62

```
Gln Val Gln Leu Val Gln Ser Gly Ala Glu Val Lys Lys Pro Gly Ala
1               5                  10                 15

Ser Val Lys Val Ser Cys Lys Ala Ser Gly Tyr Thr Phe Thr Ser Tyr
             20                 25                 30

Pro Met His Trp Val Arg Gln Ala Pro Gly Gln Gly Leu Glu Trp Met
         35                 40                 45

Gly Ile Ile Asn Pro Ser Gly Gly Phe Thr Ser Tyr Ala Gln Lys Phe
     50                 55                 60

Gln Gly Arg Val Thr Met Thr Arg Asp Thr Ser Thr Ser Thr Val Tyr
65                  70                 75                 80

Met Glu Leu Ser Ser Leu Arg Ser Glu Asp Thr Ala Val Tyr Tyr Cys
                 85                 90                 95

Ala Arg Glu Thr Ala Tyr Tyr Thr Thr Lys Gly Asn Trp Phe Asp Pro
                100                105                110

Trp Gly Gln Gly Thr Leu Val Thr Val Ser Ala
         115                120
```

<210> SEQ ID NO 63
<211> LENGTH: 321
<212> TYPE: DNA
<213> ORGANISM: Artificial
<220> FEATURE:
<223> OTHER INFORMATION: 42Y073-1A01-85 variable light chain nucleic
      acid sequence

<400> SEQUENCE: 63

```
gacatccaga tgacccagag ccctagcagc ctgagcgcca gcgtgggaga cagggtgacc      60
atcacctgca gggccagcca gtccatcagc agctacctga actggtacca gcagaagccc     120
ggcaaggccc ccaagctgct gatctacgcc gcaagctcac tgcagagcgg cgtgccctct     180
aggtttagcg gcagcggcag cggcaccgac ttcaccctga ccatcagcag cctccagccc     240
gaggacttcg ccacctacta ctgccagcag agcctgtacc cccccaggac tttcggcggc     300
ggcaccaagg tggagattaa g                                               321
```

```
<210> SEQ ID NO 64
<211> LENGTH: 369
<212> TYPE: DNA
<213> ORGANISM: Artificial
<220> FEATURE:
<223> OTHER INFORMATION: 42Y073-1A01-85 variable heavy chain nucleic
      acid sequence

<400> SEQUENCE: 64
caggtgcagc tggtgcagag cggcgccgaa gtgaaaaagc ccggcgccag cgtgaaggtc     60
agctgcaagg cctccgggta caccttcacc agctacccca tgcactgggt gaggcaggcc    120
cccggccagg gcctcgagtg gatgggcatc atcaaccccg cggaggctt caccagctac     180 gcccagaagt tccagggcag ggtgaccatg acaagggaca ccagcaccag caccgtgtac    240
atggagctga gcagcctgag gagcgaggac accgccgtgt attactgcgc aaggagacc    300 gcctactaca ccaccaaggg caactggttc gaccctggg gccagggcac cctggtgacc     360
gtgagcgcc                                                            369

<210> SEQ ID NO 65
<211> LENGTH: 107
<212> TYPE: PRT
<213> ORGANISM: Artificial
<220> FEATURE:
<223> OTHER INFORMATION: 42Y073-1A01-97 variable light chain amino acid
      sequence

<400> SEQUENCE: 65
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Tyr Pro Pro Arg
                85                  90                  95

Thr Phe Gly Gly Gly Thr Lys Val Glu Ile Lys
            100                 105

```
<210> SEQ ID NO 66
<211> LENGTH: 123
<212> TYPE: PRT
<213> ORGANISM: Artificial
<220> FEATURE:
<223> OTHER INFORMATION: 42Y073-1A01-97 variable heavy chain amino acid
      sequence

<400> SEQUENCE: 66
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Ala
            20                  25                  30

Ala Met His Trp Val Arg Gln Ala Pro Gly Gln Gly Leu Glu Trp Met
        35                  40                  45

Gly Ile Ile Asn Pro Ala Gly Gly Tyr Thr Ser Tyr Ala Gln Lys Phe
    50                  55                  60

Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
            85                  90                  95

Ala Arg Glu Thr Ala Tyr Tyr Thr Thr Lys Gly Asn Trp Phe Asp Pro
        100                 105                 110

Trp Gly Gln Gly Thr Leu Val Thr Val Ser Ser
        115                 120

<210> SEQ ID NO 67
<211> LENGTH: 321
<212> TYPE: DNA
<213> ORGANISM: Artificial
<220> FEATURE:
<223> OTHER INFORMATION: 42Y073-1A01-97 variable light chain nucleic
      acid sequence

<400> SEQUENCE: 67
gacatccaga tgacccagag ccctagcagc ctgagcgcca gcgtgggaga cagggtgacc      60
atcacctgca gggccagcca gtccatcagc agctacctga actggtacca gcagaagccc     120
ggcaaggccc ccaagctgct gatctacgcc gcaagctcac tgcagagcgg cgtgccctct     180
aggtttagcg gcagcggcag cggcaccgac ttcaccctga ccatcagcag cctccagccc     240
gaggacttcg ccacctacta ctgccagcag agcctgtacc cccccaggac tttcggcggc     300
ggcaccaagg tggagattaa g                                                321

<210> SEQ ID NO 68
<211> LENGTH: 369
<212> TYPE: DNA
<213> ORGANISM: Artificial
<220> FEATURE:
<223> OTHER INFORMATION: 42Y073-1A01-97 variable heavy chain nucleic
      acid sequence

<400> SEQUENCE: 68
caggtgcagc tggtgcagag cggcgccgaa gtgaaaaagc ccggcgccag cgtgaaggtc      60
agctgcaagg cctccgggta caccttcacc agggccgcca tgcactgggt gaggcaggcc     120
cccggccagg gcctcgagtg gatgggcatc atcaaccccg ccggaggcta caccagctac     180
gcccagaagt tccagggcag ggtgaccatg acaagggaca ccagcaccag caccgtgtac     240
atggagctga gcagcctgag gagcgaggac accgccgtgt attactgcgc aagggagacc     300
gcctactaca ccaccaaggg caactggttc gaccccctgg gccagggcac cctggtgacc     360
gtgagctct                                                              369

<210> SEQ ID NO 69
<211> LENGTH: 107
<212> TYPE: PRT
<213> ORGANISM: Artificial
<220> FEATURE:
<223> OTHER INFORMATION: 42Y073-1A01-100 variable light chain amino acid
      sequence

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Tyr Pro Pro Arg
                85                  90                  95

Thr Phe Gly Gly Gly Thr Lys Val Glu Ile Lys
            100                 105

<210> SEQ ID NO 70
<211> LENGTH: 123
<212> TYPE: PRT
<213> ORGANISM: Artificial
<220> FEATURE:
<223> OTHER INFORMATION: 42Y073-1A01-100 variable heavy chain amino acid
      sequence

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Arg Met His Trp Val Arg Gln Ala Pro Gly Gln Gly Leu Glu Trp Met
        35                  40                  45

Gly Ile Ile Asn Pro Ser Gly Gly Leu Thr Gln Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Thr Ala Tyr Tyr Thr Thr Lys Gly Asn Trp Phe Asp Pro
            100                 105                 110

Trp Gly Gln Gly Thr Leu Val Thr Val Ser Ser
        115                 120

<210> SEQ ID NO 71
<211> LENGTH: 321
<212> TYPE: DNA
<213> ORGANISM: Artificial
<220> FEATURE:
<223> OTHER INFORMATION: 42Y073-1A01-100 variable light chain nucleic
      acid sequence

<400> SEQUENCE: 71
gacatccaga tgacccagag ccctagcagc ctgagcgcca gcgtgggaga cagggtgacc      60
atcacctgca gggccagcca gtccatcagc agctacctga actggtacca gcagaagccc     120
ggcaaggccc ccaagctgct gatctacgcc gcaagctcac tgcagagcgg cgtgccctct     180
aggtttagcg gcagcggcag cggcaccgac ttcaccctga ccatcagcag cctccagccc     240
gaggacttcg ccacctacta ctgccagcag agcctgtacc ccccaggac tttcggcggc      300 ggcaccaagg tggagattaa g                                               321

<210> SEQ ID NO 72
<211> LENGTH: 369
<212> TYPE: DNA
<213> ORGANISM: Artificial
<220> FEATURE:
<223> OTHER INFORMATION: 42Y073-1A01-100 variable heavy chain nucleic
      acid sequence

<400> SEQUENCE: 72

```
caggtgcagc tggtgcagag cggcgccgaa gtgaaaaagc ccggcgccag cgtgaaggtc      60
agctgcaagg cctccgggta caccttcacc acctacagga tgcactgggt gaggcaggcc     120
cccggccagg gcctcgagtg gatgggcatc atcaacccca gcggaggcct gacccagtac     180
gcccagaagt tccagggcag ggtgaccatg acaagggaca ccagcaccag caccgtgtac     240
atggagctga gcagcctgag gagcgaggac accgccgtgt attactgcgc aagggagacc     300
gcctactaca ccaccaaggg caactggttc gaccctgggg ccagggcac  cctggtgacc     360
gtgagctct                                                             369
```

<210> SEQ ID NO 73
<211> LENGTH: 107
<212> TYPE: PRT
<213> ORGANISM: Artificial
<220> FEATURE:
<223> OTHER INFORMATION: 42Y073-1A01-103 variable light chain amino acid sequence

<400> SEQUENCE: 73

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Leu Tyr Pro Pro Arg
                85                  90                  95
Thr Phe Gly Gly Gly Thr Lys Val Glu Ile Lys
            100                 105
```

<210> SEQ ID NO 74
<211> LENGTH: 123
<212> TYPE: PRT
<213> ORGANISM: Artificial
<220> FEATURE:
<223> OTHER INFORMATION: 42Y073-1A01-103 variable heavy chain amino acid sequence

<400> SEQUENCE: 74

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ala Tyr
            20                  25                  30
Gln Met His Trp Val Arg Gln Ala Pro Gly Gln Gly Leu Glu Trp Met
        35                  40                  45
Gly Ile Ile Asn Pro Ala Gly Gly Trp Thr Ser Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Glu Thr Ala Tyr Tyr Thr Thr Lys Gly Asn Trp Phe Asp Pro
```

100                 105                 110
Trp Gly Gln Gly Thr Leu Val Thr Val Ser Ser
            115                 120

<210> SEQ ID NO 75
<211> LENGTH: 321
<212> TYPE: DNA
<213> ORGANISM: Artificial
<220> FEATURE:
<223> OTHER INFORMATION: 42Y073-1A01-103 variable light chain nucleic
      acid sequence

<400> SEQUENCE: 75
gacatccaga tgacccagag ccctagcagc ctgagcgcca gcgtgggaga cagggtgacc    60
atcacctgca gggccagcca gtccatcagc agctacctga actggtacca gcagaagccc   120
ggcaaggccc ccaagctgct gatctacgcc gcaagctcac tgcagagcgg cgtgccctct   180
aggtttagcg gcagcggcag cggcaccgac ttcaccctga ccatcagcag cctccagccc   240
gaggacttcg ccacctacta ctgccagcag agcctgtacc cccccaggac tttcggcggc   300
ggcaccaagg tggagattaa g                                             321

<210> SEQ ID NO 76
<211> LENGTH: 369
<212> TYPE: DNA
<213> ORGANISM: Artificial
<220> FEATURE:
<223> OTHER INFORMATION: 42Y073-1A01-103 variable heavy chain nucleic
      acid sequence

<400> SEQUENCE: 76
caggtgcagc tggtgcagag cggcgccgaa gtgaaaaagc ccggcgccag cgtgaaggtc    60
agctgcaagg cctccgggta caccttcacc gcctaccaga tgcactgggt gaggcaggcc   120
cccggccagg gcctcgagtg gatgggcatc atcaaccccg ccggaggctg gaccagctac   180
gcccagaagt tccagggcag ggtgaccatg acaagggaca ccagcaccag caccgtgtac   240
atggagctga gcagcctgag gagcgaggac accgccgtgt attactgcgc aagggagacc   300
gcctactaca ccaccaaggg caactggttc gaccctgggg ccagggcac ctggtgacc    360 gtgagctct                                                           369

<210> SEQ ID NO 77
<211> LENGTH: 107
<212> TYPE: PRT
<213> ORGANISM: Artificial
<220> FEATURE:
<223> OTHER INFORMATION: 42Y073-1A01-126 variable light chain amino acid
      sequence

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Tyr Pro Pro Arg
                85                  90                  95

Thr Phe Gly Gly Gly Thr Lys Val Glu Ile Lys
            100                 105

<210> SEQ ID NO 78
<211> LENGTH: 123
<212> TYPE: PRT
<213> ORGANISM: Artificial
<220> FEATURE:
<223> OTHER INFORMATION: 42Y073-1A01-126 variable heavy chain amino acid
      sequence

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Asn Met His Trp Val Arg Gln Ala Pro Gly Gln Gly Leu Glu Trp Met
        35                  40                  45

Gly Trp Ile Asn Pro Ala Gly Gly Ser Thr Ser Tyr Ala Gln Lys Phe
    50                  55                  60

Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Thr Ala Tyr Tyr Thr Thr Lys Gly Asn Trp Phe Asp Pro
            100                 105                 110

Trp Gly Gln Gly Thr Leu Val Thr Val Ser Ala
        115                 120

<210> SEQ ID NO 79
<211> LENGTH: 321
<212> TYPE: DNA
<213> ORGANISM: Artificial
<220> FEATURE:
<223> OTHER INFORMATION: 42Y073-1A01-126 variable light chain nucleic
      acid sequence

<400> SEQUENCE: 79
gacatccaga tgacccagag ccctagcagc ctgagcgcca gcgtgggaga cagggtgacc        60
atcacctgca gggccagcca gtccatcagc agctacctga actggtacca gcagaagccc       120
ggcaaggccc ccaagctgct gatctacgcc gcaagctcac tgcagagcgg cgtgccctct       180
aggtttagcg gcagcggcag cggcaccgac ttcaccctga ccatcagcag cctccagccc       240
gaggacttcg ccacctacta ctgccagcag agcctgtacc cccccaggac tttcggcggc       300
ggcaccaagg tggagattaa g                                                 321

<210> SEQ ID NO 80
<211> LENGTH: 369
<212> TYPE: DNA
<213> ORGANISM: Artificial
<220> FEATURE:
<223> OTHER INFORMATION: 42Y073-1A01-126 variable heavy chain nucleic
      acid sequence

<400> SEQUENCE: 80
caggtgcagc tggtgcagag cggcgccgaa gtgaaaaagc ccggcgccag cgtgaaggtc        60
agctgcaagg cctccgggta caccttcacc aggtacaaca tgcactgggt gaggcaggcc       120

-continued

```
cccggccagg gcctcgagtg gatgggctgg atcaaccccg ccggaggcag caccagctac    180
gcccagaagt tccagggcag ggtgaccatg acaagggaca ccagcaccag caccgtgtac    240
atggagctga gcagcctgag gagcgaggac accgccgtgt attactgcgc aagggagacc    300
gcctactaca ccaccaaggg caactggttc gaccccctggg gccagggcac cctggtgacc    360
gtgagcgcc                                                             369
```

<210> SEQ ID NO 81
<211> LENGTH: 107
<212> TYPE: PRT
<213> ORGANISM: Artificial
<220> FEATURE:
<223> OTHER INFORMATION: 42Y073-1A01-191 variable light chain amino acid
      sequence

<400> SEQUENCE: 81

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Tyr Pro Pro Arg
                85                  90                  95

Thr Phe Gly Gly Gly Thr Lys Val Glu Ile Lys
            100                 105
```

<210> SEQ ID NO 82
<211> LENGTH: 123
<212> TYPE: PRT
<213> ORGANISM: Artificial
<220> FEATURE:
<223> OTHER INFORMATION: 42Y073-1A01-191 variable heavy chain amino acid
      sequence

<400> SEQUENCE: 82

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Arg Met His Trp Val Arg Gln Ala Pro Gly Gln Gly Leu Glu Trp Met
        35                  40                  45

Gly Ile Ile Asn Pro Gln Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Thr Ala Tyr Tyr Thr Thr Lys Gly Asn Trp Phe Asp Pro
            100                 105                 110

Trp Gly Gln Gly Thr Leu Val Thr Val Ser Ala
        115                 120
```

<210> SEQ ID NO 83

-continued

<211> LENGTH: 321
<212> TYPE: DNA
<213> ORGANISM: Artificial
<220> FEATURE:
<223> OTHER INFORMATION: 42Y073-1A01-191 variable light chain nucleic
      acid sequence

<400> SEQUENCE: 83
gacatccaga tgacccagag ccctagcagc ctgagcgcca gcgtgggaga cagggtgacc     60
atcacctgca gggccagcca gtccatcagc agctacctga actggtacca gcagaagccc    120
ggcaaggccc ccaagctgct gatctacgcc gcaagctcac tgcagagcgg cgtgccctct    180
aggtttagcg gcagcggcag cggcaccgac ttcaccctga ccatcagcag cctccagccc    240
gaggacttcg ccacctacta ctgccagcag agcctgtacc cccccaggac tttcggcggc    300
ggcaccaagg tggagattaa g                                              321

<210> SEQ ID NO 84
<211> LENGTH: 369
<212> TYPE: DNA
<213> ORGANISM: Artificial
<220> FEATURE:
<223> OTHER INFORMATION: 42Y073-1A01-191 variable heavy chain nucleic
      acid sequence

<400> SEQUENCE: 84
caggtgcagc tggtgcagag cggcgccgaa gtgaaaaagc ccggcgccag cgtgaaggtc     60
agctgcaagg cctccgggta caccttcacc aagtacagga tgcactgggt gaggcaggcc    120
cccggccagg gctcgagtg gatgggcatc atcaaccccc agggaggcag caccagctac    180
gcccagaagt tccagggcag ggtgaccatg acaagggaca ccagcaccag caccgtgtac    240
atggagctga gcagcctgag gagcgaggac accgccgtgt attactgcgc aagggagacc    300
gcctactaca ccaccaaggg caactggttc gacccctggg gccagggcac cctggtgacc    360
gtgagcgcc                                                            369

<210> SEQ ID NO 85
<211> LENGTH: 106
<212> TYPE: PRT
<213> ORGANISM: Artificial
<220> FEATURE:
<223> OTHER INFORMATION: 42Y073-86F08-66 variable light chain amino acid
      sequence

<400> SEQUENCE: 85

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Leu His Thr Ile Thr
                85                  90                  95

Phe Gly Gly Gly Thr Lys Val Glu Ile Lys
            100                 105

```
<210> SEQ ID NO 86
<211> LENGTH: 122
<212> TYPE: PRT
<213> ORGANISM: Artificial
<220> FEATURE:
<223> OTHER INFORMATION: 42Y073-86F08-66 variable heavy chain amino acid
      sequence

<400> SEQUENCE: 86
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Val Glu Tyr
            20                  25                  30

Ala Ile Ser Trp Val Arg Gln Ala Pro Gly Gln Gly Leu Glu Trp Met
        35                  40                  45

Gly Gly Ile Ile Pro Ala Phe Gly Thr Ala Gln Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Gly Tyr Tyr Gly Asp Lys Asp Pro Met Asp Val Trp
            100                 105                 110

Gly Gln Gly Thr Thr Val Thr Val Ser Ser
        115                 120

```
<210> SEQ ID NO 87
<211> LENGTH: 318
<212> TYPE: DNA
<213> ORGANISM: Artificial
<220> FEATURE:
<223> OTHER INFORMATION: 42Y073-86F08-66 variable light chain nucleic
      acid sequence

<400> SEQUENCE: 87
```
gacatccagc tgacccagag ccctagcagc ctgagcgcca gcgtgggaga cagggtgacc      60
atcacctgca gggccagcca gtccatcagc agctacctga actggtacca gcagaagccc     120
ggcaaggccc ccaagctgct gatctacgcc gcaagctcac tgcagagcgg cgtgccctct     180
aggtttagcg gcagcggcag cggcaccgac ttcaccctga ccatcagcag cctccagccc     240
gaggacttcg ccacctacta ctgccagcag gtgctgcaca ccatcacttt cggcggcggc     300
accaaggtgg agattaag                                                   318

```
<210> SEQ ID NO 88
<211> LENGTH: 366
<212> TYPE: DNA
<213> ORGANISM: Artificial
<220> FEATURE:
<223> OTHER INFORMATION: 42Y073-86F08-66 variable heavy chain nucleic
      acid sequence

<400> SEQUENCE: 88
```
caggtgcagc tggtgcagag cggcgcagag gtgaaaaagc ccggcagcag cgtgaaggtg      60
agctgcaagg cctccggcgg gaccttcgtg gagtacgcca tcagctgggt gaggcaggct     120
cccggacagg gcctggagtg gatgggcggc atcatccccg ccttcggcac cgcccagtac     180
gcccagaagt tccagggaag ggtcaccatc accgccgacg agagcaccag caccgcctac     240
atggaactca gcagcctgag gagcgaggac accgccgtgt actattgcgc caggggagcc     300
ggctactacg gcgacaagga ccccatggac gtgtggggcc agggcaccac cgtgactgtg     360
agcagc 366

<210> SEQ ID NO 89
<211> LENGTH: 106
<212> TYPE: PRT
<213> ORGANISM: Artificial
<220> FEATURE:
<223> OTHER INFORMATION: 42Y073-86F08-16 variable light chain amino acid sequence

<400> SEQUENCE: 89

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Leu His Thr Ile Thr
                85                  90                  95

Phe Gly Gly Gly Thr Lys Val Glu Ile Lys
            100                 105
```

<210> SEQ ID NO 90
<211> LENGTH: 122
<212> TYPE: PRT
<213> ORGANISM: Artificial
<220> FEATURE:
<223> OTHER INFORMATION: 42Y073-86F08-16 variable heavy chain amino acid sequence

<400> SEQUENCE: 90

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Glu Tyr
            20                  25                  30

Ala Ile Ser Trp Val Arg Gln Ala Pro Gly Gln Gly Leu Glu Trp Met
        35                  40                  45

Gly Gly Ile Val Pro Val Phe Gly Thr Ala Lys Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Gly Tyr Tyr Gly Asp Lys Asp Pro Met Asp Val Trp
            100                 105                 110

Gly Gln Gly Thr Thr Val Thr Val Ser Ser
        115                 120
```

<210> SEQ ID NO 91
<211> LENGTH: 318
<212> TYPE: DNA
<213> ORGANISM: Artificial
<220> FEATURE:
<223> OTHER INFORMATION: 42Y073-86F08-16 variable light chain nucleic acid sequence

<400> SEQUENCE: 91

```
gacatccagc tgacccagag ccctagcagc ctgagcgcca gcgtgggaga cagggtgacc    60
atcacctgca gggccagcca gtccatcagc agctacctga actggtacca gcagaagccc   120
ggcaaggccc ccaagctgct gatctacgcc gcaagctcac tgcagagcgg cgtgccctct   180
aggtttagcg gcagcggcag cggcaccgac ttcaccctga ccatcagcag cctccagccc   240
gaggacttcg ccacctacta ctgccagcag gtgctgcaca ccatcacttt cggcggcggc   300
accaaggtgg agattaag                                                318
```

<210> SEQ ID NO 92
<211> LENGTH: 366
<212> TYPE: DNA
<213> ORGANISM: Artificial
<220> FEATURE:
<223> OTHER INFORMATION: 42Y073-86F08-16 variable heavy chain nucleic acid sequence

<400> SEQUENCE: 92

```
caggtgcagc tggtgcagag cggcgccgag gtgaaaaagc ccggcagcag cgtgaaggtg    60
agctgcaagg cctccggcgg gaccttcaac gagtacgcca tcagctgggt gaggcaggct   120
cccggacagg gcctggagtg gatgggcggc atcgtgcccg tgttcggcac cgccaagtac   180
gcccagaagt tccagggaag ggtcaccatc accgccacg agagcaccag caccgcctac   240
atggaactca gcagcctgag gagcgaggac accgccgtgt actattgcgc caggggcgcc   300
ggctactacg gcgacaagga ccccatggac gtgtggggcc agggcaccac cgtgactgtg   360
agcagc                                                             366
```

<210> SEQ ID NO 93
<211> LENGTH: 107
<212> TYPE: PRT
<213> ORGANISM: Artificial
<220> FEATURE:
<223> OTHER INFORMATION: 42Y073-86F04-23 variable light chain amino acid sequence

<400> SEQUENCE: 93

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Tyr Phe Ser Pro Pro
                85                  90                  95

Thr Phe Gly Gly Gly Thr Lys Val Glu Ile Lys
            100                 105
```

<210> SEQ ID NO 94
<211> LENGTH: 118
<212> TYPE: PRT
<213> ORGANISM: Artificial
<220> FEATURE:
<223> OTHER INFORMATION: 42Y073-86F04-23 variable heavy chain amino acid sequence

<400> SEQUENCE: 94

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Gly Tyr
            20                  25                  30

Pro Ile Ser Trp Val Arg Gln Ala Pro Gly Gln Gly Leu Glu Trp Met
        35                  40                  45

Gly Gly Ile Ile Pro Ile Met Gly Thr Ala Arg Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Gly Glu Ser Gly Met Asp Val Trp Gly Gln Gly Thr
            100                 105                 110

Thr Val Thr Val Ser Ser
        115

<210> SEQ ID NO 95
<211> LENGTH: 321
<212> TYPE: DNA
<213> ORGANISM: Artificial
<220> FEATURE:
<223> OTHER INFORMATION: 42Y073-86F04-23 variable light chain nucleic
      acid sequence

<400> SEQUENCE: 95
gacatccaga tgacccagag ccctagcagc ctgagcgcca gcgtgggaga cagggtgacc    60
atcacctgca gggccagcca gtccatcagc agctacctga actggtacca gcagaagccc   120
ggcaaggccc ccaagctgct gatctacgcc gcaagctcac tgcagagcgg cgtgccctct   180
aggtttagcg gcagcggcag cggcaccgac ttcaccctga ccatcagcag cctccagccc   240
gaggacttcg ccacctacta ctgccagcag ccctacttca gcccccccac tttcggcggc   300
ggcaccaagg tggagattaa g                                             321

<210> SEQ ID NO 96
<211> LENGTH: 354
<212> TYPE: DNA
<213> ORGANISM: Artificial
<220> FEATURE:
<223> OTHER INFORMATION: 42Y073-86F04-23 variable heavy chain nucleic
      acid sequence

<400> SEQUENCE: 96
caggtgcagc tggtgcagag cggcgccgag gtgaaaaagc ccggcagcag cgtgaaggtg    60
agctgcaagg cctccggcgg gaccttcagc ggctacccca tcagctgggt gaggcaggct   120
cccggacagg gcctggagtg gatgggcggc atcatcccca ttatgggcac cgccaggtac   180
gcccagaagt tccagggaag ggtcaccatc accgccgacg agagcaccag caccgcctac   240
atggaactca gcagcctgag gagcgaggac accgccgtgt actattgcgc caggctgctg   300
ggcgagagcg gcatggacgt gtggggccag ggcaccaccg tgactgtgag cagc         354

<210> SEQ ID NO 97
<211> LENGTH: 11
<212> TYPE: PRT
<213> ORGANISM: Artificial
<220> FEATURE:

```
<223> OTHER INFORMATION: CDRL1 amino acid sequence 1

<400> SEQUENCE: 97

Arg Ala Ser Gln Ser Ile Ser Ser Tyr Leu Asn
1               5                   10

<210> SEQ ID NO 98
<211> LENGTH: 11
<212> TYPE: PRT
<213> ORGANISM: Artificial
<220> FEATURE:
<223> OTHER INFORMATION: CDRL1 amino acid sequence 2

<400> SEQUENCE: 98

Arg Ala Ser Gln Ser Val Ser Ser Tyr Leu Ala
1               5                   10

<210> SEQ ID NO 99
<211> LENGTH: 7
<212> TYPE: PRT
<213> ORGANISM: Artificial
<220> FEATURE:
<223> OTHER INFORMATION: CDRL2 amino acid sequence 1

<400> SEQUENCE: 99

Ala Ala Ser Ser Leu Gln Ser
1               5

<210> SEQ ID NO 100
<211> LENGTH: 7
<212> TYPE: PRT
<213> ORGANISM: Artificial
<220> FEATURE:
<223> OTHER INFORMATION: CDRL2 amino acid sequence 2

<400> SEQUENCE: 100

Asp Ala Ser Lys Arg Ala Thr
1               5

<210> SEQ ID NO 101
<211> LENGTH: 8
<212> TYPE: PRT
<213> ORGANISM: Artificial
<220> FEATURE:
<223> OTHER INFORMATION: CDRL3 amino acid sequence 1

<400> SEQUENCE: 101

Gln Gln Val Leu His Thr Ile Thr
1               5

<210> SEQ ID NO 102
<211> LENGTH: 9
<212> TYPE: PRT
<213> ORGANISM: Artificial
<220> FEATURE:
<223> OTHER INFORMATION: CDRL3 amino acid sequence 2

<400> SEQUENCE: 102

Gln Gln Pro Tyr Phe Ser Pro Pro Thr
1               5

<210> SEQ ID NO 103
<211> LENGTH: 9
<212> TYPE: PRT
<213> ORGANISM: Artificial
<220> FEATURE:
<223> OTHER INFORMATION: CDRL3 amino acid sequence 3
```

<400> SEQUENCE: 103

Gln Gln Leu Asp Asn Trp Pro Ile Thr
1               5

<210> SEQ ID NO 104
<211> LENGTH: 9
<212> TYPE: PRT
<213> ORGANISM: Artificial
<220> FEATURE:
<223> OTHER INFORMATION: CDRL3 amino acid sequence 4

<400> SEQUENCE: 104

Gln Gln Ser Leu Tyr Pro Pro Arg Thr
1               5

<210> SEQ ID NO 105
<211> LENGTH: 5
<212> TYPE: PRT
<213> ORGANISM: Artificial
<220> FEATURE:
<223> OTHER INFORMATION: CDRH1 amino acid sequence 1

<400> SEQUENCE: 105

Ser Tyr Ala Ile Ser
1               5

<210> SEQ ID NO 106
<211> LENGTH: 5
<212> TYPE: PRT
<213> ORGANISM: Artificial
<220> FEATURE:
<223> OTHER INFORMATION: CDRH1 amino acid sequence 2

<400> SEQUENCE: 106

Tyr Asn Ala Ile Ser
1               5

<210> SEQ ID NO 107
<211> LENGTH: 5
<212> TYPE: PRT
<213> ORGANISM: Artificial
<220> FEATURE:
<223> OTHER INFORMATION: CDRH1 amino acid sequence 3

<400> SEQUENCE: 107

Ser Glu Ala Ile Ser
1               5

<210> SEQ ID NO 108
<211> LENGTH: 5
<212> TYPE: PRT
<213> ORGANISM: Artificial
<220> FEATURE:
<223> OTHER INFORMATION: CDRH1 amino acid sequence 4

<400> SEQUENCE: 108

Ser His Ala Ile Ser
1               5

<210> SEQ ID NO 109
<211> LENGTH: 5
<212> TYPE: PRT
<213> ORGANISM: Artificial
<220> FEATURE:
<223> OTHER INFORMATION: CDRH1 amino acid sequence 5

```
<400> SEQUENCE: 109

Gly His Ala Ile Ser
1               5

<210> SEQ ID NO 110
<211> LENGTH: 5
<212> TYPE: PRT
<213> ORGANISM: Artificial
<220> FEATURE:
<223> OTHER INFORMATION: CDRH1 amino acid sequence 6

<400> SEQUENCE: 110

Ser Arg Ala Ile Ser
1               5

<210> SEQ ID NO 111
<211> LENGTH: 5
<212> TYPE: PRT
<213> ORGANISM: Artificial
<220> FEATURE:
<223> OTHER INFORMATION: CDRH1 amino acid sequence 7

<400> SEQUENCE: 111

Ser Ser Ala Ile Ser
1               5

<210> SEQ ID NO 112
<211> LENGTH: 5
<212> TYPE: PRT
<213> ORGANISM: Artificial
<220> FEATURE:
<223> OTHER INFORMATION: CDRH1 amino acid sequence 8

<400> SEQUENCE: 112

Asn Tyr Ala Ile Ser
1               5

<210> SEQ ID NO 113
<211> LENGTH: 5
<212> TYPE: PRT
<213> ORGANISM: Artificial
<220> FEATURE:
<223> OTHER INFORMATION: CDRH1 amino acid sequence 9

<400> SEQUENCE: 113

Glu Tyr Ala Ile His
1               5

<210> SEQ ID NO 114
<211> LENGTH: 5
<212> TYPE: PRT
<213> ORGANISM: Artificial
<220> FEATURE:
<223> OTHER INFORMATION: CDRH1 amino acid sequence 10

<400> SEQUENCE: 114

Leu Tyr Ala Ile Ser
1               5

<210> SEQ ID NO 115
<211> LENGTH: 5
<212> TYPE: PRT
<213> ORGANISM: Artificial
<220> FEATURE:
<223> OTHER INFORMATION: CDRH1 amino acid sequence 11

<400> SEQUENCE: 115
```

```
Glu Tyr Ala Ile Ser
1               5

<210> SEQ ID NO 116
<211> LENGTH: 5
<212> TYPE: PRT
<213> ORGANISM: Artificial
<220> FEATURE:
<223> OTHER INFORMATION: CDRH1 amino acid sequence 12

<400> SEQUENCE: 116

Ser Tyr Ala Met His
1               5

<210> SEQ ID NO 117
<211> LENGTH: 5
<212> TYPE: PRT
<213> ORGANISM: Artificial
<220> FEATURE:
<223> OTHER INFORMATION: CDRH1 amino acid sequence 13

<400> SEQUENCE: 117

Gln Tyr Ala Ile His
1               5

<210> SEQ ID NO 118
<211> LENGTH: 5
<212> TYPE: PRT
<213> ORGANISM: Artificial
<220> FEATURE:
<223> OTHER INFORMATION: CDRH1 amino acid sequence 14

<400> SEQUENCE: 118

Arg Tyr Tyr Trp Ser
1               5

<210> SEQ ID NO 119
<211> LENGTH: 5
<212> TYPE: PRT
<213> ORGANISM: Artificial
<220> FEATURE:
<223> OTHER INFORMATION: CDRH1 amino acid sequence 15

<400> SEQUENCE: 119

Ser Tyr Pro Met His
1               5

<210> SEQ ID NO 120
<211> LENGTH: 5
<212> TYPE: PRT
<213> ORGANISM: Artificial
<220> FEATURE:
<223> OTHER INFORMATION: CDRH1 amino acid sequence 16

<400> SEQUENCE: 120

Arg Ala Ala Met His
1               5

<210> SEQ ID NO 121
<211> LENGTH: 5
<212> TYPE: PRT
<213> ORGANISM: Artificial
<220> FEATURE:
<223> OTHER INFORMATION: CDRH1 amino acid sequence 17

<400> SEQUENCE: 121
```

Thr Tyr Arg Met His
1               5

<210> SEQ ID NO 122
<211> LENGTH: 5
<212> TYPE: PRT
<213> ORGANISM: Artificial
<220> FEATURE:
<223> OTHER INFORMATION: CDRH1 amino acid sequence 18

<400> SEQUENCE: 122

Ala Tyr Gln Met His
1               5

<210> SEQ ID NO 123
<211> LENGTH: 5
<212> TYPE: PRT
<213> ORGANISM: Artificial
<220> FEATURE:
<223> OTHER INFORMATION: CDRH1 amino acid sequence 19

<400> SEQUENCE: 123

Arg Tyr Asn Met His
1               5

<210> SEQ ID NO 124
<211> LENGTH: 5
<212> TYPE: PRT
<213> ORGANISM: Artificial
<220> FEATURE:
<223> OTHER INFORMATION: CDRH1 amino acid sequence 20

<400> SEQUENCE: 124

Lys Tyr Arg Met His
1               5

<210> SEQ ID NO 125
<211> LENGTH: 5
<212> TYPE: PRT
<213> ORGANISM: Artificial
<220> FEATURE:
<223> OTHER INFORMATION: CDRH1 amino acid sequence 21

<400> SEQUENCE: 125

Gly Tyr Pro Ile Ser
1               5

<210> SEQ ID NO 126
<211> LENGTH: 17
<212> TYPE: PRT
<213> ORGANISM: Artificial
<220> FEATURE:
<223> OTHER INFORMATION: CDRH2 amino acid sequence 1

<400> SEQUENCE: 126

Gly Ile Ile Pro Ile Phe Gly Thr Ala Ser Tyr Ala Gln Lys Phe Gln
1               5                   10                  15

Gly

<210> SEQ ID NO 127
<211> LENGTH: 17
<212> TYPE: PRT
<213> ORGANISM: Artificial
<220> FEATURE:
<223> OTHER INFORMATION: CDRH2 amino acid sequence 2

<400> SEQUENCE: 127

```
Gly Ile Ile Pro Ile Met Gly Thr Ala Arg Tyr Ala Gln Lys Phe Gln
1               5                   10                  15

Gly

<210> SEQ ID NO 128
<211> LENGTH: 17
<212> TYPE: PRT
<213> ORGANISM: Artificial
<220> FEATURE:
<223> OTHER INFORMATION: CDRH2 amino acid sequence 3

<400> SEQUENCE: 128

Gly Ile Ile Pro Ile Phe Gly Arg Ala Arg Tyr Ala Gln Lys Phe Gln
1               5                   10                  15

Gly

<210> SEQ ID NO 129
<211> LENGTH: 17
<212> TYPE: PRT
<213> ORGANISM: Artificial
<220> FEATURE:
<223> OTHER INFORMATION: CDRH2 amino acid sequence 4

<400> SEQUENCE: 129

Gly Ile Ile Pro Ile Phe Gly Arg Gly Lys Tyr Ala Gln Lys Phe Gln
1               5                   10                  15

Gly

<210> SEQ ID NO 130
<211> LENGTH: 17
<212> TYPE: PRT
<213> ORGANISM: Artificial
<220> FEATURE:
<223> OTHER INFORMATION: CDRH2 amino acid sequence 5

<400> SEQUENCE: 130

Gly Ile Leu Pro Ile Phe Gly Arg Ala Asn Tyr Ala Gln Lys Phe Gln
1               5                   10                  15

Gly

<210> SEQ ID NO 131
<211> LENGTH: 17
<212> TYPE: PRT
<213> ORGANISM: Artificial
<220> FEATURE:
<223> OTHER INFORMATION: CDRH2 amino acid sequence 6

<400> SEQUENCE: 131

Gly Ile Ile Pro Ile Phe Gly Arg Ala Asn Tyr Ala Gln Lys Phe Gln
1               5                   10                  15

Gly

<210> SEQ ID NO 132
<211> LENGTH: 17
<212> TYPE: PRT
<213> ORGANISM: Artificial
<220> FEATURE:
<223> OTHER INFORMATION: CDRH2 amino acid sequence 7

<400> SEQUENCE: 132

Gly Ile Ile Pro Ala Leu Gly Thr Ala Asn Tyr Ala Gln Lys Phe Gln
1               5                   10                  15
```

Gly

<210> SEQ ID NO 133
<211> LENGTH: 17
<212> TYPE: PRT
<213> ORGANISM: Artificial
<220> FEATURE:
<223> OTHER INFORMATION: CDRH2 amino acid sequence 8

<400> SEQUENCE: 133

Asn Ile Ile Pro Ile Phe Gly Thr Ala Gly Tyr Ala Gln Lys Phe Gln
1               5                   10                  15

Gly

<210> SEQ ID NO 134
<211> LENGTH: 17
<212> TYPE: PRT
<213> ORGANISM: Artificial
<220> FEATURE:
<223> OTHER INFORMATION: CDRH2 amino acid sequence 9

<400> SEQUENCE: 134

Gly Ile Ile Pro Gln Leu Gly Thr Ala Asn Tyr Ala Gln Lys Phe Gln
1               5                   10                  15

Gly

<210> SEQ ID NO 135
<211> LENGTH: 17
<212> TYPE: PRT
<213> ORGANISM: Artificial
<220> FEATURE:
<223> OTHER INFORMATION: CDRH2 amino acid sequence 10

<400> SEQUENCE: 135

Gly Ile Ile Pro Val Phe Gly Thr Ala Asn Tyr Ala Gln Lys Phe Gln
1               5                   10                  15

Gly

<210> SEQ ID NO 136
<211> LENGTH: 17
<212> TYPE: PRT
<213> ORGANISM: Artificial
<220> FEATURE:
<223> OTHER INFORMATION: CDRH2 amino acid sequence 11

<400> SEQUENCE: 136

Gly Ile Ile Pro Ile Phe Gly Thr Ala Trp Tyr Ala Gln Lys Phe Gln
1               5                   10                  15

Gly

<210> SEQ ID NO 137
<211> LENGTH: 17
<212> TYPE: PRT
<213> ORGANISM: Artificial
<220> FEATURE:
<223> OTHER INFORMATION: CDRH2 amino acid sequence 12

<400> SEQUENCE: 137

Val Ile Ile Pro Ile Phe Gly Lys Ala Asn Tyr Ala Gln Lys Phe Gln
1               5                   10                  15

Gly

<210> SEQ ID NO 138

```
<211> LENGTH: 16
<212> TYPE: PRT
<213> ORGANISM: Artificial
<220> FEATURE:
<223> OTHER INFORMATION: CDRH2 amino acid sequence 13

<400> SEQUENCE: 138

Glu Ile Asp Gly Trp Gly Ser Thr Asn Tyr Asn Pro Ser Leu Lys Ser
1               5                   10                  15

<210> SEQ ID NO 139
<211> LENGTH: 17
<212> TYPE: PRT
<213> ORGANISM: Artificial
<220> FEATURE:
<223> OTHER INFORMATION: CDRH2 amino acid sequence 14

<400> SEQUENCE: 139

Ile Ile Asn Pro Ser Gly Gly Phe Thr Ser Tyr Ala Gln Lys Phe Gln
1               5                   10                  15

Gly

<210> SEQ ID NO 140
<211> LENGTH: 17
<212> TYPE: PRT
<213> ORGANISM: Artificial
<220> FEATURE:
<223> OTHER INFORMATION: CDRH2 amino acid sequence 15

<400> SEQUENCE: 140

Ile Ile Asn Pro Ala Gly Gly Tyr Thr Ser Tyr Ala Gln Lys Phe Gln
1               5                   10                  15

Gly

<210> SEQ ID NO 141
<211> LENGTH: 17
<212> TYPE: PRT
<213> ORGANISM: Artificial
<220> FEATURE:
<223> OTHER INFORMATION: CDRH2 amino acid sequence 16

<400> SEQUENCE: 141

Ile Ile Asn Pro Ser Gly Gly Leu Thr Gln Tyr Ala Gln Lys Phe Gln
1               5                   10                  15

Gly

<210> SEQ ID NO 142
<211> LENGTH: 17
<212> TYPE: PRT
<213> ORGANISM: Artificial
<220> FEATURE:
<223> OTHER INFORMATION: CDRH2 amino acid sequence 17

<400> SEQUENCE: 142

Ile Ile Asn Pro Ala Gly Gly Trp Thr Ser Tyr Ala Gln Lys Phe Gln
1               5                   10                  15

Gly

<210> SEQ ID NO 143
<211> LENGTH: 17
<212> TYPE: PRT
<213> ORGANISM: Artificial
<220> FEATURE:
<223> OTHER INFORMATION: CDRH2 amino acid sequence 18
```

```
<400> SEQUENCE: 143

Trp Ile Asn Pro Ala Gly Gly Ser Thr Ser Tyr Ala Gln Lys Phe Gln
1               5                   10                  15
Gly

<210> SEQ ID NO 144
<211> LENGTH: 17
<212> TYPE: PRT
<213> ORGANISM: Artificial
<220> FEATURE:
<223> OTHER INFORMATION: CDRH2 amino acid sequence 19

<400> SEQUENCE: 144

Ile Ile Asn Pro Gln Gly Gly Ser Thr Ser Tyr Ala Gln Lys Phe Gln
1               5                   10                  15
Gly

<210> SEQ ID NO 145
<211> LENGTH: 17
<212> TYPE: PRT
<213> ORGANISM: Artificial
<220> FEATURE:
<223> OTHER INFORMATION: CDRH2 amino acid sequence 20

<400> SEQUENCE: 145

Gly Ile Ile Pro Ala Phe Gly Thr Ala Gln Tyr Ala Gln Lys Phe Gln
1               5                   10                  15
Gly

<210> SEQ ID NO 146
<211> LENGTH: 17
<212> TYPE: PRT
<213> ORGANISM: Artificial
<220> FEATURE:
<223> OTHER INFORMATION: CDRH2 amino acid sequence 21

<400> SEQUENCE: 146

Gly Ile Val Pro Val Phe Gly Thr Ala Lys Tyr Ala Gln Lys Phe Gln
1               5                   10                  15
Gly

<210> SEQ ID NO 147
<211> LENGTH: 13
<212> TYPE: PRT
<213> ORGANISM: Artificial
<220> FEATURE:
<223> OTHER INFORMATION: CDRH3 amino acid sequence 1

<400> SEQUENCE: 147

Gly Ala Gly Tyr Tyr Gly Asp Lys Asp Pro Met Asp Val
1               5                   10

<210> SEQ ID NO 148
<211> LENGTH: 9
<212> TYPE: PRT
<213> ORGANISM: Artificial
<220> FEATURE:
<223> OTHER INFORMATION: CDRH3 amino acid sequence 2

<400> SEQUENCE: 148

Leu Leu Gly Glu Ser Gly Met Asp Val
1               5
```

```
<210> SEQ ID NO 149
<211> LENGTH: 18
<212> TYPE: PRT
<213> ORGANISM: Artificial
<220> FEATURE:
<223> OTHER INFORMATION: CDRH3 amino acid sequence 3

<400> SEQUENCE: 149

Gly Gly Ser Val Asp Phe Trp Ser Gly Ser Asp Tyr Tyr Tyr Met
1               5                   10                  15

Asp Val

<210> SEQ ID NO 150
<211> LENGTH: 14
<212> TYPE: PRT
<213> ORGANISM: Artificial
<220> FEATURE:
<223> OTHER INFORMATION: CDRH3 amino acid sequence 4

<400> SEQUENCE: 150

Glu Thr Ala Tyr Tyr Thr Thr Lys Gly Asn Trp Phe Asp Pro
1               5                   10

<210> SEQ ID NO 151
<211> LENGTH: 5
<212> TYPE: PRT
<213> ORGANISM: Artificial
<220> FEATURE:
<223> OTHER INFORMATION: PD-1 antagonist CDRH1

<400> SEQUENCE: 151

Ser Tyr Asp Met Ser
1               5

<210> SEQ ID NO 152
<211> LENGTH: 17
<212> TYPE: PRT
<213> ORGANISM: Artificial
<220> FEATURE:
<223> OTHER INFORMATION: PD-1 antagonist CDRH2

<400> SEQUENCE: 152

Thr Ile Ser Gly Gly Gly Ser Tyr Thr Tyr Tyr Gln Asp Ser Val Lys
1               5                   10                  15

Gly

<210> SEQ ID NO 153
<211> LENGTH: 7
<212> TYPE: PRT
<213> ORGANISM: Artificial
<220> FEATURE:
<223> OTHER INFORMATION: PD-1 antagonist CDRH3

<400> SEQUENCE: 153

Pro Tyr Tyr Ala Met Asp Tyr
1               5

<210> SEQ ID NO 154
<211> LENGTH: 11
<212> TYPE: PRT
<213> ORGANISM: Artificial
<220> FEATURE:
<223> OTHER INFORMATION: PD-1 antagonist CDRL1

<400> SEQUENCE: 154

Lys Ala Ser Gln Asp Val Gly Thr Ala Val Ala
```

<210> SEQ ID NO 155
<211> LENGTH: 7
<212> TYPE: PRT
<213> ORGANISM: Artificial
<220> FEATURE:
<223> OTHER INFORMATION: PD-1 antagonist CDRL2

<400> SEQUENCE: 155

Trp Ala Ser Thr Leu His Thr
1               5

<210> SEQ ID NO 156
<211> LENGTH: 9
<212> TYPE: PRT
<213> ORGANISM: Artificial
<220> FEATURE:
<223> OTHER INFORMATION: PD-1 antagonist CDRH3

<400> SEQUENCE: 156

Gln His Tyr Ser Ser Tyr Pro Trp Thr
1               5

<210> SEQ ID NO 157
<211> LENGTH: 9
<212> TYPE: PRT
<213> ORGANISM: Artificial
<220> FEATURE:
<223> OTHER INFORMATION: PD-1 antagonist alternative CDRL3

<400> SEQUENCE: 157

Gln His Tyr Asn Ser Tyr Pro Trp Thr
1               5

<210> SEQ ID NO 158
<211> LENGTH: 116
<212> TYPE: PRT
<213> ORGANISM: Artificial
<220> FEATURE:
<223> OTHER INFORMATION: PD-1 antagonist heavy chain variable region

<400> SEQUENCE: 158

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Gly Gly Gly Ser Tyr Thr Tyr Tyr Gln Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Tyr Ala Met Asp Tyr Trp Gly Gln Gly Thr Thr Val
            100                 105                 110

Thr Val Ser Ser
        115

<210> SEQ ID NO 159
<211> LENGTH: 107
<212> TYPE: PRT

```
<213> ORGANISM: Artificial
<220> FEATURE:
<223> OTHER INFORMATION: PD-1 antagonist light chain variable region

<400> SEQUENCE: 159

Asp Ile Gln Leu Thr Gln Ser Pro Ser Phe Leu Ser Ala Tyr Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Leu His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Tyr Ser Ser Tyr Pro Trp
                85                  90                  95

Thr Phe Gly Gln Gly Thr Lys Leu Glu Ile Lys
            100                 105

<210> SEQ ID NO 160
<211> LENGTH: 443
<212> TYPE: PRT
<213> ORGANISM: Artificial
<220> FEATURE:
<223> OTHER INFORMATION: PD-1 antagonist monoclonal antibody heavy chain

<400> SEQUENCE: 160

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Gly Gly Gly Ser Tyr Thr Tyr Tyr Gln Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Tyr Ala Met Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220
```

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
            435                 440

<210> SEQ ID NO 161
<211> LENGTH: 214
<212> TYPE: PRT
<213> ORGANISM: Artificial
<220> FEATURE:
<223> OTHER INFORMATION: PD-1 antagonist monoclonal antibody light chain

<400> SEQUENCE: 161

Asp Ile Gln Leu Thr Gln Ser Pro Ser Phe Leu Ser Ala Tyr Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Leu His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Tyr Ser Ser Tyr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

-continued

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 162
<211> LENGTH: 443
<212> TYPE: PRT
<213> ORGANISM: Artificial
<220> FEATURE:
<223> OTHER INFORMATION: PD-1 antagonist heavy chain sequence with N380D
      modification

<400> SEQUENCE: 162

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Gly Gly Gly Ser Tyr Thr Tyr Tyr Gln Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Tyr Ala Met Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

```
Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asp Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 163
<211> LENGTH: 443
<212> TYPE: PRT
<213> ORGANISM: Artificial
<220> FEATURE:
<223> OTHER INFORMATION: PD-1 antagonist light chain sequence with N385D
      modification

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Gly Gly Gly Ser Tyr Thr Tyr Tyr Gln Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Tyr Ala Met Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
```

```
            195                 200                 205
Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asp Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 164
<211> LENGTH: 443
<212> TYPE: PRT
<213> ORGANISM: Artificial
<220> FEATURE:
<223> OTHER INFORMATION: PD-1 antagonist heavy chain sequence with N380D
      and N385D modifications

<400> SEQUENCE: 164

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Gly Gly Gly Ser Tyr Thr Tyr Tyr Gln Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Tyr Ala Met Asp Tyr Trp Gly Gln Gly Thr Thr Val
            100                 105                 110
```

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asp Gly Gln Pro Glu
370                 375                 380

Asp Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 165
<211> LENGTH: 452
<212> TYPE: PRT
<213> ORGANISM: Artificial
<220> FEATURE:
<223> OTHER INFORMATION: 42Y073-86F08-66 full length heavy chain amino
      acid sequence

<400> SEQUENCE: 165

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Val Glu Tyr
            20                  25                  30

```
Ala Ile Ser Trp Val Arg Gln Ala Pro Gly Gln Gly Leu Glu Trp Met
     35                  40                  45
Gly Gly Ile Ile Pro Ala Phe Gly Thr Ala Gln Tyr Ala Gln Lys Phe
 50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Gly Ala Gly Tyr Tyr Gly Asp Lys Asp Pro Met Asp Val Trp
                100                 105                 110
Gly Gln Gly Thr Thr Val Thr Val Ser Ser Ala Ser Thr Lys Gly Pro
                115                 120                 125
Ser Val Phe Pro Leu Ala Pro Ser Ser Lys Ser Thr Ser Gly Gly Thr
            130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
            195                 200                 205
His Lys Pro Ser Asn Thr Lys Val Asp Lys Lys Val Glu Pro Lys Ser
        210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
            355                 360                 365
Ser Leu Thr Cys Leu Val Lys Gly Phe Tyr Pro Ser Asp Ile Ala Val
        370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
```

```
Ser Pro Gly Lys
    450

<210> SEQ ID NO 166
<211> LENGTH: 213
<212> TYPE: PRT
<213> ORGANISM: Artificial
<220> FEATURE:
<223> OTHER INFORMATION: 42Y073-86F08-66 full length light chain amino
      acid sequence

<400> SEQUENCE: 166

Asp Ile Gln Leu Thr Gln Ser Pro Ser Leu Ser Ala Ser Val Gly
1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Leu His Thr Ile Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 167
<211> LENGTH: 1356
<212> TYPE: DNA
<213> ORGANISM: Artificial
<220> FEATURE:
<223> OTHER INFORMATION: 42Y073-86F08-66 full length heavy chain DNA
      sequence

<400> SEQUENCE: 167
caggtgcagc tggtgcagag cggcgcagag gtgaaaaagc ccggcagcag cgtgaaggtg      60
agctgcaagg cctccggcgg gaccttcgtg gagtacgcca tcagctgggt gaggcaggct     120
cccggacagg gcctggagtg gatgggcggc atcatcccg ccttcggcac cgcccagtac      180
gcccagaagt tccagggaag ggtcaccatc accgccgacg agagcaccag caccgcctac     240
atggaactca gcagcctgag gagcgaggac accgccgtgt actattgcgc caggggagcc     300
ggctactacg gcgacaagga ccccatggac gtgtggggcc agggcaccac cgtgactgtg     360
```

| | |
|---|---|
| agcagcgcca gcaccaaggg ccccagcgtg ttccccctgg cccccagcag caagagcacc | 420 |
| agcggcggca cagccgccct gggctgcctg gtgaaggact acttccccga gcccgtgacc | 480 |
| gtgtcctgga acagcggagc cctgaccagc ggcgtgcaca ccttccccgc cgtgctgcag | 540 |
| agcagcggcc tgtacagcct gagcagcgtg gtgaccgtgc ccagcagcag cctgggcacc | 600 |
| cagacctaca tctgtaacgt gaaccacaag cccagcaaca ccaaggtgga caagaaggtg | 660 |
| gagcccaaga gctgtgacaa gacccacacc tgcccccct gccctgcccc cgagctgctg | 720 |
| ggaggcccca gcgtgttcct gttcccccc aagcctaagg acaccctgat gatcagcaga | 780 |
| accccccgagg tgacctgtgt ggtggtggat gtgagccacg aggaccctga ggtgaagttc | 840 |
| aactggtacg tggacggcgt ggaggtgcac aatgccaaga ccaagcccag ggaggagcag | 900 |
| tacaacagca cctaccgggt ggtgtccgtg ctgaccgtgc tgcaccagga ttggctgaac | 960 |
| ggcaaggagt acaagtgtaa ggtgtccaac aaggccctgc ctgcccctat cgagaaaacc | 1020 |
| atcagcaagg ccaagggcca gccagagag ccccaggtgt acaccctgcc cctagcaga | 1080 |
| gatgagctga ccaagaacca ggtgtccctg acctgcctgg tgaagggctt ctaccccagc | 1140 |
| gacatcgccg tggagtggga gagcaacggc cagcccgaga caactacaa gaccacccc | 1200 |
| cctgtgctgg acagcgatgg cagcttcttc ctgtacagca gctgaccgt ggacaagagc | 1260 |
| agatggcagc agggcaacgt gttcagctgc tccgtgatgc acgaggccct gcacaatcac | 1320 |
| tacacccaga gagcctgag cctgtcccct ggcaag | 1356 |

<210> SEQ ID NO 168
<211> LENGTH: 639
<212> TYPE: DNA
<213> ORGANISM: Artificial
<220> FEATURE:
<223> OTHER INFORMATION: 42Y073-86F08-66 full length light chain DNA
      sequence

<400> SEQUENCE: 168

| | |
|---|---|
| gacatccagc tgacccagag ccctagcagc ctgagcgcca gcgtgggaga cagggtgacc | 60 |
| atcacctgca gggccagcca gtccatcagc agctacctga actggtacca gcagaagccc | 120 |
| ggcaaggccc ccaagctgct gatctacgcc gcaagctcac tgcagagcgg cgtgccctct | 180 |
| aggtttagcg gcagcggcag cggcaccgac ttcaccctga ccatcagcag cctccagccc | 240 |
| gaggacttcg ccacctacta ctgccagcag gtgctgcaca ccatcacttt cggcggcggc | 300 |
| accaaggtgg agattaagcg tacggtggcc gccccagcg tgttcatctt cccccccagc | 360 |
| gatgagcagc tgaagagcgg caccgccagc gtggtgtgtc tgctgaacaa cttctacccc | 420 |
| cgggaggcca aggtgcagtg gaaggtggac aatgccctgc agagcggcaa cagccaggag | 480 |
| agcgtgaccg agcaggacag caaggactcc acctacagcc tgagcagcac cctgaccctg | 540 |
| agcaaggccg actacgagaa gcacaaggtg tacgcctgtg aggtgaccca ccagggcctg | 600 |
| tccagccccg tgaccaagag cttcaaccgg ggcgagtgc | 639 |

<210> SEQ ID NO 169
<211> LENGTH: 213
<212> TYPE: PRT
<213> ORGANISM: Artificial
<220> FEATURE:
<223> OTHER INFORMATION: 42Y073-86F08-16 full length light chain amino
      acid sequence

<400> SEQUENCE: 169

Asp Ile Gln Leu Thr Gln Ser Pro Ser Ser Leu Ser Ala Ser Val Gly

```
            1               5                  10                 15
        Asp Arg Val Thr Ile Thr Cys Arg Ala Ser Gln Ser Ile Ser Ser Tyr
                        20                 25                 30

Leu Asn Trp Tyr Gln Gln Lys Pro Gly Lys Ala Pro Lys Leu Leu Ile
                    35                 40                 45

Tyr Ala Ala Ser Ser Leu Gln Ser Gly Val Pro Ser Arg Phe Ser Gly
                50                 55                 60

Ser Gly Ser Gly Thr Asp Phe Thr Leu Thr Ile Ser Ser Leu Gln Pro
        65                 70                 75                 80

Glu Asp Phe Ala Thr Tyr Tyr Cys Gln Gln Val Leu His Thr Ile Thr
                        85                 90                 95

Phe Gly Gly Gly Thr Lys Val Glu Ile Lys Arg Thr Val Ala Ala Pro
                        100                105                110

Ser Val Phe Ile Phe Pro Pro Ser Asp Glu Gln Leu Lys Ser Gly Thr
                        115                120                125

Ala Ser Val Val Cys Leu Leu Asn Asn Phe Tyr Pro Arg Glu Ala Lys
        130                135                140

Val Gln Trp Lys Val Asp Asn Ala Leu Gln Ser Gly Asn Ser Gln Glu
        145                150                155                160

Ser Val Thr Glu Gln Asp Ser Lys Asp Ser Thr Tyr Ser Leu Ser Ser
                        165                170                175

Thr Leu Thr Leu Ser Lys Ala Asp Tyr Glu Lys His Lys Val Tyr Ala
                        180                185                190

Cys Glu Val Thr His Gln Gly Leu Ser Ser Pro Val Thr Lys Ser Phe
                        195                200                205

Asn Arg Gly Glu Cys
        210

<210> SEQ ID NO 170
<211> LENGTH: 452
<212> TYPE: PRT
<213> ORGANISM: Artificial
<220> FEATURE:
<223> OTHER INFORMATION: 42Y073-86F08-16 full length heavy chain amino
      acid sequence

<400> SEQUENCE: 170

Gln Val Gln Leu Val Gln Ser Gly Ala Glu Val Lys Lys Pro Gly Ser
        1               5                  10                 15

Ser Val Lys Val Ser Cys Lys Ala Ser Gly Gly Thr Phe Asn Glu Tyr
                        20                 25                 30

Ala Ile Ser Trp Val Arg Gln Ala Pro Gly Gln Gly Leu Glu Trp Met
                    35                 40                 45

Gly Gly Ile Val Pro Val Phe Gly Thr Ala Lys Tyr Ala Gln Lys Phe
                50                 55                 60

Gln Gly Arg Val Thr Ile Thr Ala Asp Glu Ser Thr Ser Thr Ala Tyr
        65                 70                 75                 80

Met Glu Leu Ser Ser Leu Arg Ser Glu Asp Thr Ala Val Tyr Tyr Cys
                        85                 90                 95

Ala Arg Gly Ala Gly Tyr Tyr Gly Asp Lys Asp Pro Met Asp Val Trp
                        100                105                110

Gly Gln Gly Thr Thr Val Thr Val Ser Ser Ala Ser Thr Lys Gly Pro
                        115                120                125

Ser Val Phe Pro Leu Ala Pro Ser Ser Lys Ser Thr Ser Gly Gly Thr
        130                135                140
```

-continued

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 171
<211> LENGTH: 639
<212> TYPE: DNA
<213> ORGANISM: Artificial
<220> FEATURE:
<223> OTHER INFORMATION: 42Y073-86F08-16 full length light chain DNA
      sequence

<400> SEQUENCE: 171
gacatccagc tgacccagag ccctagcagc ctgagcgcca gcgtgggaga cagggtgacc    60
atcacctgca gggccagcca gtccatcagc agctacctga actggtacca gcagaagccc   120
ggcaaggccc ccaagctgct gatctacgcc gcaagctcac tgcagagcgg cgtgccctct   180
aggtttagcg gcagcggcag cggcaccgac ttcaccctga ccatcagcag cctccagccc   240

```
gaggacttcg ccacctacta ctgccagcag gtgctgcaca ccatcacttt cggcggcggc    300
accaaggtgg agattaagcg tacggtggcc gcccccagcg tgttcatctt ccccccagc     360 gatgagcagc tgaagagcgg caccgccagc gtggtgtgtc tgctgaacaa cttctacccc    420
cgggaggcca aggtgcagtg gaaggtggac aatgccctgc agagcggcaa cagccaggag    480
agcgtgaccg agcaggacag caaggactcc acctacagcc tgagcagcac cctgaccctg    540
agcaaggccg actacgagaa gcacaaggtg tacgcctgtg aggtgaccca ccagggcctg    600
tccagccccg tgaccaagag cttcaaccgg ggcgagtgc                           639

<210> SEQ ID NO 172
<211> LENGTH: 1356
<212> TYPE: DNA
<213> ORGANISM: Artificial
<220> FEATURE:
<223> OTHER INFORMATION: 42Y073-86F08-16  full length heavy chain DNA
      sequence

<400> SEQUENCE: 172
caggtgcagc tggtgcagag cggcgccgag gtgaaaaagc ccggcagcag cgtgaaggtg    60
agctgcaagg cctccggcgg gaccttcaac gagtacgcca tcagctgggt gaggcaggct    120
cccggacagg gcctggagtg gatgggcggc atcgtgcccg tgttcggcac cgccaagtac    180
gcccagaagt tccagggaag ggtcaccatc accgccgacg agagcaccag caccgcctac    240
atggaactca gcagcctgag gagcgaggac accgccgtgt actattgcgc caggggcgcc    300
ggctactacg gcgacaagga ccccatggac gtgtggggcc agggcaccac cgtgactgtg    360
agcagcgcca gcaccaaggg ccccagcgtg ttccccctgg cccccagcag caagagcacc    420
agcggcggca cagccgccct gggctgcctg gtgaaggact acttccccga gcccgtgacc    480
gtgtcctgga cagcggagc cctgaccagc ggcgtgcaca ccttcccgc cgtgctgcag    540 agcagcggcc tgtacagcct gagcagcgtg gtgaccgtgc ccagcagcag cctgggcacc    600
cagacctaca tctgtaacgt gaaccacaag cccagcaaca ccaaggtgga caagaaggtg    660
gagcccaaga gctgtgacaa gacccacacc tgccccccct gccctgcccc cgagctgctg    720
ggaggcccca gcgtgttcct gttccccccc aagcctaagg acaccctgat gatcagcaga    780
accccccagg tgacctgtgt ggtggtggat gtgagccacg aggaccctga ggtgaagttc    840
aactggtacg tggacggcgt ggaggtgcac aatgccaaga ccaagccagg gaggagcag    900 tacaacagca cctaccgggt ggtgtccgtg ctgaccgtgc tgcaccagga ttggctgaac    960
ggcaaggagt acaagtgtaa ggtgtccaac aaggccctgc ctgcccctat cgagaaaacc    1020
atcagcaagg ccaagggcca gcccagagag ccccaggtgt acaccctgcc cctagcaga    1080 gatgagctga ccaagaacca ggtgtccctg acctgcctgg tgaagggctt ctaccccagc    1140
gacatcgccg tggagtggga gagcaacggc cagcccgaga caactacaa gaccacccc     1200 cctgtgctgg acagcgatgg cagcttcttc ctgtacagca agctgaccgt ggacaagagc    1260
agatggcagc agggcaacgt gttcagctgc tccgtgatgc acgaggccct gcacaatcac    1320
tacacccaga agagcctgag cctgtcccct ggcaag                              1356

<210> SEQ ID NO 173
<211> LENGTH: 214
<212> TYPE: PRT
<213> ORGANISM: Artificial
<220> FEATURE:
<223> OTHER INFORMATION: 42Y073-86F04-23 full length light chain amino
      acid sequence
```

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Tyr Phe Ser Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 174
<211> LENGTH: 448
<212> TYPE: PRT
<213> ORGANISM: Artificial
<220> FEATURE:
<223> OTHER INFORMATION: 42Y073-86F04-23 full length Heavy chain amino
      acid sequence

<400> SEQUENCE: 174

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Gly Tyr
            20                  25                  30

Pro Ile Ser Trp Val Arg Gln Ala Pro Gly Gln Gly Leu Glu Trp Met
        35                  40                  45

Gly Gly Ile Ile Pro Ile Met Gly Thr Ala Arg Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Gly Glu Ser Gly Met Asp Val Trp Gly Gln Gly Thr
            100                 105                 110

Thr Val Thr Val Ser Ser Ala Ser Thr Lys Gly Pro Ser Val Phe Pro
        115                 120                 125

```
Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 175
<211> LENGTH: 642
<212> TYPE: DNA
<213> ORGANISM: Artificial
<220> FEATURE:
<223> OTHER INFORMATION: 42Y073-86F04-23 full length Light chain DNA
      sequence

<400> SEQUENCE: 175
gacatccaga tgacccagag ccctagcagc ctgagcgcca gcgtgggaga cagggtgacc    60
atcacctgca gggccagcca gtccatcagc agctacctga actggtacca gcagaagccc   120
ggcaaggccc ccaagctgct gatctacgcc gcaagctcac tgcagagcgg cgtgccctct   180
aggtttagcg gcagcggcag cggcaccgac ttcaccctga ccatcagcag cctccagccc   240
```

```
gaggacttcg ccacctacta ctgccagcag ccctacttca gccccccac tttcggcggc      300 ggcaccaagg tggagattaa gcgtacggtg gccgccccca gcgtgttcat cttccccccc      360
agcgatgagc agctgaagag cggcaccgcc agcgtggtgt gtctgctgaa caacttctac      420
cccccgggag ccaaggtgca gtggaaggtg gacaatgccc tgcagagcgg caacagccag      480
gagagcgtga ccgagcagga cagcaaggac tccacctaca gcctgagcag caccctgacc      540
ctgagcaagg ccgactacga aagcacaag gtgtacgcct gtgaggtgac caccagggc      600 ctgtccagcc ccgtgaccaa gagcttcaac cggggcgagt gc                        642

<210> SEQ ID NO 176
<211> LENGTH: 1344
<212> TYPE: DNA
<213> ORGANISM: Artificial
<220> FEATURE:
<223> OTHER INFORMATION: 42Y073-86F04-23  full length Heavy chain DNA
      sequence

<400> SEQUENCE: 176
caggtgcagc tggtgcagag cggcgccgag gtgaaaaagc ccggcagcag cgtgaaggtg      60
agctgcaagg cctccggcgg gaccttcagc ggctacccca tcagctgggt gaggcaggct      120
cccggacagg gcctggagtg gatgggcggc atcatcccca ttatgggcac cgccaggtac      180
gcccagaagt tccagggaag ggtcaccatc accgccgacg agagcaccag caccgcctac      240
atggaactca gcagcctgag gagcgaggac accgccgtgt actattgcgc caggctgctg      300
ggcgagagcg gcatggacgt gtggggccag ggcaccaccg tgactgtgag cagcgccagc      360
accaagggcc ccagcgtgtt ccccctggcc ccagcagca agagcaccag cggcggcaca      420
gccgccctgg gctgcctggt gaaggactac ttccccgagc ccgtgaccgt gtcctggaac      480
agcggagccc tgaccagcgg cgtgcacacc ttccccgccg tgctgcagag cagcggcctg      540
tacagcctga gcagcgtggt gaccgtgccc agcagcagcc tgggcaccca gacctacatc      600
tgtaacgtga accacaagcc cagcaacacc aaggtggaca gaaggtgga gcccaagagc      660 tgtgacaaga cccacacctg cccccccctgc cctgccccg agctgctggg aggccccagc      720
gtgttcctgt tccccccaa gcctaaggac accctgatga tcagcagaac ccccgaggtg      780
acctgtgtgg tggtggatgt gagccacgag gaccctgagg tgaagttcaa ctggtacgtg      840
gacggcgtgg aggtgcacaa tgccaagacc aagcccaggg aggagcagta caacagcacc      900
taccgggtgg tgtccgtgct gaccgtgctg caccaggatt ggctgaacgg caaggagtac      960
aagtgtaagg tgtccaacaa ggccctgcct gcccctatcg agaaaaccat cagcaaggcc      1020
aagggccagc ccagagagcc ccaggtgtac accctgcccc ctagcagaga tgagctgacc      1080
aagaaccagg tgtccctgac ctgcctggtg aagggcttct accccagcga catcgccgtg      1140
gagtgggaga gcaacggcca gcccgagaac aactacaaga ccacccccc tgtgctggac      1200 agcgatggca gcttcttcct gtacagcaag ctgaccgtgg acaagagcag atggcagcag      1260
ggcaacgtgt tcagctgctc cgtgatgcac gaggccctgc acaatcacta cacccagaag      1320
agcctgagcc tgtcccctgg caag                                             1344

<210> SEQ ID NO 177
<211> LENGTH: 564
<212> TYPE: PRT
<213> ORGANISM: Artificial Sequence
<220> FEATURE:
<223> OTHER INFORMATION: CD155-fc amino acid sequence used in examples
```

<400> SEQUENCE: 177

Trp Pro Pro Pro Gly Thr Gly Asp Val Val Gln Ala Pro Thr Gln
1               5                   10                  15

Val Pro Gly Phe Leu Gly Asp Ser Val Thr Leu Pro Cys Tyr Leu Gln
            20                  25                  30

Val Pro Asn Met Glu Val Thr His Val Ser Gln Leu Thr Trp Ala Arg
            35                  40                  45

His Gly Glu Ser Gly Ser Met Ala Val Phe His Gln Thr Gln Gly Pro
50                  55                  60

Ser Tyr Ser Glu Ser Lys Arg Leu Glu Phe Val Ala Ala Arg Leu Gly
65                  70                  75                  80

Ala Glu Leu Arg Asn Ala Ser Leu Arg Met Phe Gly Leu Arg Val Glu
            85                  90                  95

Asp Glu Gly Asn Tyr Thr Cys Leu Phe Val Thr Phe Pro Gln Gly Ser
            100                 105                 110

Arg Ser Val Asp Ile Trp Leu Arg Val Leu Ala Lys Pro Gln Asn Thr
            115                 120                 125

Ala Glu Val Gln Lys Val Gln Leu Thr Gly Glu Pro Val Pro Met Ala
130                 135                 140

Arg Cys Val Ser Thr Gly Gly Arg Pro Pro Ala Gln Ile Thr Trp His
145                 150                 155                 160

Ser Asp Leu Gly Gly Met Pro Asn Thr Ser Gln Val Pro Gly Phe Leu
            165                 170                 175

Ser Gly Thr Val Thr Val Thr Ser Leu Trp Ile Leu Val Pro Ser Ser
            180                 185                 190

Gln Val Asp Gly Lys Asn Val Thr Cys Lys Val Glu His Glu Ser Phe
            195                 200                 205

Glu Lys Pro Gln Leu Leu Thr Val Asn Leu Thr Val Tyr Tyr Pro Pro
210                 215                 220

Glu Val Ser Ile Ser Gly Tyr Asp Asn Asn Trp Tyr Leu Gly Gln Asn
225                 230                 235                 240

Glu Ala Thr Leu Thr Cys Asp Ala Arg Ser Asn Pro Glu Pro Thr Gly
            245                 250                 255

Tyr Asn Trp Ser Thr Thr Met Gly Pro Leu Pro Pro Phe Ala Val Ala
            260                 265                 270

Gln Gly Ala Gln Leu Leu Ile Arg Pro Val Asp Lys Pro Ile Asn Thr
            275                 280                 285

Thr Leu Ile Cys Asn Val Thr Asn Ala Leu Gly Ala Arg Gln Ala Glu
290                 295                 300

Leu Thr Val Gln Val Lys Glu Gly Pro Pro Ser Glu His Ser Gly Ile
305                 310                 315                 320

Ser Arg Asn Ser Gly Glu Asn Leu Tyr Phe Gln Gly Asp Pro Lys Ser
            325                 330                 335

Cys Asp Lys Thr His Thr Cys Pro Pro Cys Pro Ala Pro Glu Leu Leu
            340                 345                 350

Gly Gly Pro Ser Val Phe Leu Phe Pro Pro Lys Pro Lys Asp Thr Leu
            355                 360                 365

Met Ile Ser Arg Thr Pro Glu Val Thr Cys Val Val Val Asp Val Ser
            370                 375                 380

His Glu Asp Pro Glu Val Lys Phe Asn Trp Tyr Val Asp Gly Val Glu
385                 390                 395                 400

Val His Asn Ala Lys Thr Lys Pro Arg Glu Glu Gln Tyr Asn Ser Thr

```
            405                 410                 415
Tyr Arg Val Val Ser Val Leu Thr Val Leu His Gln Asp Trp Leu Asn
            420                 425                 430

Gly Lys Glu Tyr Lys Cys Lys Val Ser Asn Lys Ala Leu Pro Ala Pro
        435                 440                 445

Ile Glu Lys Thr Ile Ser Lys Ala Lys Gly Gln Pro Arg Glu Pro Gln
    450                 455                 460

Val Tyr Thr Leu Pro Pro Ser Arg Asp Glu Leu Thr Lys Asn Gln Val
465                 470                 475                 480

Ser Leu Thr Cys Leu Val Lys Gly Phe Tyr Pro Ser Asp Ile Ala Val
            485                 490                 495

Glu Trp Glu Ser Asn Gly Gln Pro Glu Asn Asn Tyr Lys Thr Thr Pro
        500                 505                 510

Pro Val Leu Asp Ser Asp Gly Ser Phe Phe Leu Tyr Ser Lys Leu Thr
    515                 520                 525

Val Asp Lys Ser Arg Trp Gln Gln Gly Asn Val Phe Ser Cys Ser Val
530                 535                 540

Met His Glu Ala Leu His Asn His Tyr Thr Gln Lys Ser Leu Ser Leu
545                 550                 555                 560

Ser Pro Gly Lys

<210> SEQ ID NO 178
<211> LENGTH: 417
<212> TYPE: PRT
<213> ORGANISM: Homo sapiens

<400> SEQUENCE: 178

Met Ala Arg Ala Met Ala Ala Trp Pro Leu Leu Leu Val Ala Leu
1               5                   10                  15

Leu Val Leu Ser Trp Pro Pro Gly Thr Gly Asp Val Val Val Gln
            20                  25                  30

Ala Pro Thr Gln Val Pro Gly Phe Leu Gly Asp Ser Val Thr Leu Pro
        35                  40                  45

Cys Tyr Leu Gln Val Pro Asn Met Glu Val Thr His Val Ser Gln Leu
    50                  55                  60

Thr Trp Ala Arg His Gly Glu Ser Gly Ser Met Ala Val Phe His Gln
65                  70                  75                  80

Thr Gln Gly Pro Ser Tyr Ser Glu Ser Lys Arg Leu Glu Phe Val Ala
            85                  90                  95

Ala Arg Leu Gly Ala Glu Leu Arg Asn Ala Ser Leu Arg Met Phe Gly
        100                 105                 110

Leu Arg Val Glu Asp Glu Gly Asn Tyr Thr Cys Leu Phe Val Thr Phe
    115                 120                 125

Pro Gln Gly Ser Arg Ser Val Asp Ile Trp Leu Arg Val Leu Ala Lys
130                 135                 140

Pro Gln Asn Thr Ala Glu Val Gln Lys Val Gln Leu Thr Gly Glu Pro
145                 150                 155                 160

Val Pro Met Ala Arg Cys Val Ser Thr Gly Gly Arg Pro Pro Ala Gln
            165                 170                 175

Ile Thr Trp His Ser Asp Leu Gly Gly Met Pro Asn Thr Ser Gln Val
        180                 185                 190

Pro Gly Phe Leu Ser Gly Thr Val Thr Val Thr Ser Leu Trp Ile Leu
    195                 200                 205

Val Pro Ser Ser Gln Val Asp Gly Lys Asn Val Thr Cys Lys Val Glu
```

```
            210                 215                 220
His Glu Ser Phe Glu Lys Pro Gln Leu Leu Thr Val Asn Leu Thr Val
225                 230                 235                 240

Tyr Tyr Pro Pro Glu Val Ser Ile Ser Gly Tyr Asp Asn Asn Trp Tyr
                245                 250                 255

Leu Gly Gln Asn Glu Ala Thr Leu Thr Cys Asp Ala Arg Ser Asn Pro
                260                 265                 270

Glu Pro Thr Gly Tyr Asn Trp Ser Thr Met Gly Pro Leu Pro Pro
                275                 280                 285

Phe Ala Val Ala Gln Gly Ala Gln Leu Leu Ile Arg Pro Val Asp Lys
                290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Glu Gly Pro Pro Ser Glu
                325                 330                 335

His Ser Gly Ile Ser Arg Asn Ala Ile Ile Phe Leu Val Leu Gly Ile
                340                 345                 350

Leu Val Phe Leu Ile Leu Leu Gly Ile Gly Ile Tyr Phe Tyr Trp Ser
                355                 360                 365

Lys Cys Ser Arg Glu Val Leu Trp His Cys His Leu Cys Pro Ser Ser
370                 375                 380

Thr Glu His Ala Ser Ala Ser Ala Asn Gly His Val Ser Tyr Ser Ala
385                 390                 395                 400

Val Ser Arg Glu Asn Ser Ser Ser Gln Asp Pro Gln Thr Glu Gly Thr
                405                 410                 415

Arg

<210> SEQ ID NO 179
<211> LENGTH: 330
<212> TYPE: PRT
<213> ORGANISM: Homo sapiens

<400> SEQUENCE: 179

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                165                 170                 175
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 180
<211> LENGTH: 990
<212> TYPE: DNA
<213> ORGANISM: Homo sapiens

<400> SEQUENCE: 180
gccagcacca agggcccag cgtgttcccc ctggccccca gcagcaagag caccagcggc       60
ggcacagccg ccctgggctg cctggtgaag gactacttcc ccgagcccgt gaccgtgtcc      120
tggaacagcg gagccctgac cagcggcgtg cacaccttcc ccgccgtgct gcagagcagc      180
ggcctgtaca gcctgagcag cgtggtgacc gtgcccagca gcagcctggg cacccagacc      240
tacatctgta acgtgaacca caagcccagc aacaccaagg tggacaagaa ggtggagccc      300
aagagctgtg acaagaccca cacctgcccc cctgccctg cccccgagct gctgggaggc       360
cccagcgtgt tcctgttccc ccccaagcct aaggacaccc tgatgatcag cagaaccccc      420
gaggtgacct gtgtggtggt ggatgtgagc cacgaggacc ctgaggtgaa gttcaactgg      480
tacgtggacg gcgtggaggt gcacaatgcc aagaccaagc caggaggaga gcagtacaac      540
agcacctacc gggtggtgtc cgtgctgacc gtgctgcacc aggattggct gaacggcaag      600
gagtacaagt gtaaggtgtc caacaaggcc ctgcctgccc ctatcgagaa aaccatcagc      660
aaggccaagg gccagcccag agagcccag gtgtacaccc tgccccctag cagagatgag       720
ctgaccaaga accaggtgtc cctgacctgc ctggtgaagg gcttctaccc cagcgacatc      780
gccgtggagt gggagagcaa cggccagccc gagaacaact acaagaccac ccccctgtg       840 ctggacagcg atggcagctt cttcctgtac agcaagctga ccgtggacaa gagcagatgg      900
cagcagggca acgtgttcag ctgctccgtg atgcacgagg ccctgcacaa tcactacacc      960
cagaagagcc tgagcctgtc ccctggcaag                                       990
```

ANTIGEN BINDING PROTEINS

CROSS-REFERENCE TO RELATED APPLICATIONS

This application is a Continuation of International Application No. PCT/EP2020/076834, filed 25 Sep. 2020, which claims the benefit of U.S. Provisional Application No. 62/906,876, filed 27 Sep. 2019, and U.S. Provisional Application No. 63/057,508, filed 28 Jul. 2020, all of which are incorporated herein by reference in their entireties.

FIELD OF THE INVENTION

The present invention relates to antigen binding proteins and fragments thereof that specifically bind to CD96 and in particular human CD96. The present invention also relates to methods of treating diseases or disorders with said antigen binding fragments, pharmaceutical compositions comprising said antigen binding fragments, and methods of manufacture. Other embodiments of the present invention will be apparent from the description below.

REFERENCE TO SEQUENCE LISTING SUBMITTED ELECTRONICALLY

The instant application contains a Sequence Listing which has been submitted in ASCII format via EFS-WEB and is hereby incorporated by reference in its entirety. Said ASCII copy, created on 7 Dec. 2021, is named "PU66651 Replacement Sequence Listing.txt" and is 153 KB in size.

BACKGROUND TO THE INVENTION

CD96/TACTILE ("T cell activation increased late expression") is a cell surface receptor in the immunoglobulin superfamily, which is expressed mainly on T cells, natural killer (NK) cells, and natural killer T (NKT) cells. CD96 belongs to a family of receptors, which includes CD226 and TIGIT ("T cell immunoreceptor with Ig and ITIM domains") that are known to interact with nectin and nectin-like ligands. CD155/NECLS ("nectin-like protein-5") is the primary ligand for all three receptors (CD96, TIGIT and CD226). TIGIT binds to CD155 with higher affinity (3.15 nM) than CD226 (119 nM), and CD96 binding is intermediate (37.6 nM) (Martinet L. & Smyth M. J. Nat Rev Immunol. 2015 Apr.; 15(4): 243-54). Besides CD155, both TIGIT and CD226 also bind another ligand CD112 with much reduced affinity. Recently a new receptor CD112R was discovered that also binds to CD112 (Zhu Y., et al. J Exp Med. 2016 Feb 8; 213(2): 167-76).

Among the receptors in this axis, CD226 (DNAM-1) is one of the major activating receptors for NK cells. CD226 has been reported to potentiate NK cell cytotoxicity against cancer cells, and is critical for tumor immunosurveillance (Lakshmikanth T., et al. J Clin Invest. 2009; 119(5): 1251-63; Chan C. J., et al. J Immunol. 2010; 184(2): 902-11; Gilfillan S., et al. J Exp Med. 2008; 205(13): 2965-73; Iguchi-Manaka A., et al. J Exp Med. 2008; 205(13): 2959-64). Conversely, both CD96 (Chan C. J., et al. Nat Immunol. 2014; 15(5): 431-8) and TIGIT (Lozano E., et al. J Immunol. 2012; 188(8): 3869-75) are known to dampen immune responses through inhibition of NK and/or T cell function. TIGIT expression has been associated with T cell exhaustion (Lozano E., et al. 2012; Kurtulus S., et al. J Clin Invest. 2015; 125(11): 4053-62) and NK cell exhaustion (Zhang Q., et al. Nat Immunol. 2018; 19(7): 723-32), and several anti-TIGIT antibodies are in clinical development.

Overall, there is considerably more literature and mechanistic understanding on CD226 and TIGIT relative to CD96. CD226 does not have a classic ITAM motif as in other immune activating receptors. Upon ligand binding and receptor dimerization, it conducts a positive signaling through a series of phosphorylation events including PKC and Vav1 proteins. The cytoplasmic tail of TIGIT contains an ITT motif and a classic inhibitory ITIM motif. Upon CD155 binding, tyrosine phosphorylation of the ITT motif occurs, and immune inhibitory signaling is transduced downstream involving SHIP1. In contrast, no signaling for CD96 has yet been elucidated. It is known that there is a potentially inhibitory ITIM motif in the cytoplasmic tail of CD96, as well as a potentially activating YXXM motif that is present in multiple immune activating receptors (e.g. ICOS and CD28) (Georgiev H., et al. Front Immunol. 2018; 9: 1072).

Although CD96 was discovered over 25 years ago (Wang P. L., et al. J Immunol. 1992; 148(8): 2600-8), little was known about the function of CD96 other than the fact that it is a member of the immunoglobulin family that shares the ligand CD155 with CD226 and TIGIT (Fuchs A., et al. J Immunol. 2004; 172(7): 3994-8). Subsequent publications linking CD96 to cancer centered mostly on CD96 as a leukemia stem cell (LSC) marker. The first paper indicating CD96 as a potential immuno oncology target was published by the lab of Professor Mark Smyth in 2014; CD96 was shown to compete with CD226 for CD155 binding in NK cells and CD96 negatively regulated production of pro-inflammatory cytokines including IFNγ (gamma) in mice after activation by LPS (Chan C. J., et al. 2014). CD96 knockout mice as well as anti-CD96 antibody-treated mice were less susceptible to MCA-induced sarcoma formation (Id.). In the same study, CD226 or CD155 blockade resulted in a worse outcome, and this is postulated to be due to the loss of the CD155:CD226 activatory pathway (Id.).

Subsequently, further in vivo studies supporting the inhibition of CD96 for cancer treatment have been published (See, e.g. Blake S. J., et al. Cancer Discov. 2016; 6(4): 446-59; Brooks J., et al. 2018; 78(2): 475-88; Harjunpää H., et al. Oncoimmunology. 2018; 7(7): e1445949). Accordingly, a need exists for improved antigen binding proteins and fragments thereof that target CD96 for use in the treatment of disease. Such compositions and related methods are provided in the present disclosure.

SUMMARY OF THE INVENTION

The present invention provides, in a first aspect, CD96 binding proteins. The present invention also provides, in a second aspect, nucleic acid constructs encoding CD96 binding proteins. In a third aspect, the present invention provides expression vectors comprising the nucleic acid according to the second aspect. In a fourth aspect, the present invention provides a recombinant host cell comprising the nucleic acid or expression vector described in the previous aspects. The present invention further provides, in a fifth aspect, methods of producing a CD96 binding protein comprising culturing the host cell as described in the preceding aspect under conditions suitable for expression of said nucleic acid sequence(s) or vector(s), whereby a polypeptide comprising the CD96 binding protein is produced. A sixth aspect of the disclosure is the CD96 binding protein produced by the method for the production described in the preceding aspect. The present invention also provides, in a seventh aspect, pharmaceutical compositions comprising the CD96 binding protein described in any one of the preceding aspects, and a pharmaceutically acceptable excipient. Another aspect of the disclosure is a method of treatment of a disease in a subject in need thereof comprising administering to said subject a therapeutically effective amount of the CD96 binding protein or the pharmaceutical composition as described in any one of the preceding aspects to the subject. A further aspect of the disclosure is the method of treatment described in the preceding aspect further comprising whether the subject expresses CD96. Another aspect of the disclosure is a CD96 binding protein or a pharmaceutical composition as described in any one of the preceding aspects for use in therapy or for use in the treatment of a disease.

The following detailed description of preferred embodiments of the invention will be better understood when read in conjunction with the appended drawings. For the purpose of illustrating the invention, there are shown in the drawings, embodiments which are presently preferred. It should be understood, however, that the invention is not limited to the precise arrangements and instrumentalities of the embodiments shown in the drawings.

DESCRIPTION OF DRAWINGS/FIGURES

FIG. 2 shows solution equilibrium titration (SET) data for CD96 binding protein binding to human (a), cynomolgus monkey (b) or mouse (c) CD96.

FIG. 6 shows CD96 internalisation using imaging cytometry in $CD8^+$ T cells following binding to human PBMCs using imaging cytometry; representative cell images of $CD8^+$ T cells (Gray=CD8 staining, white=CD96 binding protein-PE staining)

FIG. 12 shows the EC50 data for IFNγ release of CD96 binding proteins (expressed from CHO or HEK cells) in a mixed PMBC-MLR assay.

FIGS. 15A, 15B and 15C show the frequency of $IFNγ^+$ cells in different cell populations on day 3 in a mixed PBMC-MLR assay, in the presence of CD96 binding protein and controls.

FIGS. 16A, 16B and 16C show the frequency of $CD96^+$ cells in $CD4^+$, $CD8^+$, and NK cell populations upon treatment with CD96 binding protein and controls in a mixed PBMC-MLR assay.

FIGS. 17A, 17B and 17C show expression level of CD96 in $CD4^+$, $CD8^+$, and NK cell populations upon treatment with CD96 binding proteins and controls in a mixed PBMC-MLR assay.

FIG. 25 shows images of CD96 binding protein treated $CD4^+/CD8^+$ depleted mouse lungs vs control at day 20 (end of study).

DETAILED DESCRIPTION OF THE INVENTION

Figure 1:
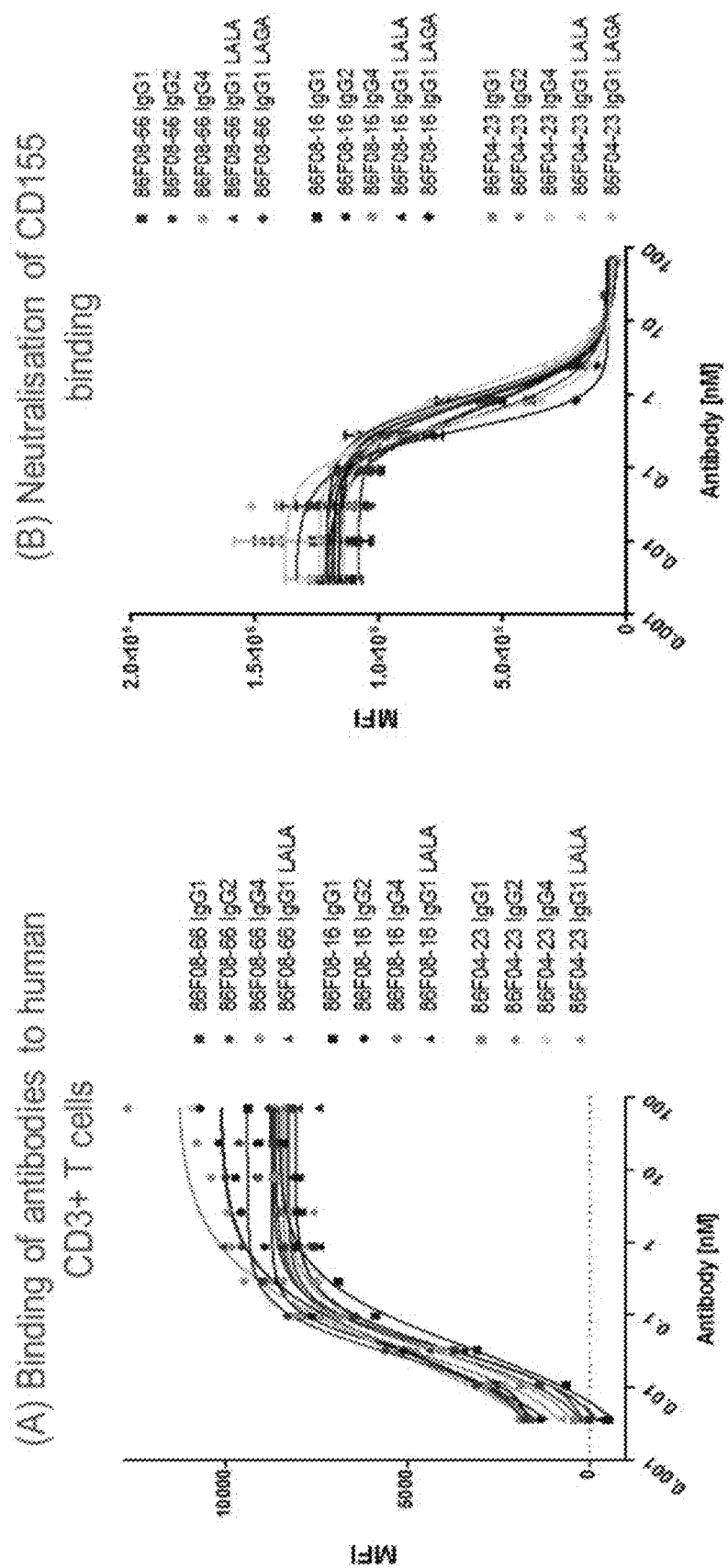
FIG. 1 shows binding of CD96 binding proteins to human $CD3^+$ T cells (A), and the ability for CD96 binding proteins to prevent the binding of CD155 to CHO cells expressing human CD96 (B).

The present disclosure provides CD96 binding proteins, nucleic acids encoding said proteins, and related subject matter.

As used herein and in the claims, the singular forms "a," "and," and "the" include plural reference unless the context clearly dictates otherwise. Thus, for example, reference to "a peptide chain" is a reference to one or more peptide chains and includes equivalents thereof known to those skilled in the art.

As used herein and in the claims, the term "comprising" encompasses "including" or "consisting" e.g. a composition "comprising" X may consist exclusively of X or may include something additional, e.g., X+Y.

The term "consisting essentially of" limits the scope of the feature to the specified materials or steps and those that do not materially affect the basic characteristic(s) of the claimed feature.

The term "consisting of" excludes the presence of any additional component(s).

Unless defined otherwise, all technical and scientific terms used herein have the same meaning as commonly understood by one of ordinary skill in the art to which this invention belongs. Although any compositions and methods similar or equivalent to those described herein can be used in the practice or testing of the methods of the disclosure, exemplary compositions and methods are described herein. Any of the aspects and embodiments of the disclosure described herein may also be combined. For example, the subject matter of any dependent or independent claim disclosed herein may be multiply combined (e.g., one or more recitations from each dependent claim may be combined into a single claim based on the independent claim on which they depend).

Ranges provided herein include all values within a particular range described and values about an endpoint for a particular range. The figures and tables of the disclosure also describe ranges, and discrete values, which may constitute an element of any of the methods disclosed herein.

Concentrations described herein are determined at ambient temperature and pressure. This may be, for example, the temperature and pressure at room temperature or in within a particular portion of a process stream. Preferably, concentrations are determined at a standard state of 25° C. and 1 bar of pressure.

The term "about" means a value within two standard deviations of the mean for any particular measured value.

"Affinity" is the strength of binding of one molecule to another. The binding affinity of an antigen binding protein to its target may be determined by equilibrium methods (e.g. enzyme-linked immunosorbent assay (ELISA) or radioimmunoassay (RIA)), or kinetics (e.g. BIACORE™ analysis).

The term "antigen" as used herein refers to a structure of a macromolecule which is selectively recognized by an antigen binding protein. Antigens include but are not limited to protein (with or without polysaccharides) or protein composition comprising one or more T cell epitopes. As is contemplated herein, the target binding domains an antigen binding protein may recognize a sugar side chain of a glycoprotein rather than a specific amino acid sequence or of a macromolecule. Thus, the sugar moiety or sulfated sugar moiety serves as an antigen.

The term "antigen binding protein", as used herein refers to isolated proteins, antibodies, antibody fragments (e.g., Fabs etc.) and other antibody derived protein constructs, such as those comprising domains (e.g., domain antibodies etc.) which are capable of binding to CD96. Such alternative antibody formats include triabody, tetrabody, miniantibody, and a minibody. Also included are alternative scaffolds in which the one or more CDRs of any molecules in accordance with the disclosure can be arranged onto a suitable non-immunoglobulin protein scaffold or skeleton, such as an affibody, a SpA scaffold, an LDL receptor class A domain, an avimer (see, e.g., U.S. Patent Application Publication Nos. 2005/0053973, 2005/0089932, 2005/0164301) or an EGF domain. An ABP also includes antigen binding fragments of such antibodies or other molecules. Further, an ABP may comprise the VH regions of the invention formatted into a full length antibody, a (Fab')2 fragment, a Fab fragment, a bi-specific or biparatopic molecule or equivalent thereof (such as scFV, bi- tri- or tetra-bodies, Tandabs, etc.), when paired with an appropriate light chain. The ABP may comprise an antibody that is an IgG1, IgG2, IgG3, or IgG4; or IgM; IgA, IgE or IgD or a modified variant thereof. The constant domain of the antibody heavy chain may be selected accordingly. The light chain constant domain may be a kappa or lambda constant domain. The ABP may also be a chimeric antibody of the type described in WO86/01533, which comprises an antigen binding region and a non-immunoglobulin region. The antigen binding proteins of the disclosure can be provided as a lyophilized powder containing the antibody and excipients which can be reconstituted with a pharmaceutically acceptable carrier (e.g., sterile water). This reconstituted pharmaceutical composition can then be administered either subcutaneously or intravenously (e.g., with further dilution). The antigen binding proteins of the disclosure can also be provided as a liquid formulation containing the antibody, excipients and a pharmaceutically acceptable carrier. This liquid pharmaceutical composition can then be administered either subcutaneously or intravenously (e.g., with further dilution). The terms "ABP," "antigen binding protein," and "binding protein" are used interchangeably herein. As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "antibody variant" as used herein means an antibody that differs from a parent antibody by virtue of at least one amino acid modification (e.g., by having a different amino acid side chain), post-translational modification or other modification in at least one heavy chain, light chain, or combinations of these that results in a structural change (e.g., different amino acid side chain, different post-translational modification or other modification) relative to the parent antibody. Structural changes can be determined directly by a variety of methods well known in the art such as LC-MS, direct sequencing or indirectly via methods such as isoelectric focusing and the like. Such methods are well known to those of ordinary skill in the art.

The term "epitope" as used herein refers to that portion of the antigen that makes contact with a particular binding domain. An epitope may be linear or conformational/discontinuous. A conformational or discontinuous epitope comprises amino acid residues that are separated by other sequences, i.e. not in a continuous sequence in the antigen's primary sequence. Although the residues may be from different regions of the peptide chain, they are in close proximity in the three dimensional structure of the antigen. In the case of multimeric antigens, a conformational or discontinuous epitope may include residues from different peptide chains. Particular residues comprised within an epitope can be determined through computer modelling programs or via three-dimensional structures obtained through methods known in the art, such as X-ray crystallography. As is contemplated herein the term epitope includes post-translational modification to a polypeptide that can be recognized by an antigen binding protein or domain, such as sugar moiety of a glycosylated protein.

The term "isolated" as used herein, means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

CD96 (Cluster of Differentiation 96), also known as TACTILE, is a receptor expressed on T cells and NK cells, shares sequence similarity with CD226 (DNAM01), and is a type 1 transmembrane glycoprotein belonging to the immunoglobulin superfamily.

Human CD96 has 3 isoforms: two membrane (V1; V2) and a soluble form. The longer V1 isoform is a 585 amino acid protein with a MW of 65,634 Da. A shorter isoform V2 (569 aa) has a MW of 63,888 Da. V2 differs from V1 by having a short deletion of the Ig fold of the second domain. The first domain of CD96 is reported to contain the epitope(s) required for CD155 binding while the second domain modulates the magnitude/strength of binding. CD96V2 binds much more strongly to CD155 than does CD96V1, and is also a predominantly expressed form with the exception of acute myeloid leukemia AML (cells). Little is known about the soluble form of CD96 (sCD96). It has been reported that sCD96 was detected in healthy donor blood (1-3 ng/ml), with higher levels detected in hepatitis B virus (HBV) HBV/liver cirrhosis patients.

Based on mRNA analysis of normal human tissues the highest expression of CD96 (probe detecting both V1 and V2 of CD96) is observed in hematopoietic cells. CD96 expression is also observed in tissues containing large numbers of lymphocytes, such as spleen, lungs, thyroid and small intestine. Among hematopoietic cells, CD96 is most abundant in T cells and NK cells, with lower expression in some B cells. Like CD96, TIGIT and CD226 are most abundant in hematopoietic cells, and expressed in both T cells and NK cells. CD226 is also expressed in conventional DC cells. The ligand CD155 shows a broad expression pattern in human normal tissue and is also expressed in DC cells and macrophages (antigen presenting cells). CD155 is not expressed in T cells or NK cells.

The binding affinity (KD) of the antigen binding protein-target antigen interaction may be 1 mM or less, 100 nM or less, 10 nM or less, 2 nM or less or 1 nM or less. Alternatively, the KD may be between 5 and 10 nM; or between 1 and 2 nM. The KD may be between 1 pM and 500 pM; or between 500 pM and 1 nM. For example certain useful such variants have a binding affinity (KD) which is at least about 40 nM or at least about 35 nM or at least about 30 nM e.g. about 10 pM to about 30 nM.

The binding affinity of the antigen binding protein is determined by the association constant (Ka) and the dissociation constant (Kd) (KD=Kd/Ka). The binding affinity may be measured by BIACORE™, for example, by capture of the test antibody onto a protein-A coated sensor surface and flowing target antigen over this surface. Alternatively, the binding affinity can be measured by FORTEBIO, for example, with the test antibody receptor captured onto a protein-A coated needle and flowing target antigen over this surface. Alternatively the binding affinity (KD) can be measured by using MSD-SET analysis (MSD solution equilibrium titration) for example with the test antibody titrarated onto a standard bind MSD plate and detected using an MSD SECTOR IMAGER. MSD-SET determines the solution phase, equilibrium affinity of antibodies. This known method relies on the detection of free antigen at equilibrium in a titrated series of antibody concentrations.

The Kd may be $1 \times 10^{-3}$ Ms-1 or less, $1 \times 10^{-4}$ Ms-1 or less, or $1 \times 10^{-5}$ Ms-1 or less. The Kd may be between $1 \times 10^{-5}$ Ms-1 and $1 \times 10^{-4}$ Ms-1; or between $1 \times 10^{-4}$ Ms-1 and $1 \times 10^{-3}$ Ms-1. A slow Kd may result in a slow dissociation of the antigen binding protein-target antigen complex and improved neutralization of the target antigen.

The term "specific antigen binding activity" as used herein means antigen binding activity as measured e.g. by Surface Plasmon Resonance (SPR). CD96 specific binding activity may be determined by SPR using a BIACORE™ instrument, for example performed in the binding mode. It is binding activity divided by total protein content in a sample.

The terms "VH" and "VL" are used herein to refer to the heavy chain variable region and light chain variable region respectively of an antigen binding protein.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least one CDR and wherein the at least one CDR is CDRH3. Framework regions follow each of these CDR regions. Acceptable heavy chain variable region and light chain variable region framework 1, framework 2 and framework 3 regions are readily recognized by those of ordinary skill in the art. Acceptable heavy chain constant regions (including hinge regions) and light chain constant regions are readily recognized by those of ordinary skill in the art as well. Acceptable antibody isotypes are similarly readily recognized by those of ordinary skill in the art.

Throughout this specification, amino acid residues in variable domain sequences and full length antibody sequences are numbered according to the Kabat numbering convention. Similarly, the terms "CDR", "CDRL1", "CDRL2", "CDRL3", "CDRH1", "CDRH2", "CDRH3" used in the specification follow the Kabat numbering convention.

It will be apparent to those skilled in the art that there are alternative numbering conventions for amino acid residues in variable domain sequences and full length antibody sequences. There are also alternative numbering conventions for CDR sequences, for example those set out according to the Chothia numbering convention. The structure and protein folding of the antibody may mean that other residues are considered part of the CDR sequence and would be understood to be so by a skilled person.

Other numbering conventions for CDR sequences available to a skilled person include "AbM" (University of Bath) and "contact" (University College London) methods. The minimum overlapping region using at least two of the Kabat, Chothia, AbM and contact methods can be determined to provide the "minimum binding unit". The minimum binding unit may be a sub-portion of a CDR.

Table 1 below represents one definition using each numbering convention for each CDR or binding unit. The Kabat numbering scheme is used in Table 1 to number the variable domain amino acid sequence. It should be noted that some of the CDR definitions may vary depending on the individual publication used.

TABLE 1

| | Kabat CDR | Chothia CDR | AbM CDR | Contact CDR | Minimum binding unit |
|---|---|---|---|---|---|
| H1 | 31-35/ 35A/35B | 26-32/ 33/34 | 26-35/ 35A/35B | 30-35/ 35A/35B | 31-32 |
| H2 | 50-65 | 52-56 | 50-58 | 47-58 | 52-56 |
| H3 | 95-102 | 95-102 | 95-102 | 93-101 | 95-101 |
| L1 | 24-34 | 24-34 | 24-34 | 30-36 | 30-34 |
| L2 | 50-56 | 50-56 | 50-56 | 46-55 | 50-55 |
| L3 | 89-97 | 89-97 | 89-97 | 89-96 | 89-96 |

In one embodiment of the disclosure is a CD96 binding protein comprising: (a) (i) any one or a combination of CDRs selected from CDRH1, CDRH2, CDRH3 from SEQ ID NOS: 2, 6, 10, 14, 18, 22, 26, 30, 34, 38, 42, 46, 50, 54, 58, 62, 66, 70, 74, 78, 82, 86, 90, and 94, and/or CDRL1, CDRL2, CRDL3 from SEQ ID NOS: 1, 5, 9, 13, 17, 21, 25, 29, 33, 37, 41, 45, 49, 53, 57, 61, 65, 69, 73, 77, 81, 85, 89, and 93; or (ii) a CDR variant of (i) wherein the variant has 1, 2, or 3 amino acid modifications; or (b) a VH region comprising a sequence at least 80% identical (or at least 85%, 90%, 91%, 92%, 93%, 94%, 95%, 96%, 97%, 98%, 99%, 99.5% identical) to the sequence of SEQ ID NOS: 2, 6, 10, 14, 18, 22, 26, 30, 34, 38, 42, 46, 50, 54, 58, 62, 66, 70, 74, 78, 82, 86, 90, or 94; and/or a VL region comprising a sequence at least 80% identical to the sequence of SEQ ID NOS: 1, 5, 9, 13, 17, 21, 25, 29, 33, 37, 41, 45, 49, 53, 57, 61, 65, 69, 73, 77, 81, 85, 89, or 93.

In another embodiment, the CD96 binding protein comprises: (a) (i) any one or a combination of CDRs selected from CDRH1, CDRH2, CDRH3 from SEQ ID NOS: 2, 6, 10, 14, 18, 22, 26, 30, 34, 38, 42, 46, 50, 54, 58, 62, 66, 70, 74, 78, 82, 86, 90, and 94, and/or CDRL1, CDRL2, CRDL3 from SEQ ID NOS: 1, 5, 9, 13, 17, 21, 25, 29, 33, 37, 41, 45, 49, 53, 57, 61, 65, 69, 73, 77, 81, 85, 89, and 93; or (ii) a CDR variant of (i) wherein the variant has 1, 2, or 3 amino acid modifications; or (b) a VH region comprising a sequence of SEQ ID NOS: 2, 6, 10, 14, 18, 22, 26, 30, 34, 38, 42, 46, 50, 54, 58, 62, 66, 70, 74, 78, 82, 86, 90, or 94; and/or a VL region comprising a sequence at least 80% identical (or at least 85%, 90%, 91%, 92%, 93%, 94%, 95%, 96%, 97%, 98%, 99%, 99.5% identical) to the sequence of SEQ ID NO: 1, 5, 9, 13, 17, 21, 25, 29, 33, 37, 41, 45, 49, 53, 57, 61, 65, 69, 73, 77, 81, 85, 89, or 93.

Another embodiment of the disclosure is the CD96 binding protein described in the previous aspect comprising a CDRH1 selected from SEQ ID NOS: 105-125; a CDRH2 selected from SEQ ID NOS: 126-146; and/or a CDRH3 selected from SEQ ID NOS: 147-150; a CDRL1 selected from of SEQ ID NOS: 97-98; a CDRL2 selected from SEQ ID NOS: 99-100; and/or a CDRL3 selected from SEQ ID NOS: 101-104.

Another embodiment of the disclosure is the CD96 binding protein described in any one of the preceding aspects wherein the binding protein comprises CDRH3 that is 100% identical to Seq ID NOS: 147, 148, 149, or 150.

Another embodiment of the disclosure is the CD96 binding protein described in any one of the preceding aspects comprising a CDRH1 that is 100% identical to SEQ ID NO: 105, 106, 107, 108, 109, 110, 111, 112, 113, 114, 115, 116, 117, 118, 119, 120, 121, 122, 123, 124 or 125; a CDRH2 that is 100% identical to SEQ ID NO: 126, 127, 128, 129, 130, 131, 132, 133, 134, 135, 136, 137, 138, 139, 140, 141, 142, 143, 144, 145, or 146; and/or a CDRH3 that is 100% identical to SEQ ID NO: 147, 148, 149, or 150; a CDRL1 that is 100% identical to SEQ ID NO: 97 or 98; a CDRL2 that is 100% identical to SEQ ID NO: 99 or 100; and/or a CDRL3 that is 100% identical to SEQ ID NO: 101, 102, 103, or 104.

Another embodiment of the disclosure is the CD96 binding protein described in any one of the preceding aspects wherein all 6 CDRs are present in the binding protein.

Another embodiment of the disclosure is the CD96 binding protein described in any one of the preceding aspects comprising a CDRH1 of SEQ ID NO: 115; a CDRH2 of SEQ ID NO: 145; and a CDRH3 of SEQ ID NO: 147; and/or a CDRL1 of SEQ ID NO: 97; a CDRL2 of SEQ ID NO: 99; and a CDRL3 of SEQ ID NO: 101.

Another embodiment of the disclosure is the CD96 binding protein described in any one of the preceding aspects wherein the binding protein comprises: a VH region that is 75% identical to SEQ ID NO: 86; and/or a VL region that is 75% identical to SEQ ID NO: 85 (or at least 85%, 90%, 91%, 92%, 93%, 94%, 95%, 96%, 97%, 98%, 99%, 99.5% identical to these sequences). Another aspect of the disclosure is the CD96 binding protein described in any one of the preceding aspects wherein the binding protein comprises: a VH region that is 100% identical to SEQ ID NO: 86; and/or a VL region that is 100% identical to SEQ ID NO: 85.

In one embodiment of the disclosure the invention provides a CD96 binding protein which comprises the any of the CDRs as described herein (alone or in the combinations described) and which also comprise an Fc region which can bind to the Fc gamma receptor and/or can promote IFN-gamma release. Such an Fc region can be the wild type IgG1 Fc.

In one embodiment of the disclosure the invention provides a CD96 binding protein which comprises the any of the VH regions as described herein (alone or in the combinations described) and which also comprise an Fc region which can bind to the Fc gamma receptor and/or can promote IFNgamma release. Such an Fc region can be the wild type IgG1 Fc.

In one embodiment of the disclosure the invention provides a CD96 binding protein which comprises the any of the VL regions as described herein (alone or in the combinations described) and which also comprise an Fc region which can bind to the Fc gamma receptor and/or can promote IFNgamma release. Such an Fc region can be the wild type IgG1 Fc.

Another embodiment of the disclosure is the CD96 binding protein as described in any one of the preceding aspects, which is an antibody, wherein the binding protein comprises: a (complete) heavy chain that is 75% identical (or at least 80%, 85%, 90%, 91%, 92%, 93%, 94%, 95%, 96%, 97%, 98%, 99%, 99.5% identical) to SEQ ID NO: 165; and/or a (complete) light chain that is 75% identical (or at least 80%, 85%, 90%, 91%, 92%, 93%, 94%, 95%, 96%, 97%, 98%, 99%, 99.5% identical) to SEQ ID NO: 166.

Another aspect of the disclosure is the CD96 binding protein described in any one of the preceding aspects wherein the binding protein comprises: a VH region that is 100% identical to SEQ ID NO: 86; and/or a VL region that is 100% identical to SEQ ID NO: 85.

Another aspect of the disclosure is the CD96 binding protein described in any one of the preceding aspects, which is an antibody, and wherein the binding protein comprises: a (complete) heavy chain that is 100% identical to the amino acid sequence of SEQ ID NO: 165; and/or a (complete) light chain that is 100% identical to the amino acid sequence of SEQ ID NO: 166 (CDRs are underlined in SEQ ID Nos 165 and 166); or is an antibody which binds to CD96 and wherein the heavy chain is encoded by the nucleic acid sequence of SEQ ID NO: 167 and/or the light chain is encoded by the nucleic acid sequence of SEQ ID NO: 168.

Another aspect of the disclosure is the CD96 binding protein described in any one of the preceding aspects, which is an antibody, and wherein the binding protein comprises: a (complete) heavy chain that is 100% identical to the amino acid sequence of SEQ ID NO: 170; and/or a (complete) light chain that is 100% identical to the amino acid sequence of SEQ ID NO: 169 (CDRs are underlined) or is an antibody which binds to CD96 and wherein the heavy chain is encoded by the nucleic acid sequence of SEQ ID NO: 172 and/or the light chain is encoded by the nucleic acid sequence of SEQ ID NO: 171.

Another aspect of the disclosure is the CD96 binding protein described in any one of the preceding aspects, which is an antibody, and wherein the binding protein comprises: a (complete) heavy chain that is 100% identical to the amino acid sequence of SEQ ID NO: 174; and/or a (complete) light chain that is 100% identical to the amino acid sequence of SEQ ID NO: 173 (CDRs are underlined) or is an antibody which binds to CD96 and wherein the heavy chain is encoded by the nucleic acid sequence of SEQ ID NO: 176 and/or the light chain is encoded by the nucleic acid sequence of SEQ ID NO: 175.

The invention includes binding proteins which are 100% identical to any of the amino acid sequences described herein and also proteins which are variants of the amino acid sequences described herein e.g. sequences which are at least 75% identical or at least 80%, 85%, 90%, 91%, 92%, 93%, 94%, 95%, 96%, 97%, 98%, 99%, 99.5%, identical to the sequences herein.

The invention also included nucleic acids encoding the binding proteins of the invention including nucleic acids which are 100% identical to any of the nucleic acid sequences sequences described herein and also nucleic acids which are variants of the sequences described herein e.g. sequences which are at least 75% identical or at least 80%, 85%, 90%, 91%, 92%, 93%, 94%, 95%, 96%, 97%, 98%, 99%, 99.5%, identical to the sequences herein.

CDRs and variable regions with amino acid sequences provided in the present application have binding affinity to CD96 which is equal to or better than that of CD155 and/or are variable regions which can prevent or displace CD155 from binding to CD96 (examples of binding assays which can be used to determine this are set out in examples 1 and 2 herein). Useful variants of the sequences described herein are variants in which the variable regions have binding affinity to CD96 which is equal to or better than that of CD155 or which can prevent or displace CD155 from binding to CD96 (examples of binding assays which can be used to determine this are set out in examples 1 and 2 herein). For example certain useful such variants have a binding affinity (KD) which is at least about 40 nM or at least about 35 nM or at least about 30 nM e.g. about 10 pM to about 30 nM when for example binding affinity is determined by MSD-SET assays as detailed herein.

Useful CD96 binding proteins (such as antibodies) according to the present invention can comprise such variable regions and also an Fc region as described herein wherein said Fc region can bind to the Fc gamma receptor and/or can promote IFN gamma release. Such an Fc region according to the invention is the wild type IgG1Fc or a functional variant thereof (for example an Fc disabled variant which region can bind to the Fc gamma receptor and/or can promote IFN gamma release). Hence any of the CDRs and/or variable regions of the invention can be combined with an Fc region of the invention e.g. the wild type IgG1 Fc or a functional variant thereof.

Another embodiment of the disclosure is the CD96 binding protein described in any one of the preceding aspects wherein the binding protein comprises a synthetic polypeptide, a humanised sequence, or a chimeric sequence.

As used herein, the term "conservative sequence modifications" is intended to refer to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

The term "domain" refers to a folded protein structure which retains its tertiary structure independent of the rest of the protein. Generally, domains are responsible for discrete functional properties of proteins and in many cases, may be added, removed or transferred to other proteins without loss of function of the remainder of the protein and/or of the domain.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

In one embodiment of the disclosure is a nucleic acid sequence which encodes the CD96 binding protein described in any one of the preceding embodiments.

A further embodiment of the disclosure is the nucleic acid sequence described in the previous embodiment wherein the sequence comprises SEQ ID NO 4, 8, 12, 16, 20, 24, 28, 32, 36, 40, 44, 48, 52, 56, 60, 64, 68, 72, 76, 80, 84, 88, 92, or 96 encoding the heavy chain; and/or SEQ ID NO: 3, 7, 11, 15, 19, 23, 27, 31, 35, 39, 43, 47, 51, 55, 59, 63, 67, 71, 75, 79, 83, 87, 91, or 95 encoding the light chain. Another embodiment of the disclosure is an expression vector comprising the nucleic acid described in any of the preceding embodiments.

The compositions described herein may be produced by any number of conventional techniques. For example, the compositions may be expressed in and purified from recombinant expression systems. In one embodiment, the composition is produced by a method of culturing a host cell under conditions suitable for expression of CD96 binding protein described in any of the preceding embodiments wherein the composition is expressed, and optionally purified, and optionally formulated within a pharmaceutical composition.

A number of different expression systems and purification regimes can be used to produce the compositions. Generally, host cells are transformed with a recombinant expression vector encoding the antibody. A wide range of host cells can be employed, including Eukaryotic cell lines of mammalian origin (e.g., CHO, Perc6, HEK293, HeLa, NS0). Suitable host cells include mammalian cells such as CHO (e.g., CHOK1 and CHO-DG44).

The host cell may be an isolated host cell. The host cell is usually not part of a multicellular organism (e.g., plant or animal). The host cell may be a non-human host cell.

Appropriate cloning and expression vectors for use with eukaryotic or mammalian cellular hosts and methods of cloning are known in the art.

The cells may be cultured under conditions that promote expression of the antibody. For example, a production bioreactor is used to culture the cells. The production bioreactor volume may be: (i) about 20,000 litres, about 10,000 litres; about 5,000 litres; about 2,000 litres; about 1,000 litres; or about 500 litres; or (ii) between 500 and 20,000 litres; between 500 and 10,000 litres; between 500 and 5,000 litres; between 1,000 and 10,000 litres, or between 2,000 and 10,000 litres. For example, the cells may be cultured in a production bioreactor at a pH of about 6.75 to pH 7.00. Alternatively, the cells may be cultured in a production bioreactor for about 12 to about 18 days. Alternatively, the cells may be cultured in a production bioreactor at a pH of about 6.75 to pH 7.00, for about 12 to about 18 days. This culture step may help to control the level of deamidated antibody variants, for example, to reduce the level of deamidated antibody variants.

The composition may be recovered and purified by conventional protein purification procedures. For example, the composition may be harvested directly from the culture medium. Harvest of the cell culture medium may be via clarification, for example by centrifugation and/or depth filtration. Recovery of the composition is followed by purification to ensure adequate purity.

A further embodiment of the disclosure is a recombinant host cell comprising the nucleic acid sequences or the expression vector described in any of the preceding embodiments. Another embodiment of the disclosure is a method for the production of a CD96 binding protein comprising culturing the host cell as described in the preceding embodiment under conditions suitable for expression of said nucleic acid sequence(s) or vector(s), whereby a polypeptide comprising the CD96 binding protein is produced. A further embodiment of the disclosure is the CD96 binding protein produced by the method for the production described in the preceding embodiment. Another embodiment of the disclosure in a cell line engineered to express the CD96 binding protein described in any one of the preceding embodiments.

"Percent identity" between a query nucleic acid sequence and a subject nucleic acid sequence is the "Identities" value, expressed as a percentage, that is calculated by the BLASTN algorithm when a subject nucleic acid sequence has 100% query coverage with a query nucleic acid sequence after a pair-wise BLASTN alignment is performed. Such pair-wise BLASTN alignments between a query nucleic acid sequence and a subject nucleic acid sequence are performed by using the default settings of the BLASTN algorithm available on the National Center for Biotechnology Institute's website with the filter for low complexity regions turned off. Importantly, a query nucleic acid sequence may be described by a nucleic acid sequence identified in one or more claims herein.

"Percent identity" between a query amino acid sequence and a subject amino acid sequence is the "Identities" value, expressed as a percentage, that is calculated by the BLASTP algorithm when a subject amino acid sequence has 100% query coverage with a query amino acid sequence after a pair-wise BLASTP alignment is performed. Such pair-wise BLASTP alignments between a query amino acid sequence and a subject amino acid sequence are performed by using the default settings of the BLASTP algorithm available on the National Center for Biotechnology Institute's website with the filter for low complexity regions turned off. Importantly, a query amino acid sequence may be described by an amino acid sequence identified in one or more claims herein.

The query sequence may be 100% identical to the subject sequence, or it may include up to a certain integer number of amino acid or nucleotide alterations as compared to the subject sequence such that the % identity is less than 100%. For example, the query sequence is at least 50, 60, 70, 75, 80, 85, 90, 95, 96, 97, 98, or 99% identical to the subject sequence. Such alterations include at least one amino acid deletion, substitution (including conservative and non-conservative substitution), or insertion, and wherein said alterations may occur at the amino- or carboxy-terminal positions of the query sequence or anywhere between those terminal positions, interspersed either individually among the amino acids or nucleotides in the query sequence or in one or more contiguous groups within the query sequence.

"Sequence identity" as used herein is the degree of relatedness between two or more amino acid sequences, or two or more nucleic acid sequences, as determined by comparing the sequences. The comparison of sequences and determination of sequence identity may be accomplished using a mathematical algorithm; those skilled in the art will be aware of computer programs available to align two sequences and determine the percent identity between them. The skilled person will appreciate that different algorithms may yield slightly different results.

The term "specifically binds," and grammatical variations thereof as used herein with respect to an antibody, is meant an antibody or antibody fragment which recognizes and binds with a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabelled A), in a reaction containing labelled "A" and the antibody, will reduce the amount of labelled A bound to the antibody.

The term "pharmaceutical composition" as used herein means a composition suitable for administration to a patient.

The pharmaceutical compositions described herein may comprise purified preparations of CD96 binding proteins as described herein.

For example, the pharmaceutical preparation may comprise a purified preparation of a CD96 binding as described herein in combination with a pharmaceutically acceptable carrier.

Typically, such pharmaceutical compositions comprise a pharmaceutically acceptable carrier as known and called for by acceptable pharmaceutical practice. Examples of such carriers include sterilized carriers, such as saline, Ringers solution, or dextrose solution, optionally buffered with suitable buffers to a pH within a range of 5 to 8.

Pharmaceutical compositions may be administered by injection or infusion (e.g., intravenous, intraperitoneal, intradermal, subcutaneous, intramuscular, or intraportal). Such compositions are suitably free of visible particulate matter. Pharmaceutical compositions may comprise between 1 mg to 10 g of antigen binding protein, for example, between 5 mg and 1 g of antigen binding protein. Alternatively, the composition may comprise between 5 mg and 500 mg of antigen binding protein, for example, between 5 mg and 50 mg.

Methods for the preparation of such pharmaceutical compositions are well known to those skilled in the art. Pharmaceutical compositions may comprise between 1 mg to 10 g of antigen binding protein in unit dosage form, optionally together with instructions for use. Pharmaceutical compositions may be lyophilized (freeze dried) for reconstitution prior to administration according to methods well known or apparent to those skilled in the art. Where antibodies have an IgG1 isotype, a chelator of copper, such as citrate (e.g., sodium citrate) or EDTA or histidine, may be added to the pharmaceutical composition to reduce the degree of copper-mediated degradation of antibodies of this isotype. Pharmaceutical compositions may also comprise a solubilizer, such as arginine, a surfactant/anti-aggregation agent such as polysorbate 80, and an inert gas such as nitrogen to replace vial headspace oxygen.

In one embodiment of the disclosure is a pharmaceutical composition comprising the CD96 binding protein as described in any of the preceding embodiments, and a pharmaceutically acceptable excipient. A further embodiment of the disclosure is a pharmaceutical composition comprising a therapeutically effective amount of a CD96 binding protein as described in any one of the preceding embodiments.

The term "anti-tumor effect" as used herein, refers to a biological effect which can be manifested by a reduction in the rate of tumor growth, decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, the terms "cancer," "neoplasm," and "tumor" are used interchangeably and, in either the singular or plural form, refer to cells that have undergone a malignant transformation that makes them pathological to the host organism. Illustrative examples of cells that can be targeted by compositions and methods contemplated in particular embodiments include, but are not limited to the following cancers: synovial sarcoma, non-small-cell lung carcinoma (NSCLC), myxoid round cell liposarcoma (MRCLS), and multiple myeloma (MM). Primary cancer cells can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as computed tomography (CT) scan, magnetic resonance imaging (MRI), X-ray, ultrasound or palpation on physical examination, and/or which is detectable because of the expression of one or more cancer-specific antigens in a sample obtainable from a patient. Tumors may be a hematopoietic (or hematologic or hematological or blood-related) cancer, for example, cancers derived from blood cells or immune cells, which may be referred to as "liquid tumors." Specific examples of clinical conditions based on hematologic tumors include leukemias such as chronic myelocytic leukemia, acute myelocytic leukemia, chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, Hodgkin's lymphoma; and the like.

The cancer may be any cancer in which an abnormal number of blast cells or unwanted cell proliferation is present or that is diagnosed as a hematological cancer, including both lymphoid and myeloid malignancies. Myeloid malignancies include, but are not limited to, acute myeloid (or myelocytic or myelogenous or myeloblastic) leukemia (undifferentiated or differentiated), acute promyeloid (or promyelocytic or promyelogenous or promyeloblastic) leukemia, acute myelomonocytic (or myelomonoblastic) leukemia, acute monocytic (or monoblastic) leukemia, erythroleukemia and megakaryocytic (or megakaryoblastic) leukemia. These leukemias may be referred together as acute myeloid (or myelocytic or myelogenous) leukemia (AML). Myeloid malignancies also include myeloproliferative disorders (MPD) which include, but are not limited to, chronic myelogenous (or myeloid) leukemia (CML), chronic myelomonocytic leukemia (CMML), essential thrombocythemia (or thrombocytosis), and polcythemia vera (PCV). Myeloid malignancies also include myelodysplasia (or myelodysplastic syndrome or MDS), which may be referred to as refractory anemia (RA), refractory anemia with excess blasts (RAEB), and refractory anemia with excess blasts in transformation (RAEBT); as well as myelofibrosis (MFS) with or without agnogenic myeloid metaplasia.

Hematopoietic cancers also include lymphoid malignancies, which may affect the lymph nodes, spleens, bone marrow, peripheral blood, and/or extranodal sites. Lymphoid cancers include B-cell malignancies, which include, but are not limited to, B-cell non-Hodgkin's lymphomas (B-NHLs). B-NHLs may be indolent (or low-grade), intermediate-grade (or aggressive) or high-grade (very aggressive). Indolent B cell lymphomas include follicular lymphoma (FL); small lymphocytic lymphoma (SLL); marginal zone lymphoma (MZL) including nodal MZL, extranodal MZL, splenic MZL and splenic MZL with villous lymphocytes; lymphoplasmacytic lymphoma (LPL); and mucosa-associated-lymphoid tissue (MALT or extranodal marginal zone) lymphoma. Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkitt's lymphoma (BL), Burkitt-like lymphoma, small non-cleaved cell lymphoma (SNCCL) and lymphoblastic lymphoma. Other B-NHLs include immunoblastic lymphoma (or immunocytoma), primary effusion lymphoma, HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL), Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphoma s(T-NHLs), which include, but are not limited to T-cell non-Hodgkin's lymphoma not otherwise specified (NOS), peripheral T-cell lymphoma (PTCL), anaplastic large cell lymphoma (ALCL), angioimmunoblastic lymphoid disorder (AILD), nasal natural killer (NK) cell/T-cell lymphoma, gamma/delta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma, and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extramedullary), lymphoplasmacytic lymphoma (LPL), Waldenstrom's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues" include bone marrow; peripheral blood; thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

In an embodiment cancers that can be treated by the binding proteins of the invention can include solid tumours (e.g. recurrent, metastatic or advanced solid tumours). Examples of such solid tumours include ovarian, lung (e.g. NSCLC), gastric, bladder, colorectal, liver (e.g. HCC), renal (e.g. RCC), and head and neck squamous cell carcinoma (HNSCC).

The term "therapeutic" as used herein means a treatment and/or prophylaxis. A therapeutic effect is obtained by suppression, remission, or eradication of a disease state.

A "therapeutic effective amount" or "effective amount" as used herein, means an amount which provides a therapeutic or prophylactic benefit, or will elicit the biological or medical response of a tissue, system, or subject that is being sought by the researcher, veterinarian, medical doctor or other clinician. Therapeutically effective amounts and treatment regimes are generally determined empirically and may be dependent on factors, such as the age, weight, and health status of the patient and disease or disorder to be treated. Such factors are within the purview of the attending physician.

The term "treating" and grammatical variations thereof as used herein, is meant therapeutic therapy. In reference to a particular condition, treating means: (1) to ameliorate or prevent the condition of one or more of the biological manifestations of the condition, (2) to interfere with (a) one or more points in the biological cascade that leads to or is responsible for the condition or (b) one or more of the biological manifestations of the condition, (3) to alleviate one or more of the symptoms, effects or side effects associated with the condition or treatment thereof, (4) to slow the progression of the condition or one or more of the biological manifestations of the condition and/or (5) to cure said condition or one or more of the biological manifestations of the condition by eliminating or reducing to undetectable levels one or more of the biological manifestations of the condition for a period of time considered to be a state of remission for that manifestation without additional treatment over the period of remission. One skilled in the art will understand the duration of time considered to be remission for a particular disease or condition. Prophylactic therapy is also contemplated thereby. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof. Prophylactic therapy is appropriate, for example, when a subject is considered at high risk for developing cancer, such as when a subject has a strong family history of cancer or when a subject has been exposed to a carcinogen.

The terms "individual," "subject," and "patient" are used herein interchangeably. In one embodiment, the subject is a mammal, such as a primate, for example a marmoset or monkey, or a human. In a further embodiment, the subject is a human.

The dosage of antigen binding protein administered to a subject is generally between 1 µg/kg to 150 mg/kg, between 0.1 mg/kg and 100 mg/kg, between 0.5 mg/kg and 50 mg/kg, between 1 and 25 mg/kg, between about 0.3 mg/kg and about 3 mg/kg or between 1 and 10 mg/kg of the subject's body weight. For example, the dose may be 10 mg/kg, 30 mg/kg, or 60 mg/kg. The dose may also be from 10 mg/kg to 110 mg/mg 15 mg/kg to 25 mg/kg or 15 mg/kg to 100 mg/kg. The antigen binding protein may be administered, for example, parenterally, subcutaneously, intravenously, or intramuscularly. Doses may also be administered on a per subject basis such as about 20 mg per subject to about 750 mg per subject, about 75 mg per subject to about 750 mg per subject, about 20 mg per subject to about 200 mg per subject. The dose may be any discrete subrange with these dosage ranges. For example, the dose may also be administered subcutaneously on a per subject basis such as about 100 mg per subject (e.g., once every four weeks), or 300 mg per subject (or other doses administered may be subcutaneously with provided approximately the same, or comparable, bioavailability is achieved as with intravenous administration—e.g., three doses of 100 mg per subject to achieve a total dose administered subcutaneously of 300 mg per subject).

Ranges provided herein, of any type, include all values within a particular range described and values about an endpoint for a particular range.

If desired, the effective daily dose of an antibody or antigen binding protein of the disclosure (e.g., as a pharmaceutical composition) may be administered as two, three, four, five, six or more doses administered separately at appropriate intervals throughout the day, optionally, in unit dosage forms.

The administration of a dose may be by slow continuous infusion over a period of from 2 to 24 hours, such as from 2 to 12 hours, or from 2 to 6 hours. Such an administration may result in reduced side effects.

The administration of a dose may be repeated one or more times as necessary, for example, three times daily, once every day, once every 2 days, once a week, once a every 14 days, once a month, once every 3 months, once every 4 months, once every 6 months, or once every 12 months. The antigen binding proteins may be administered by maintenance therapy, for example once a week for a period of 6 months or more. The antigen binding proteins may be administered by intermittent therapy, for example, for a period of 3 to 6 months and then no dose for 3 to 6 months, followed by administration of antigen binding proteins again for 3 to 6 months, and so on, in a cycle.

For example, the dose may be administered subcutaneously, once every 14 or 28 days, in the form of multiple doses on each day of administration. In one embodiment, the dosage of the composition is 100 mg once every 4 weeks (28 days).

The antigen binding protein may be administered to the subject in such a way as to target therapy to a particular site.

The CD96 binding protein in the methods of the disclosure may be used in combination or co-administered with one or more other therapeutically active agents, such as antibodies, small molecule inhibitors, or in combination with a cell therapy. The term "co-administration" as used herein is meant either simultaneous administration or any manner of separate sequential administration of a CD96 binding protein, as described herein, and a further active agent or agents, known to be useful in the treatment of cancer, including chemotherapy and radiation treatment. The term further active agent or agents, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered by injection and another compound may be administered orally.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita, T. S. Lawrence, and S. A. Rosenberg (editors), 10th edition (Dec. 5, 2014), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule or anti-mitotic agents; platinum coordination complexes; alkylating agents; antibiotic agents; topoisomerase I inhibitors; topoisomerase II inhibitors; antimetabolites; hormones and hormonal analogues; signal transduction pathway inhibitors; non-receptor tyrosine kinase angiogenesis inhibitors; immunotherapeutic agents; proapoptotic agents; cell cycle signalling inhibitors; proteasome inhibitors; heat shock protein inhibitors; inhibitors of cancer metabolism; and cancer gene therapy agents.

Examples of a further active ingredient or ingredients for use in combination or co-administered with the presently disclosed CD96 binding proteins are anti-neoplastic agents. Examples of anti-neoplastic agents include, but are not limited to, chemotherapeutic agents; immuno-modulatory agents; immune-modulators; and immunostimulatory adjuvants.

The presently disclosed CD96 binding proteins may also be used in combination with anti-TIGIT antibodies. Such a combination may further enhance CD155/CD226 activation. A combination with anti-TIGIT antibody can be used to treat solid tumours such as kidney tumours e.g. renal cell carcinoma (ROC). An examples of such an anti-TIGIT antibody is tiragolumab.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Platinum coordination complexes are non-phase specific anti-cancer agents, which are interactive with DNA. The platinum complexes enter tumor cells, undergo aquation, and form intra- and interstrand crosslinks with DNA causing adverse biological effects to the tumor. Examples of platinum coordination complexes include, but are not limited to, cisplatin and carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Antibiotic anti-neoplastics are non-phase specific agents, which bind or intercalate with DNA. This action disrupts the ordinary function of the nucleic acids, leading to cell death. Examples of antibiotic anti-neoplastic agents include, but are not limited to, actinomycins such as dactinomycin; anthrocyclins such as daunorubicin and doxorubicin; and bleomycins.

Topoisomerase I inhibitors include, but are not limited to, camptothecins. The cytotoxic activity of camptothecins is believed to be related to its topoisomerase I inhibitory activity.

Topoisomerase II inhibitors include, but are not limited to, epipodophyllotoxins. Epipodophyllotoxins are phase specific anti-neoplastic agents derived from the mandrake plant. Epipodophyllotoxins typically affect cells in the S and G2 phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone; aminoglutethimide and other aromatase inhibitors such as anastrozole, letrazole, vorazole, and exemestane; pro-gestrins such as megestrol acetate; estrogens, androgens, and anti-androgens such as flutamide, nilutamide, bicalutamide, cyproterone acetate and 5α-reductases such as finasteride and dutasteride; anti-estrogens such as tamoxifen, toremifene, raloxifene, droloxifene, iodoxyfene, as well as selective estrogen receptor modulators (SERMS); and gonadotropin-releasing hormone (GnRH) and analogues thereof, which stimulate the release of leutinizing hormone (LH) and/or follicle stimulating hormone (FSH), LHRH agonists, and antagonists such as goserelin acetate and leuprolide.

Signal transduction pathway inhibitors are those inhibitors, which block or inhibit a chemical process which evokes an intracellular change. As used herein, this change is cell proliferation or differentiation. Signal transduction inhibitors useful in the present invention include, but are not limited to, inhibitors of receptor tyrosine kinases, non-receptor tyrosine kinases, SH2/SH3domain blockers, serine/threonine kinases, phosphatidyl inositol-3 kinases, myo-inositol signalling, and Ras oncogenes.

Several protein tyrosine kinases catalyze the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFR), tyrosine kinase with immunoglobulin-like and epidermal growth factor homology domains (TIE-2), insulin growth factor −1 (IGFI) receptor, macrophage colony stimulating factor Cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath J. C., Exp. Opin. Ther. Patents, 10(6):803-818 (2000); Shawver L. K., et al., Drug Discov. Today, 2(2): 50-63 (1997); and Lofts, F. J. and Gullick W. J., "Growth factor receptors as targets." in New Molecular Targets for Cancer Chemotherapy, Kerr D. J. and Workman P. (editors), (Jun. 27, 1994), CRC Press. Non-limiting examples of growth factor receptor inhibitors include pazopanib and sorafenib.

Tyrosine kinases, which are not growth factor receptor kinases, are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinha S. and Corey S. J., J. Hematother. Stem Cell Res., 8(5): 465-480 (2004) and Bolen, J. B., Brugge, J. S., Annu. Rev. Immunol., 15: 371-404 (1997).

SH2/SH3 domain blockers are agents that disrupt SH2 or SH3 domain binding in a variety of enzymes or adaptor proteins including, P13-K p85 subunit, Src family kinases, adaptor molecules (Shc, Crk, Nck, Grb2) and Ras-GAP. SH2/SH3 domains as targets for anti-cancer drugs are discussed in Smithgall T. E., J. Pharmacol. Toxicol. Methods, 34(3): 125-32 (1995).

Inhibitors of serine/threonine kinases include, but are not limited to, MAP kinase cascade blockers which include blockers of Raf kinases (rafk), Mitogen or Extracellular Regulated Kinase (MEKs), and Extracellular Regulated Kinases (ERKs); Protein kinase C family member blockers including blockers of PKCs (alpha, beta, gamma, epsilon, mu, lambda, iota, zeta); IkB kinases (IKKa, IKKb); PKB family kinases; AKT kinase family members; TGF beta receptor kinases; and mammalian target of rapamycin (mTOR) inhibitors, including, but not limited to rapamycin (FK506) and rapalogs, RAD001 or everolimus (AFINITOR®), CCI-779 or temsirolimus, AP23573, AZD8055, WYE-354, WYE-600, WYE-687 and Pp121. Examples of inhibitors of serine/threonine kinases include, but are not limited to, trametinib, dabrafenib, and Akt inhibitors afuresertib and N-{(1S)-2-amino-1-[(3,4-difluorophenyl)methyl]ethyl}-5-chloro-4-(4-chloro-1-methyl-1H-pyrazol-5-yl)-2-furancarboxamide.

Inhibitors of phosphatidyl inositol 3-kinase family members including blockers of PI3-kinase, ATM, DNA-PK, and Ku are also useful in the present invention. Such kinases are discussed in Abraham R. T., Curr. Opin. Immunol., 8(3): 412-418 (1996); Canman C. E., and Lim D. S., Oncogene, 17(25): 3301-3308 (1998); Jackson S. P., Int. J. Biochem. Cell Biol., 29(7): 935-938 (1997); and Zhong H., et al., Cancer Res., 60(6): 1541-1545 (2000).

Also useful in the present invention are myo-inositol signalling inhibitors such as phospholipase C blockers and myo-inositol analogs. Such signal inhibitors are described in Powis G., and Kozikowski A., "Inhibitors of Myo-Inositol Signaling." in New Molecular Targets for Cancer Chemotherapy, Kerr D. J. and Workman P. (editors), (Jun. 27, 1994), CRC Press.

Another group of signal transduction pathway inhibitors are inhibitors of Ras oncogene. Such inhibitors include inhibitors of farnesyltransferase, geranyl-geranyl transferase, and CAAX proteases as well as anti-sense oligonucleotides, ribozymes and other immunotherapies. Such inhibitors have been shown to block ras activation in cells containing wild type mutant ras, thereby acting as antiproliferation agents. Ras oncogene inhibition is discussed in Scharovsky O. G., et al., J. Biomed. Sci., 7(4): 292-298 (2000); Ashby M. N., Curr. Opin. Lipidol., 9(2): 99-102 (1998); and Bennett C. F. and Cowsert L. M., Biochem. Biophys. Acta., 1489(1): 19-30 (1999).

Antagonists to receptor kinase ligand binding may also serve as signal transduction inhibitors. This group of signal transduction pathway inhibitors includes the use of humanized antibodies or other antagonists to the extracellular ligand binding domain of receptor tyrosine kinases. Examples of antibody or other antagonists to receptor kinase ligand binding include, but are not limited to, cetuximab (ERBITUX®), trastuzumab (HERCEPTIN®); trastuzumab emtansine (KADCYLA®); pertuzumab (PERJETA®); ErbB inhibitors including lapatinib, erlotinib, and gefitinib; and 2C3 VEGFR2 specific antibody (see Brekken R. A., et al., Cancer Res., 60(18): 5117-5124 (2000)).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alpha beta3) that will inhibit angiogenesis; endostatin and angiostatin (non-RTK) may also prove useful in combination with the disclosed compounds. (See Bruns C. J., et al., Cancer Res., 60(11): 2926-2935 (2000); Schreiber A. B., et al., Science, 232(4755): 1250-1253 (1986); Yen L., et al., Oncogene, 19(31): 3460-3469 (2000)).

Agents used in immunotherapeutic regimens may also be useful in combination with the present invention. There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R. T., et al., Cancer Res., 60(13): 3569-3576 (2000); and Chen Y., et al., Cancer Res., 58(9): 1965-1971 (1998).

Agents used in proapoptotic regimens (e.g., Bcl-2 antisense oligonucleotides) may also be used in the combination of the present invention. Members of the Bcl-2 family of proteins block apoptosis. Upregulation of Bcl-2 has therefore been linked to chemoresistance. Studies have shown that the epidermal growth factor (EGF) stimulates anti-apoptotic members of the Bcl-2 family (i.e., Mcl-1). Therefore, strategies designed to downregulate the expression of Bcl-2 in tumors have demonstrated clinical benefit. Such proapoptotic strategies using the antisense oligonucleotide strategy for Bcl-2 are discussed in Waters J. S., et al., J. Clin. Oncol., 18(9): 1812-1823 (2000); and Kitada S., et al., Antisense Res. Dev., 4(2): 71-79 (1994).

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania G. R., and Chang Y. T., Exp. Opin. Ther. Patents, 10(2): 215-230 (2000). Further, p21WAF1/CIP1 has been described as a potent and universal inhibitor of cyclin-dependent kinases (Cdks) (Ball K. L., Prog. Cell Cycle Res., 3: 125-134 (1997)). Compounds that are known to induce expression of p21WAF1/CIP1 have been implicated in the suppression of cell proliferation and as having tumor suppressing activity (Richon V. M., et al., Proc. Natl. Acad. Sci. USA, 97(18): 10014-10019 (2000)), and are included as cell cycle signaling inhibitors. Histone deacetylase (HDAC) inhibitors are implicated in the transcriptional activation of p21WAF1/CIP1 (Vigushin D. M., and Coombes R. C., Anticancer Drugs, 13(1): 1-13 (2002)), and are suitable cell cycle signaling inhibitors for use in combination herein. Examples of such HDAC inhibitors include, but are not limited to vorinostat, romidepsin, panobinostat, valproic acid, and mocetinostat.

Proteasome inhibitors are drugs that block the action of proteasomes, cellular complexes that break down proteins, like the p53 protein. Several proteasome inhibitors are marketed or are being studied for the treatment of cancer. Suitable proteasome inhibitors for use in combination herein include, but are not limited to bortezomib, disulfiram, epigallocatechin gallate, salinosporamide A, and carfilzomib.

The 70 kilodalton heat shock proteins (Hsp70s) and 90 kilodalton heat shock proteins (Hsp90s) are a family of ubiquitously expressed heat shock proteins. Hsp70s and Hsp90s are over expressed certain cancer types. Several Hsp70 and Hsp90 inhibitors are being studied in the treatment of cancer. Examples of Hsp70 and Hsp90 inhibitors for use in combination herein include, but are not limited to tanespimycin and radicicol.

Many tumor cells show a markedly different metabolism from that of normal tissues. For example, the rate of glycolysis, the metabolic process that converts glucose to pyruvate, is increased, and the pyruvate generated is reduced to lactate, rather than being further oxidized in the mitochondria via the tricarboxylic acid (TCA) cycle. This effect is often seen even under aerobic conditions and is known as the Warburg Effect.

Lactate dehydrogenase A (LDH-A), an isoform of lactate dehydrogenase expressed in muscle cells, plays a pivotal role in tumor cell metabolism by performing the reduction of pyruvate to lactate, which can then be exported out of the cell. The enzyme has been shown to be upregulated in many tumor types. The alteration of glucose metabolism described in the Warburg effect is critical for growth and proliferation of cancer cells and knocking down LDH-A using RNA-i has been shown to lead to a reduction in cell proliferation and tumor growth in xenograft models (Tennant D. A., et al., Nat. Rev. Cancer, 10(4): 267-277 (2010); Fantin V. R., et al., Cancer Cell, 9(6): 425-434 (2006)).

High levels of fatty acid synthase (FAS) have been found in cancer precursor lesions. Pharmacological inhibition of FAS affects the expression of key oncogenes involved in both cancer development and maintenance. Alli P. M., et al., Oncogene, 24(1): 39-46 (2005).

Inhibitors of cancer metabolism, including inhibitors of LDH-A and inhibitors of fatty acid biosynthesis (or FAS inhibitors), are suitable for use in combination herein.

Cancer gene therapy involves the selective transfer of recombinant DNA/RNA using viral or nonviral gene delivery vectors to modify cancer calls for therapeutic purposes. Examples of cancer gene therapy include, but are not limited to suicide and oncolytic gene therapies, as well as adoptive T-cell therapies.

As used herein "immune-modulators" refer to any substance including monoclonal antibodies that affects the immune system. The CD96 binding proteins of the present invention can be considered immune-modulators. Immune-modulators can be used as anti-neoplastic agents for the treatment of cancer. For example, immune-modulators include, but are not limited to, antibodies or other antagonists to CTLA-4, such as ipilimumab (YERVOY®), and PD-1, such as dostarlimab, nivolumab (OPDIVO®), pembrolizumab (KEYTRUDA®), and cemiplimab (LIBTAYO®). Other immune-modulators include, but are not limited to, antibodies or other antagonists to PD-L1, OX-40, LAGS, TIM-3, 41BB, and GITR.

As used herein, "PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in the any of the aspects of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')2, scFv and Fv fragments.

Examples of mAbs that bind to human PD-1, and useful in the various aspects and embodiments of the present invention, are described in U.S. Pat. Nos. 8,552,154; 8,354,509; 8,168,757; 8,008,449; 7,521,051; 7,488,802; WO2004072286; WO2004056875; and WO2004004771.

Other PD-1 antagonists useful in the any of the aspects and embodiments of the present invention include an immunoadhesin that specifically binds to PD-1, and preferably specifically binds to human PD-1, e.g., a fusion protein containing the extracellular or PD-1 binding portion of PD-L1 or PD-L2 fused to a constant region such as an Fc region of an immunoglobulin molecule. Examples of immunoadhesin molecules that specifically bind to PD-1 are described in WO2010027827 and WO2011066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Nivolumab is a humanized monoclonal anti-PD-1 antibody commercially available as OPDIVO®. Nivolumab is indicated for the treatment of some unresectable or metastatic melanomas. Nivolumab binds to and blocks the activation of PD-1, an Ig superfamily transmembrane protein, by its ligands PD-L1 and PD-L2, resulting in the activation of T-cells and cell-mediated immune responses against tumor cells or pathogens. Activated PD-1 negatively regulates T-cell activation and effector function through the suppression of P13k/Akt pathway activation. Other names for nivolumab include: BMS-936558, MDX-1106, and ONO-4538. The amino acid sequence for nivolumab and methods of using and making are disclosed in U.S. Pat. No. 8,008,449.

Pembrolizumab is a humanized monoclonal anti-PD-1 antibody commercially available as KEYTRUDA®. Pembrolizumab is indicated for the treatment of some unresectable or metastatic melanomas. The amino acid sequence of pembrolizumab and methods of using are disclosed in U.S. Pat. No. 8,168,757.

In one embodiment, the PD-1 antagonist comprises any one or a combination of the following CDRs:

```
CDRH1:
                                    (SEQ ID NO: 151)
SYDMS

CDRH2:
                                    (SEQ ID NO: 152)
TISGGGSYTYYQDSVKG

CDRH3:
                                    (SEQ ID NO: 153)
PYYAMDY

CDRL1:
                                    (SEQ ID NO: 154)
KASQDVGTAVA

CDRL2:
                                    (SEQ ID NO: 155)
WASTLHT

CDRL3:
                                    (SEQ ID NO: 156)
QHYSSYPWT
```

In one embodiment, the PD-1 antagonist comprises a heavy chain variable region CDR1 ("CDRH1") comprising an amino acid sequence with one or two amino acid variation(s) ("CDR variant") to the amino acid sequence set forth in SEQ ID NO:151.

In one embodiment, the PD-1 antagonist comprises a heavy chain variable region CDR2 ("CDRH2") comprising an amino acid sequence with five or fewer, such as four or fewer, three or fewer, two or fewer, or one amino acid variation(s) ("CDR variant") to the amino acid sequence set forth in SEQ ID NO:152. In a further embodiment, the CDRH2 comprises an amino acid sequence with one or two amino acid variation(s) to the amino acid sequence set forth in SEQ ID NO:152.

In one embodiment, the PD-1 antagonist comprises a heavy chain variable region CDR3 ("CDRH3") comprising an amino acid sequence with one or two amino acid variation(s) ("CDR variant") to the amino acid sequence set forth in SEQ ID NO:153.

In one embodiment, the PD-1 antagonist comprises a light chain variable region CDR1 ("CDRL1") comprising an amino acid sequence with three or fewer, such as one or two amino acid variation(s) ("CDR variant") to the amino acid sequence set forth in SEQ ID NO:154.

In one embodiment, the PD-1 antagonist comprises a light chain variable region CDR2 ("CDRL2") comprising an amino acid sequence with one or two amino acid variation(s) ("CDR variant") to the amino acid sequence set forth in SEQ ID NO:155.

In one embodiment, the PD-1 antagonist comprises a light chain variable region CDR3 ("CDRL3") comprising an amino acid sequence with three or fewer, such as one or two amino acid variation(s) ("CDR variant") to the amino acid sequence set forth in SEQ ID NO:156. In a particular embodiment, the CDRL3 comprises an amino acid sequence with one amino acid variation to the amino acid sequence set forth in SEQ ID NO:156. In a further embodiment, the variant CDRL3 comprises the amino acid sequence set forth in SEQ ID NO:157.

In one embodiment, the PD-1 antagonist comprises a CDRH1 comprising an amino acid sequence with up to one amino acid variation to the amino acid sequence set forth in SEQ ID NO:151; a CDRH2 comprising an amino acid sequence with up to five amino acid variations to the amino acid sequence set forth in SEQ ID NO:152; a CDRH3 comprising an amino acid sequence with up to one amino acid variation to the amino acid sequence set forth in SEQ ID NO:153; a CDRL1 comprising an amino acid sequence with up to three amino acid variations to the amino acid sequence set forth in SEQ ID NO:154; a CDRL2 comprising an amino acid sequence with up to one amino acid variation to the amino acid sequence set forth in SEQ ID NO:155; and/or a CDRL3 comprising an amino acid sequence with up to three amino acid variations to the amino acid sequence set forth in SEQ ID NO:156.

In one embodiment of the present invention the PD-1 antagonist comprises CDRH1 (SEQ ID NO:151), CDRH2 (SEQ ID NO:151), and CDRH3 (SEQ ID NO:153) in the heavy chain variable region having the amino acid sequence set forth in SEQ ID NO:158. In some embodiments, the anti-PD-1 antibodies of the present invention comprise a heavy chain variable region having at least 90% sequence identity to SEQ ID NO:158. Suitably, the PD-1 antagonists of the present invention may comprise a heavy chain variable region having about 85%, 86%, 87%, 88%, 89%, 90%, 91%, 92%, 93%, 94%, 95%, 96%, 97%, 98%, 99%, or 100% sequence identity to SEQ ID NO:158.

PD-1 antagonist heavy chain (V$_H$) variable region:
(SEQ ID NO: 158)
EVQLLESGGGLVQPGGSLRLSCAASGFTFSSYDMSWVRQAPGKGLEWVSTI

SGGGSYTYYQDSVKGRFTISRDNSKNTLYLQMNSLRAEDTAVYYCASPYYA

MDYWGQGTTVTVSS

In one embodiment, the PD-1 antagonist comprises a heavy chain variable region ("VH") comprising an amino acid sequence with at least about 90%, 91%, 92%, 93%, 94%, 95%, 96%, 97%, 98%, 99% or 100% sequence identity to the amino acid sequence set forth in SEQ ID NO:158 In one embodiment, the VH comprises an amino acid sequence with at least one amino acid variation to the amino acid sequence set forth in SEQ ID NO:158, such as between 1 and 5, such as between 1 and 3, in particular up to 2 amino acid variations to the amino acid sequence set forth in SEQ ID NO:158.

In one embodiment of the present invention the PD-1 antagonist comprises CDRL1 (SEQ ID NO:154), CDRL2 (SEQ ID NO:155), and CDRL3 (SEQ ID NO:156) in the light chain variable region having the amino acid sequence set forth in SEQ ID NO:159. In one embodiment, a PD-1 antagonist of the present invention comprises the heavy chain variable region of SEQ ID NO:158 and the light chain variable region of SEQ ID NO:159.

In some embodiments, the PD-1 antagonists of the present invention comprise a light chain variable region having at least 90% sequence identity to the amino acid sequence set forth in SEQ ID NO:159. Suitably, the PD-1 antagonists of the present invention may comprise a light chain variable region having about 85%, 86%, 87%, 88%, 89%, 90%, 91%, 92%, 93%, 94%, 95%, 96%, 97%, 98%, 99%, or 100% sequence identity to SEQ ID NO:159.

PD-1 antagonist light chain (V$_L$) variable region:
(SEQ ID NO: 159)
DIQLTQSPSFLSAYVGDRVTITCKASQDVGTAVAWYQQKPGKAPKLLIYWA

STLHTGVPSRFSGSGSGTEFTLTISSLQPEDFATYYCQHYSSYPWTFGQGT

KLEIK

In one embodiment, the PD-1 antagonist comprises a light chain variable region ("V$_L$") comprising an amino acid sequence with at least about 90%, 91%, 92%, 93%, 94%, 95%, 96%, 97%, 98%, 99% or 100% sequence identity to the amino acid sequence set forth in SEQ ID NO:159. In one embodiment, the VL comprises an amino acid sequence with at least one amino acid variation to the amino acid sequence set forth in SEQ ID NO:159, such as between 1 and 5, such as between 1 and 3, in particular up to 2 amino acid variations to the amino acid sequence set forth in SEQ ID NO:159.

In one embodiment, the PD-1 antagonist comprises a VH comprising an amino acid sequence with at least about 90%, 91%, 92%, 93%, 94%, 95%, 96%, 97%, 98%, 99% or 100% sequence identity to the amino acid sequence set forth in SEQ ID NO:158; and a VL comprising an amino acid sequence with at least about 90%, 91%, 92%, 93%, 94%, 95%, 96%, 97%, 98%, 99% or 100% sequence identity to the amino acid sequence set forth in SEQ ID NO:159. In one embodiment, the PD-1 antagonist comprises a VH at least about 90% identical to the amino acid sequence of SEQ ID NO:158 and/or a VL at least about 90% identical to the amino acid sequence of SEQ ID NO:159.

In one embodiment, a PD-1 antagonist comprises a VH with the amino acid sequence set forth in SEQ ID NO:158, and a VL with the amino acid sequence set forth in SEQ ID NO:159.

In one embodiment, the PD-1 antagonist is a monoclonal antibody comprising a heavy chain (HC) amino acid sequence having at least 90%, 91%, 92,%, 93%, 94%, 95%, 96%, 97%, 98%, 99% or 100% sequence identity to the amino acid sequence set forth in SEQ ID NO:160.

(SEQ ID NO: 160)
EVQLLESGGGLVQPGGSLRLSCAASGFTFSSYDMSWVRQAPGKGLEWVSTI

SGGGSYTYYQDSVKGRFTISRDNSKNTLYLQMNSLRAEDTAVYYCASPYYA

MDYWGQGTTVTVSSASTKGPSVFPLAPCSRSTSESTAALGCLVKDYFPEPV

TVSWNSGALTSGVHTFPAVLQSSGLYSLSSVVTVPSSSLGTKTYTCNVDHK

PSNTKDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVLHQ

-continued

DWLNGKEYKCKVSNKGLPSSIEKTISKAKGQPREPQVYTLPPSQEEMTKNQ

VSLTCLVKGFYPSDIAVEWESNGQPENNYKTTPPVLDSDGSFFLYSRLTVD

KSRWQEGNVFSCSVMHEALHNHYTQKSLSLSLGK

In one embodiment, the HC comprises an amino acid sequence with at least one amino acid variation to the amino acid sequence set forth in SEQ ID NO:160, such as between 1 and 10, such as between 1 and 7, in particular up to 6 amino acid variations to the amino acid sequence set forth in SEQ ID NO:160. In a further embodiment, the HC comprises one, two, three, four, five, six or seven amino acid variations to the amino acid sequence set forth in SEQ ID NO:160.

In one embodiment, the HC chain comprises a variation at position 380 and/or 385 of SEQ ID NO:160. The asparagine residues at these positions may be modified, e.g. by deamidation (conversion of a asparagine (N) residue into an aspartate (D) residue). Therefore, in one embodiment, the HC comprises an amino acid sequence of SEQ ID NO:162 (N380D), SEQ ID NO:163 (N385D) or SEQ ID NO:164 (N380D and N385D).

In one embodiment, the PD-1 antagonist is a monoclonal antibody comprising a light chain (LC) amino acid sequence having at least 90%, 91%, 92,%, 93%, 94%, 95%, 96%, 97%, 98%, 99% or 100% sequence identity to the amino acid sequence set forth in SEQ ID NO:161.

(SEQ ID NO: 161)
DIQLTQSPSFLSAYVGDRVTITCKASQDVGTAVAWYQQKPGKAPKLLIYWA

STLHTGVPSRFSGSGSGTEFTLTISSLQPEDFATYYCQHYSSYPWTFGQGT

KLEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC

In one embodiment, the LC comprises an amino acid sequence with at least one amino acid variation to the amino acid sequence set forth in SEQ ID NO:161, such as between 1 and 10, such as between 1 and 5, in particular up to 3 amino acid variations to the amino acid sequence set forth in SEQ ID NO:161. In a further embodiment, the LC comprises one, two or three amino acid variations to the amino acid sequence set forth in SEQ ID NO:161.

In one embodiment, the PD-1 antagonist comprises a HC comprising an amino acid sequence with at least about 90%, 91%, 92%, 93%, 94%, 95%, 96%, 97%, 98%, 99% or 100% sequence identity to the amino acid sequence set forth in SEQ ID NO:160; and a LC comprising an amino acid sequence with at least about 90%, 91%, 92%, 93%, 94%, 95%, 96%, 97%, 98%, 99% or 100% sequence identity to the amino acid sequence set forth in SEQ ID NO:161. Therefore, the antibody is an antibody with a heavy chain at least about 90% identical to the heavy chain amino acid sequence of SEQ ID NO:160 and/or with a light chain at least about 90% identical to the light chain amino acid sequence of SEQ ID NO:161.

In one embodiment, the PD-1 antagonist comprises a heavy chain amino acid sequence at least about 90% identical to the amino acid sequence of SEQ ID NO:160 and/or a light chain amino acid sequence at least about 90% identical to the amino acid sequence of SEQ ID NO:161.

In one embodiment, the PD-1 antagonist comprises a heavy chain sequence of SEQ ID NO:160 and a light chain sequence of SEQ ID NO:161. In one embodiment, the antibody is dostarlimab comprising a heavy chain sequence of SEQ ID NO:160 and a light chain sequence of SEQ ID NO:162.

Anti-PD-L1 antibodies and methods of making the same are known in the art. Such antibodies to PD-L1 may be polyclonal or monoclonal, and/or recombinant, and/or humanized. PD-L1 antibodies are in development as immuno-modulatory agents for the treatment of cancer.

Exemplary PD-L1 antibodies are disclosed in U.S. Pat. Nos. 9,212,224; 8,779,108; 8,552,154; 8,383,796; 8,217,149; US Patent Publication No. 20110280877; WO2013079174; and WO2013019906. Additional exemplary antibodies to PD-L1 (also referred to as CD274 or B7-H1) and methods for use are disclosed in U.S. Pat. Nos. 8,168,179; 7,943,743; 7,595,048; WO2014055897; WO2013019906; and WO2010077634. Specific anti-human PD-L1 monoclonal antibodies useful as a PD-1 antagonist in the treatment method, medicaments and uses of the present invention include MPDL3280A, BMS-936559, MED14736, MSB0010718C.

Atezolizumab is a fully humanized monoclonal anti-PD-L1 antibody commercially available as TECENTRIQ®. Atezolizumab is indicated for the treatment of some locally advanced or metastatic urothelial carcinomas. Atezolizumab blocks the interaction of PD-L1 with PD-1 and CD80. Other exemplary PD-L1 antibodies include avelumab (BAVENCIO®), durvalumab (IMFINZI®)

CD134, also known as OX40, is a member of the TNFR-superfamily of receptors which is not constitutively expressed on resting naïve T cells, unlike CD28. OX40 is a secondary costimulatory molecule, expressed after 24 to 72 hours following activation; its ligand, OX4OL, is also not expressed on resting antigen presenting cells, but is following their activation. Expression of OX40 is dependent on full activation of the T cell; without CD28, expression of OX40 is delayed and of fourfold lower levels. OX-40 antibodies, OX-40 fusion proteins and methods of using them are disclosed in U.S. Pat. Nos. 7,504,101; 7,758,852; 7,858,765; 7,550,140; 7,960,515; WO2012027328; WO2013028231.

Additional examples of a further active ingredient or ingredients (anti-neoplastic agent) for use in combination or co-administered with the presently disclosed CD96 binding proteins are antibodies or other antagonists to CD20, retinoids, or other kinase inhibitors. Examples of such antibodies or antagonists include, but are not limited to rituximab (RITUXAN® and MABTHERA®), ofatumumab (ARZERRA®), and bexarotene (TARGRETIN®).

Additional examples of a further active ingredient or ingredients (anti-neoplastic agent) for use in combination or co-administered with the presently disclosed CD96 binding proteins are Toll-like Receptor 4 (TLR4) antagonists, including but not limited to aminoalkyl glucosaminide phosphates (AGPs).

AGPs are known to be useful as vaccine adjuvants and immunostimulatory agents for stimulating cytokine production, activating macrophages, promoting innate immune response, and augmenting antibody production in immunized animals. AGPs are synthetic ligands of TLR4. AGPs and their immunomodulating effects via TLR4 are disclosed in patent publications such as WO 2006016997, WO 2001090129, and/or U.S. Pat. No. 6,113,918 and have been reported in the literature. Additional AGP derivatives are disclosed in U.S. Pat. Nos. 7,129,219, 6,911,434, and 6,525, 028. Certain AGPs act as agonists of TLR4, while others are recognized as TLR4 antagonists.

Additional non-limiting examples of a further active ingredient or ingredients (anti-neoplastic agent) for use in combination or co-administered with the presently disclosed CD96 binding proteins are antibodies to ICOS.

CDRs for murine antibodies to human ICOS having agonist activity are shown in PCT/EP2012/055735 (WO 2012131004). Antibodies to ICOS are also disclosed in WO 2008137915, WO 2010056804, EP 1374902, EP1374901, and EP1125585.

Additional examples of a further active ingredient or ingredients (anti-neoplastic agent) for use in combination or co-administered with the presently disclosed CD96 binding proteins are poly ADP ribose polymerase (PARP) inhibitors. Non-limiting examples of such inhibitors include niraparib, olaparib, rucaparib, and talazoparib.

Additional non-limiting examples of a further active ingredient or ingredients (anti-neoplastic agent) for use in combination or co-administered with the presently disclosed CD96 binding proteins are STING modulating compounds, CD39 inhibitors and A2a and A2a adenosine antagonists.

Select anti-neoplastic agents that may be used in combination with CD96 binding proteins or a pharmaceutically acceptable salt thereof, include but are not limited to: abarelix, abemaciclib, abiraterone, afatinib, aflibercept, aldoxorubicin, alectinib, alemtuzumab, arsenic trioxide, asparaginase, axitinib, AZD-9291, belinostat, bendamustine, bevacizumab, blinatumomab, bosutinib, brentuximab vedotin, cabazitaxel, cabozantinib, capecitabine, ceritinib, clofarabine, cobimetinib, crizotinib, daratumumab, dasatinib, degarelix, denosumab, dinutuximab, docetaxel, elotuzumab, entinostat, enzalutamide, epirubicin, eribulin, filgrastim, flumatinib, fulvestrant, fruquintinib, gemtuzumab ozogamicin, ibritumomab, ibrutinib, idelalisib, imatinib, irinotecan, ixabepilone, ixazomib, lenalidomide, lenvatinib, leucovorin, mechlorethamine, necitumumab, nelarabine, netupitant, nilotinib, obinutuzumab, olaparib, omacetaxine, osimertinib, oxaliplatin, paclitaxel, palbociclib, palonosetron, panitumumab, pegfilgrastim, peginterferon alfa-2b, pemetrexed, plerixafor, pomalidomide, ponatinib, pralatrexate, quizartinib, radium-223, ramucirumab, regorafenib, rolapitant, rucaparib, sipuleucel-T, sonidegib, sunitinib, talimogene laherparepvec, tipiracil, topotecan, trabectedin, trifluridine, triptorelin, uridine, vandetanib, velaparib, vemurafenib, venetoclax, vincristine, vismodegib, and zoledronic acid.

Treatment can be therapeutic, prophylactic or preventative. The subject will be one who is in need thereof. Those in need of treatment may include individuals already suffering from a particular medical disease, in addition to those who may develop the disease in the future.

Thus, the methods, antigen binding proteins and compositions of the disclosure described herein can be used for prophylactic treatment or preventative treatment if specified. In this case, methods, antigen binding proteins and compositions of the disclosure can be used to prevent or delay the onset of one or more aspects or symptoms of a disease. The subject can be asymptomatic. The subject may have a genetic predisposition to the disease. A prophylactically effective amount of the antigen binding protein is administered to such an individual. A prophylactically effective amount is an amount which prevents or delays the onset of one or more aspects or symptoms of a disease described herein.

The methods, antigen binding proteins and compositions of the disclosure need not affect a complete cure, or eradicate every symptom or manifestation of the disease to constitute a viable therapeutic treatment. As is recognised in the art, drugs employed as therapeutic agents in methods of treatment may reduce the severity of a given disease state, but need not abolish every manifestation of the disease to be regarded as useful therapeutic agents. Similarly, a prophylactically administered treatment need not be completely effective in preventing the onset of a disease in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur (for example by delaying the onset of the disease) or worsen in a subject, is sufficient.

Another aspect of the disclosure is a method of treatment of a disease in a subject in need thereof comprising administering to said subject a therapeutically effective amount of the CD96 binding protein or the pharmaceutical composition as described in any one of the preceding aspects to the subject. A further aspect of the disclosure is the method of treatment described in the preceding aspect further comprising whether the subject expresses CD96.

Another aspect of the disclosure is a CD96 binding protein or a pharmaceutical composition as described in any one of the preceding aspects for use in therapy or for use in the treatment of a disease.

Another aspect of the disclosure is the use of a CD96 binding protein or a pharmaceutical composition as described in any one of the preceding claims in the manufacture of a medicament for use in the treatment of a disease.

Another aspect of the disclosure is a pharmaceutical composition comprising a therapeutically effective amount of a CD96 binding protein as described in any one of the preceding aspects.

One embodiment of the disclosure is a method for the treatment of a disease in a subject (such as a human subject) in need thereof comprising administering to said subject a therapeutically effective amount of the CD96 binding protein as described in any one of the preceding embodiments, or the pharmaceutical composition described in any one of the preceding embodiments to the subject.

One embodiment of the present disclosure is a method for the treatment of a disease in a subject in need thereof comprising administering to said subject a therapeutically effective amount of the CD96 binding or the pharmaceutical composition as described in any one of the preceding embodiments to the subject. A further embodiment of the present disclosure is a method for the treatment of a disease in a subject in need thereof further comprising determining whether the subject expresses CD96. An additional embodiment of the present disclosure is a CD96 binding protein or pharmaceutical as described in any one of the previous embodiments for use in therapy. An additional embodiment of the present disclosure is a CD96 binding protein or a pharmaceutical composition as described in any one of the preceding embodiments for use in the treatment of a disease. A further embodiment is the use of a CD96 binding protein or pharmaceutical composition described in any one of the preceding embodiments, in the manufacture of a medicament for use in the treatment of a disease. An additional embodiment of this disclosure is a method for the treatment of a disease, or a therapy, comprising administering to said subject a therapeutically effective amount of the CD96 binding or the pharmaceutical composition as described in any one of the preceding embodiments to the subject wherein the disease to be treated is a cancer. In a further aspect, the cancer is a solid tumour (e.g. a recurrent, metastatic or advanced solid tumour). The cancer can be: liver cancer (e.g. HCC), ovarian cancer, lung such as non-small cell lung cancer (NSCLC), renal cancer (e.g. RCC), colon cancer, gastric cancer, bladder cancer, head and neck squamous-cell carcinoma (HNSCC), or it can be leukemia, and/or any B cell malignancy.

EXAMPLES

Example 1

Generation of CD96 Binding Proteins
Binding Protein Generation

Fully human antibodies specific for human CD96 were isolated from naïve eukaryotic libraries using biotinylated recombinant human and cynomolgus CD96 combined with cell sorting and FACS-based selection techniques. The heavy chain outputs from the naïve eukaryotic library selections were shuffled against a light chain library and further selections were performed to identify the optimal light chain pairings.

Affinity maturation was performed to improve antibody affinity/potency. This involved integrating the CDRH3 of antibody 42Y073-86F08-1 (GAGYYGDKDPMDV of SEQ ID NO: 2) into pre-made libraries with diversity in CDRH1 or CDRH2. Further selections were performed on this diversified library and the lead molecules were identified and sequenced. Amino acid and nucleic acid sequences of variable light and heavy chains for the lead molecules are shown in SEQ ID NOS: 1-96. Amino acid sequences of the CDR regions are shown in SEQ ID NOS: 97-150.

Fc Selection

During the course of selection of lead molecules, the binding proteins were evaluated as human IgG1 WT molecules, or as Fc-disabled human IgG1 molecules. In order to make Fc-disabled molecules, amino acid residues at positions 234, 235, and 237, specifically, L234 and L235, or L235 and G237, were mutated to alanine, thus generating hIgG1 'LALA' (L234A/L235A), and hIgG1 'LAGA' (L235A/G237A) Fc-disabled human IgG1 molecules. These binding proteins exhibited CD96 binding and neutralisation of CD155 binding. Three CD96 binding proteins, 42Y073-86F08-66 (86F08-66), 42Y073-86F08-16 (86F08-16), and 42Y073-86F04-23 (86F04-23) were selected for further evaluation. The binding protein 42Y073-86F08-66 is also known as GSK 6097608 (a monoclonal antibody). These three CD96 binding proteins were evaluated with different IgG variants (human IgG1, IgG2, IgG4PE, or IgG1 Fc-disabled) for primary T cell binding, as well as CD155 neutralization activities. Variations in Fc did not affect binding to CD96-expressing cells, or neutralisation of CD155 binding to CD96-expressing cells, as indicated in FIG. 1.

Example 2

Characterization of CD96 Binding Proteins
Binding to CHO Cells Expressing Human or Cynomolgus Monkey CD96

CHO cells expressing human CD96v2 or cynomolgus monkey CD96v2 were prepared in PBS. The cynomolgus monkey CD96v2 cells were stained with 1 μM violet proliferation dye (VPD450). Cells were diluted in pre-warmed media (RPMI containing 10% foetal calf serum) and incubated for a further 10 minutes at 37° C. before centrifugation at 400 g, 5 minutes and resuspension in flow buffer (PBS+ 0.5% BSA+2 mM EDTA) to 1.5×106/ml. The stained CHO-cyCD96 and unstained CHO-huCD96 cells were combined and added to wells of a 384-well assay plate together with dilutions of test anti-CD96 binding proteins for 1 h at 4° C. Cells were further incubated with anti-IgG APC conjugate antibody and the amount of surface bound antibody on each of the CHO-cyCD96 and CHO-huCD96 cells was determined by flow cytometry. Median fluorescence intensity (MFI) values were fitted using a 4 parameter logistic model to calculate the EC50 of binding. Data is summarized in Table 2.

Neutralisation of Human CD155 Binding to CHO Cells Expressing Human CD96v2

CD96 binding proteins were prepared in PBS in U-bottomed 96-well plates. CHO cells expressing human CD96v2 were added and incubated for 30 minutes at room temperature. After washing cells three times by centrifugation, human CD155-Fc-AF647 conjugate was added for a further 30 minutes at room temperature. Following three washes, cells were fixed and analysed for levels of CD155-Fc-AF647 staining by flow cytometry. Median fluorescence intensity (MFI) values were fitted using a 4 parameter logistic model to calculate IC50 values. Data is summarized in Table 2.

Binding of CD96 Binding Proteins to Primary Human T Cells.

Human PBMCs were isolated from leukoreduction filters using density gradient centrifugation with Histopaque-1077. CD3+ T cells were subsequently isolated using a Pan T cell Isolation Kit (Miltenyi) following the manufacturer's instructions. Serial dilutions of test CD96 binding proteins were incubated with the human T cells for 1 h at 4° C. Following three washes in buffer, anti-human IgG-APC conjugate was added for 1 h at 4° C. Following three washes, cells were fixed and analysed for APC staining by flow cytometry. Median fluorescence intensity (MFI) values were fitted using a 4 parameter logistic model to calculate the EC50 of binding. Data is summarized in Table 2

TABLE 2

Binding data and neutralization of human CD155 binding to hCD96v2 expressing CHO cells by CD96 binding proteins

| Clone | Lineage | CHO-huCD96 EC50 (nM) | CHO-cyCD96 EC50 (nM) | Neutralization IC50 (nM) | T cell binding EC50 (nM) |
|---|---|---|---|---|---|
| 42Y073-1A01-85 | 1A01 | 0.47 | 0.01 | 0.03 | 0.32 |
| 42Y073-1A01-97 | 1A01 | 0.77 | 0.02 | 0.03 | ND |
| 42Y073-1A01-100 | 1A01 | 0.02 | 0.04 | 0.06 | 0.01 |
| 42Y073-1A01-103 | 1A01 | 0.02 | 0.03 | 0.03 | 0.01 |
| 42Y073-1A01-126 | 1A01 | 0.02 | 0.03 | 0.10 | ND |
| 42Y073-1A01-191 | 1A01 | 0.01 | 0.02 | 0.03 | 0.38 |
| 42Y073-86F04-3 | 86F04 | 0.04 | 0.04 | 0.31 | 0.09 |

TABLE 2-continued

Binding data and neutralization of human CD155 binding to hCD96v2 expressing CHO cells by CD96 binding proteins

| Clone | Lineage | CHO-huCD96 EC50 (nM) | CHO-cyCD96 EC50 (nM) | Neutralization IC50 (nM) | T cell binding EC50 (nM) |
|---|---|---|---|---|---|
| 42Y073-86F04-4 | 86F04 | 0.04 | 0.07 | 0.16 | 0.05 |
| 42Y073-86F04-5 | 86F04 | 0.05 | 0.07 | 0.30 | 0.05 |
| 42Y073-86F04-6 | 86F04 | 0.06 | 0.11 | 0.25 | 0.01 |
| 42Y073-86F04-18 | 86F04 | 0.07 | 0.11 | 0.59 | 0.01 |
| 42Y073-86F04-23 | 86F04 | 0.06 | 0.03 | 0.76 | 0.01 |
| 42Y073-86F04-33 | 86F04 | 0.04 | 0.05 | 0.71 | 0.06 |
| 42Y073-86F04-88 | 86F04 | 0.05 | 0.16 | 0.21 | 0.06 |
| 42Y073-86F08-1 | 86F08 | 0.07 | 0.00 | 0.33 | 0.05 |
| 42Y073-86F08-3 | 86F08 | 0.04 | 0.08 | 0.28 | 0.05 |
| 42Y073-86F08-4 | 86F08 | 0.04 | 0.07 | 0.38 | 0.01 |
| 42Y073-86F08-8 | 86F08 | 0.17 | 0.03 | 0.93 | 0.04 |
| 42Y073-86F08-16 | 86F08 | 0.03 | 0.04 | 0.78 | 0.01 |
| 42Y073-86F08-17 | 86F08 | 0.10 | 0.03 | 0.52 | 0.01 |
| 42Y073-86F08-22 | 86F08 | 0.03 | 0.09 | 0.41 | 0.18 |
| 42Y073-86F08-47 | 86F08 | 0.05 | 0.06 | 0.17 | 0.03 |
| 42Y073-86F08-66 | 86F08 | 0.05 | 0.02 | 1.55 | 0.01 |
| 42Y073-2B04-46 | 2B04 | 1.06 | 0.04 | 0.40 | ND |

Selection of 42Y073-86F08-66 for Further Characterisation

To aid the selection of lead molecules, the biophysical properties of the anti-CD96 binding proteins were assessed. Namely the immunogenicity, deamidation, glycosylation, oxidation, aspartate isomerisation were predicted by in silico analysis and the aggregation, fragmentation and chemical degradation properties were assessed in the following conditions: 50 mM sodium phosphate pH 7.5 and 50 mM sodium acetate pH 5.0 at either 10 mg/ml or 1 mg/ml, and unstressed and stressed (thermal stress at 40° C. for 2 weeks) conditions. Anti-CD96 binding proteins were expressed in a HEK transient system and purified using Protein-A affinity and size exclusion chromatography. Anti-CD96 binding proteins were scored as follows:

TABLE 3

Sample preparation risk:
Percentage Recoveries

| Criteria | Low | Potential | High |
|---|---|---|---|
| Post-Dialysis | >80% | 80-70% | <70% |
| Post-Incubation | >98% | 95-98% | <95% |

TABLE 4

Aggregation & fragmentation risk by aSEC (analytical size exclusion chromatography):

| Characterisitic | Low | Potential | High |
|---|---|---|---|
| Total % Monomer | >95.0% | 94-95% | <94% |
| Total % HMwS | <5.0% | 5.0-5.5% | >5.5% |
| Total % LMwS | <2.5% | 2.5-3% | >3% |

TABLE 5

Aggregation risk by DLS (dynamic light scattering):

| Characterisitic | Low | Potential | High |
|---|---|---|---|
| Average Rh* (nm) | 4.5-7 | 7-8 | >8 |
| Average % Mass | >98% | N/A | <98% |

*Rh = hydrodynamic radii

Antigen Binding by BIAcore:

A change in antigen binding within ±10% between unstressed and stressed samples was considered an acceptable range (low risk). Molecules outside of this range could indicate a potential risk due to loss in binding activity.

Data is summarised in Tables 6 and 7. In Table 6, the position of the predicted risk in the sequence is identified (Kabat numbering). In Table 7, the following abbreviations are used for risks observed and the conditions under which they were observed: Agg=aggregation; incr. % Mass=increase in heterogeneity; Binding loss=a binding loss of greater than the assay limit was observed; Binding incr.=an increase in binding (indicates a possible propensity to aggregate); HMwS=High molecular weight species; LMwS=Low molecular weight species; Rh=hydrodynamic radius (where a larger radius indicates possible aggregation); PBS=phosphate buffer saline; U=unstressed; S=stressed; A=50 mM sodium acetate pH 5.0; and P=50 mM sodium phosphate pH 7.5.

42Y073-86F08-66, 42Y073-86F08-16 and 42Y073-86F04-23 demonstrated minimal development liabilities and minimal in silico risks. However, 42Y073-86F08-66 was selected for progression and further characterisation because the following attributes were observed:

An acceptable level of percentage total high molecular weight species (HMwS; <5%), low molecular weight species (LMwS; <2.5%) and monomer (95%), as determined by analytical size exclusion chromatography (aSEC);

Expected values for size distribution (>98% in Peak 2 of SEC) and hydrodynamic radius (4.5-7 nm), as determined by dynamic light scattering (DLS);

Minimal unexpected changes to chemical heterogeneity between unstressed and stressed as determined by capillary isoelectric focussing (cIEF); and For antigen binding <10% change was determined by the antigen binding assay.

TABLE 6

In silico biophysical analysis results of CD96 binding proteins

|  | Oxidation | De-amidation | Isomerization | Other |
|---|---|---|---|---|
| 42Y073-86F04-3 | Potential (H_cdr2:54) | Low | Low | Low |
| 42Y073-86F04-5 | Low | Low | Low | Low |
| 42Y073-86F04-18 | Potential (H_cdr2:54) | Low | Low | Low |
| 42Y073-86F04-23 | Potential (H_cdr2:54) | Low | Low | Low |
| 42Y073-86F04-33 | Low | Low | Low | Low |
| 42Y073-86F08-3 | Low | Low | Low | Potential (DP motif H_cdr3:100C) |
| 42Y073-86F08-4 | Low | Low | Low | Potential (DP motif H_cdr3:100C) |
| 42Y073-86F08-16 | Low | Low | Low | Potential (DP motif H_cdr3:100C) |
| 42Y073-86F08-22 | Low | Low | Low | Potential (DP motif H_cdr3:100C) |
| 42Y073-86F08-47 | Low | Low | Low | Potential (DP motif H_cdr3:100C) |
| 42Y073-2B04-46 | Low | Low | Potential (H_cdr2:52) | Low |
| 42Y073-1A01-85 | Low | Low | Low | Potential (DP motif H_cdr3:101) |
| 42Y073-1A01-100 | Low | Low | Low | Potential (DP motif H_cdr3:101) |
| 42Y073-1A01-103 | Low | Low | Low | Potential (DP motif H_cdr3:101) |
| 42Y073-1A01-126 | Low | Low | Low | Potential (DP motif H_cdr3:101) |
| 42Y073-86F08-66 | Low (H_cdr3:100E, H_fr2:48) | Low | Low | Potential (DP motif H_cdr3:100C) |
| 42Y073-86F08-16 | Low | Low | Low | Potential (DP motif H_cdr3:100C) |
| 42Y073-86F04-23 | Potential (H_cdr2:54) | Low | Low | Low |

TABLE 7

Further biophysical analysis results of CD96 binding proteins

|  | Sample preparation | Aggregation & Fragmentation (aSEC) | Aggregation (DLS) | Antigen binding | cIEF |
|---|---|---|---|---|---|
| 42Y073-86F04-3 | Low | Low | High (Agg in U, S, A & P and incr. % Mass in U, S & P) | Low | Low |
| 42Y073-86F04-5 | Low | Low | Potential (Agg and incr. % Mass in U, S & P) | Low | Low |
| 42Y073-86F04-18 | Low | Low | Low | Low | Low |
| 42Y073-86F04-23 | Low | Low | Low | Low | Low |
| 42Y073-86F04-33 | Low | Low | Low | Low | Low |
| 42Y073-86F08-3 | Low | Low | Low | Potential (11% Binding loss in S & A) | Low |
| 42Y073-86F08-4 | Low | High (HMwS in S & A) | Low | High (37% Binding loss in S & A) | Low |

TABLE 7-continued

Further biophysical analysis results of CD96 binding proteins

| | Sample preparation | Aggregation & Fragmentation (aSEC) | Aggregation (DLS) | Antigen binding | cIEF |
|---|---|---|---|---|---|
| 42Y073-86F08-16 | Low | Low | Low | Low (9.57% Binding incr. in S & P) | Low |
| 42Y073-86F08-22 | Low | High (HMwS in S & A) | Low | High (41% Binding loss in S & A) | Low |
| 42Y073-86F08-47 | Low | Low | Low | Potential (34% Binding incr. in S & P) | Low |
| 42Y073-2B04-46 | High (Yield loss in PBS) | High (HMwS and LMwS in U, S & A) | High (Agg and incr. % Mass in S, A) | High (36% Binding loss in S & A) | Low |
| 42Y073-1A01-85 | Low | Low | Low | Low (9.99% Binding loss in S & P) | Low |
| 42Y073-1A01-100 | Low | Low | Low | Low | Low |
| 42Y073-1A01-103 | Low | Low | Low | Low | Low |
| 42Y073-1A01-126 | Low | Low | Low | Potential (13% Binding loss in S & P) | Low |
| 42Y073-86F08-66 | Low | Low | Low | Potential (12% Binding loss in S & A) | Low |
| 42Y073-86F08-16 | Low | Low | Low | Low (Binding loss in A) | Low |
| 42Y073-86F04-23 | Potential (74.3% recovery in U & A) | Low (LMwS in S) | Low (Rh in U, S & P) | Low | Low |

Epitope Binning of CD96 Binding Proteins

Epitope binning competition assays were conducted to determine the epitopes of CD96 to which the anti-CD96 binding proteins presented herein bind. Briefly, HuCD96-His was incubated with a first CD96 binding protein at room temperature for 1 hour, before measuring binding of a second binding protein captured on a Protein A sensor by BLI. If binding of the second CD96 binding protein was observed, the two binding proteins were deemed to be non-competitive and assigned to different epitope bins. If no binding of the second CD96 binding protein could be seen, the two binding proteins were deemed to be competitive and assigned to the same epitope bin. A self-binning control was included for each CD96 binding protein, using the same binding protein as both the first and the second binding protein.

Competition between all CD96 binding proteins was observed, except for 42Y073-2B04-46, indicating that all except 42Y073-2B04-46 bind similar epitopes of CD96. This data suggests that, with the exception of 42Y073-2B04-46, all CD96 binding proteins presented herein bind to the same epitope of CD96 or to spatially close epitopes such that binding of further CD96 binding proteins is inhibited (i.e. they belong to the same epitope bin). However, the finding that 42Y073-2B04-46 does not compete with the other CD96 binding proteins presented herein suggests that this clone binds a distinct epitope of CD96 (and thus belongs to a distinct epitope bin). Thus, together with the data presented in Table 2, it will be appreciated that the binding and neutralization of human CD155 binding to hCD96v2 expressing CHO cells by the CD96 binding proteins presented herein is not limited to the binding to any particular epitope of CD96.

Further Binding Affinity Studies of CD96 Binding Proteins to CD96 Isoforms

The binding affinity of 42Y073-86F08-66, a fully human IgG1 antibody with wild-type Fc, expressed and purified from CHO cells, to recombinant CD96 was determined using solution equilibrium titration (MSD-SET) assays. 42Y073-86F08-66 bound to recombinant human CD96v2 with a mean KD of 20 pM, and to recombinant cynomolgus monkey CD96v2 with a mean KD of 278 pM (FIG. 2). In addition, it was demonstrated that 42Y073-86F08-66 bound to recombinant murine CD96v2 with a mean KD of 479 pM.

In surface plasmon resonance (SPR) assays, 42Y073-86F08-66 did not bind to recombinant human CD155, human CD226, human TIGIT or human nectin-1, which are homologs in the pathway.

MSD-SET Assays Procedure:

Summary: MSD-SET (MSD solution equilibrium titration) analysis was used in order to determine the affinities of these antibodies to human and mouse CD96 proteins at 25° C. as the dissociation rates were too slow to measure by BIACORE at this temperature. MSD-SET determines the solution phase, equilibrium affinity of antibodies. The method relies on the detection of free antigen at equilibrium in a titrated series of antibody concentrations.

Procedure:

Biotinylated human CD96 protein was used at a constant concentration of 1.5 nM and cynomolgus monkey biotinylated CD96 protein at 3 nM. Antibody samples were titrated 1 in 5 over a 22 point curve from 6 nM for the human CD96 and cynomolgus monkey CD96. The titrated antibody and CD96 protein were incubated for 24 h at room temperature. After 24 h, 5 nM antibodies were coated onto standard bind MSD plates (Meso Scale Discovery, L15XA) for 30 min at room temperature. Plates were then blocked with STARTING BLOCK blocking buffer (Thermo Scientific, #37542) for 30 min with shaking at 700 rpm, followed by three washes with wash buffer. The incubated solutions were added to the MSD plates for 150 s with shaking at 700 rpm followed by one wash. Antigen captured on a plate was detected with a SULFOTAG-labelled streptavidin (Meso Scale Discovery, R32AD-1) by incubation on the plate for 3 min. The plates were washed three times with wash buffer and then read on an MSD SECTOR IMAGER instrument using 1× Read Buffer T with surfactant (Meso Scale Discovery, R92TC-1). The percent free antigen was plotted as a function of titrated antibody using GRAPHPAD PRISM software and fitted to a quadratic equation.

CD96 Binding Proteins Binding to HEK Cells Overexpressing CD96 Proteins

Figure 3A:
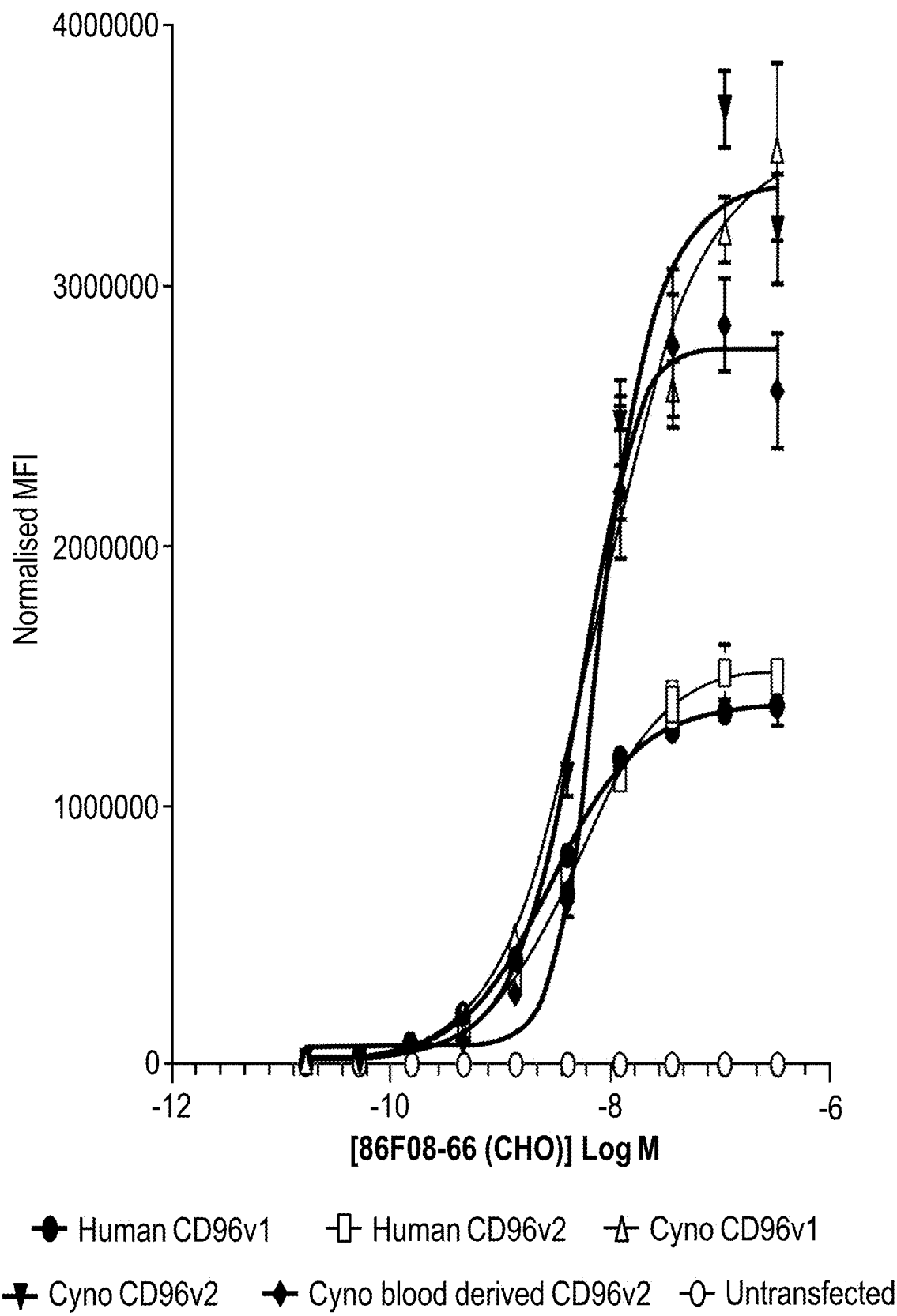
FIGS. 3A, 3B and 3C show binding of CD96 binding protein to HEK cells transiently transfected with human or cynomolgus monkey CD96 isoforms.
Figure 3B:
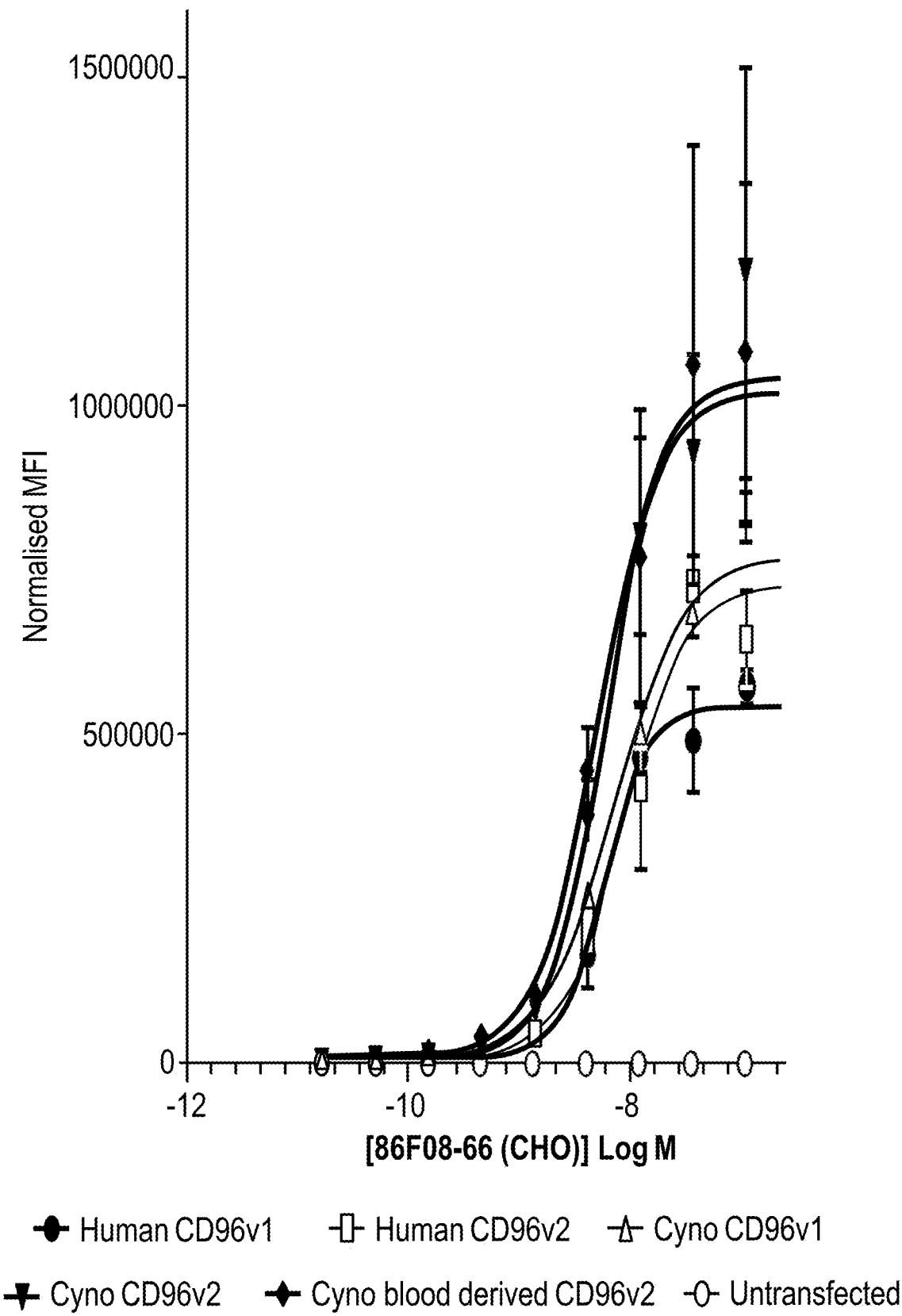
Figure 3C:
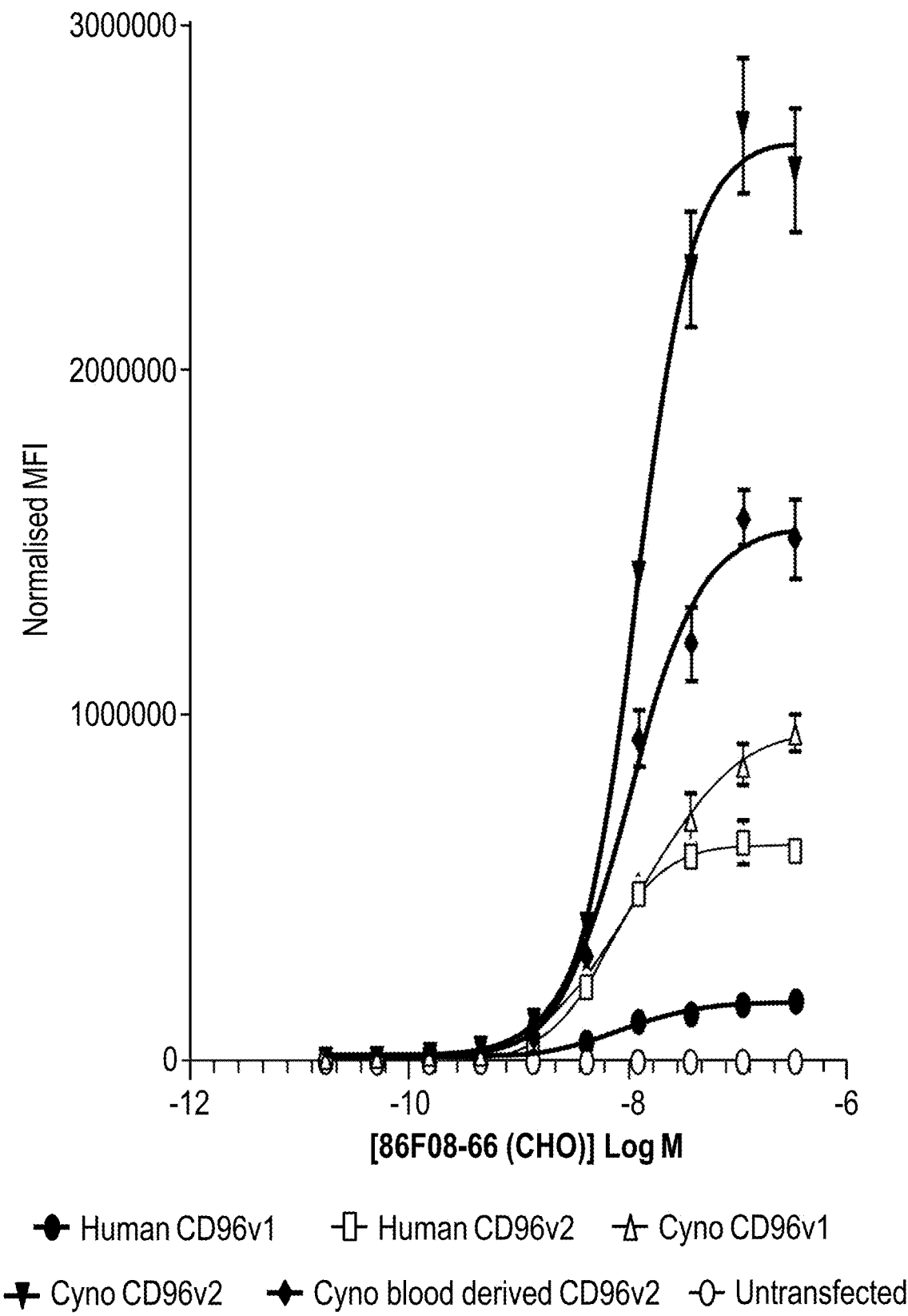

The binding of 42Y073-86F08-66 to the known isoforms of human or cynomolgus monkey CD96 on cell membranes was determined by flow cytometry using HEK cells that had been transfected with these different isoforms (FIG. 3). Despite the differences in maximum binding response to the expressed isoforms, and between experiments (most likely due to variation in expression efficiency), comparable binding activities as indicated by the EC50 of 42Y073-86F08-66 have been demonstrated to these CD96 isoforms (Table 8). Taken together these data suggest that 42Y073-86F08-66 is capable of recognising all membrane forms of CD96 presented in human and cynomolgus monkey.

TABLE 8

Potency of 42Y073-86F08-66 for binding to HEK cells transiently transfected with CD96 isoforms

| | Human CD96v1 | Human CD96v2 | Cyno CD96v1 | Cyno CD96v2 | Blood derived Cyno CD96v2 |
| --- | --- | --- | --- | --- | --- |
| Geometric mean EC50 (Range) nM (n = 3) | 5.28 (3.13-8.89) | 6.44 (4.72-8.78) | 9.17 (6.83-12.3) | 7.88 (5.54-11.21) | 7.34 (5.27-10.23) |

Figure 4:
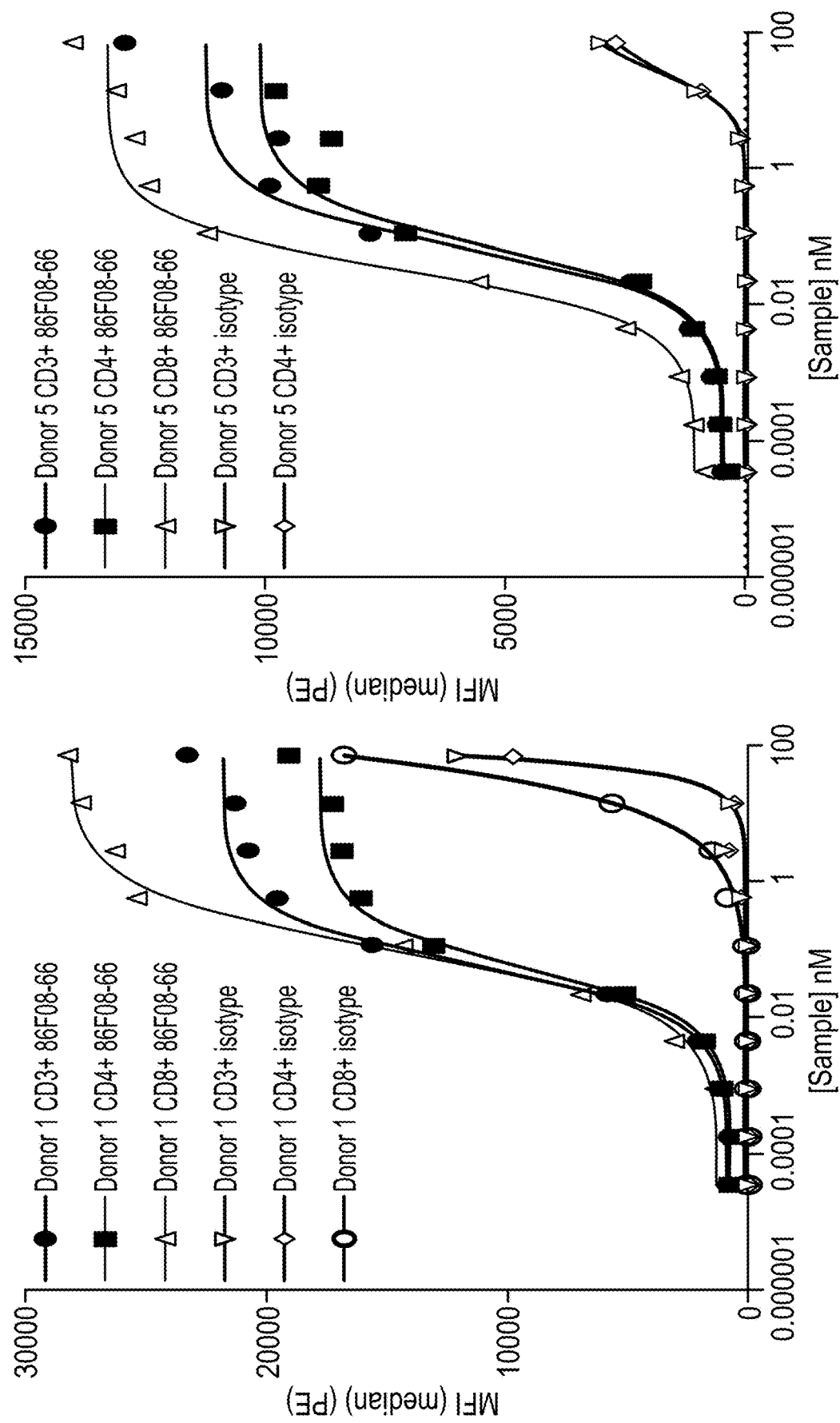
FIG. 4 shows binding of CD96 binding protein (vs isotype control) to primary human T cells (total $CD3^+$ T cells vs $CD4^+$ or $CD8^+$ subsets).

Binding Affinity of CD96 Binding Proteins to Native CD96 on Human and Cynomolgus Monkey T Cells To confirm that 42Y073-86F08-66 binds to native CD96 expressed on primary human and monkey cells, the binding of 42Y073-86F08-66 to CD3$^+$ T cells and subsets (CD4$^+$ or CD8$^+$) in both species was determined by flow cytometry. 42Y073-86F08-66 bound with high affinity to human CD4$^+$ and CD8$^+$ T cells (EC50s of 47 pm and 45 pM respectively) (FIG. 4 and Table 9). 42Y073-86F08-66 has a higher potency (pM) for binding to primary human T cells compared with HEK cells that over-express CD96 (nM) as a result of the relatively low expression of CD96 on primary cells compared with the expression of CD96 after transient transfection of CD96 isoforms under the control of a strong, constitutive promoter element.

TABLE 9

Potency of 42Y073-86F08-66 to primary human T cells (total CD3$^+$ T cells vs CD4$^+$ or CD8$^+$ subsets)

| | Human total CD3+ T cells | Human CD4$^+$ T cells | Human CD8$^+$ T cells |
| --- | --- | --- | --- |
| Geometric mean EC50 (Range) pM (n = 6) | 49.9 (39.6-62.6) | 47.0 (37.7-58.5) | 44.7 (31.6-63.3) |

Figure 5:
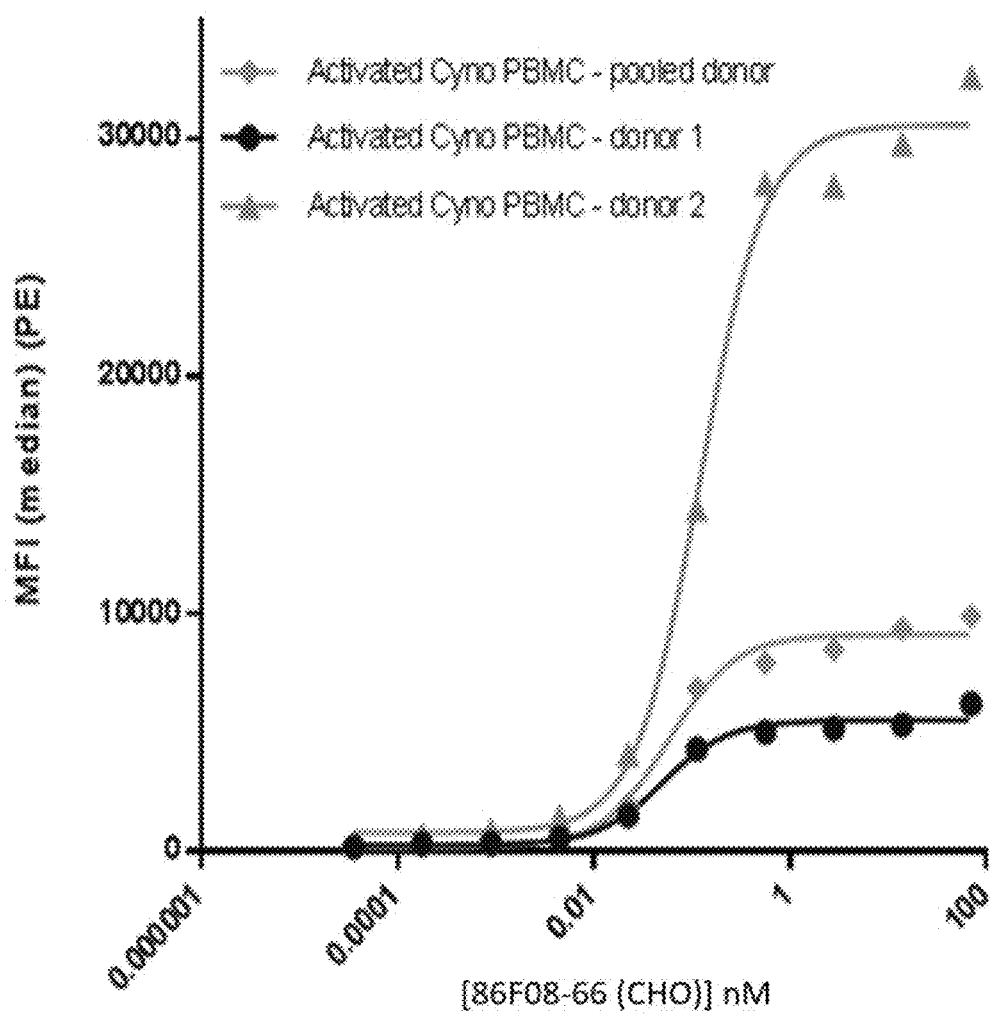
FIG. 5 shows binding of CD96 binding protein to activated primary cynomolgus monkey T cells.

To confirm that 42Y073-86F08-66 binds to CD96 in cynomolgus monkeys, binding to primary monkey T cells was determined. Based on the binding of 42Y073-86F08-66 and a commercially available anti-CD96 antibody 6F9, cynomolgus monkey T cells were found to express much lower levels of CD96 compared with human T cells. A similar observation was made for rhesus monkey T cells. To robustly quantify CD96 target engagement, purified cynomolgus monkey CD3$^+$ T cells were activated using anti-CD2/3/28 beads for 17 days to upregulate CD96 expression. 42Y073-86F08-66 binding was determined for 3 different activated T cell samples from cynomolgus monkeys, and 42Y073-86F08-66 binding was confirmed in all these samples. While there was a differential maximal signal among samples, the EC50s were very similar (mean 76.6 pM), and within 2-fold of that observed for human T cells (49.9 pM) (FIG. 5).

Internalisation of CD96 Binding Proteins Upon Binding to Human T Cells and NK Cells The fate of 42Y073-86F08-66 following binding was determined in human PBMC cultures from 3 donors using imaging cytometry. Highly punctate staining with 42Y073-86F08-66 was observed on the cell membrane in all 3 cell populations (CD4$^+$ T cells, CD8$^+$ T cells and NK cells) from all 3 donors at baseline, and this staining pattern remained across the 45 hour time-course (FIG. 6). In all three cell populations defined (CD4$^+$, CD8$^+$ and NK cells) the internalisation of 42Y073-86F08-66-PE was slow, and not complete over a 45 hour time course. These data suggest that 42Y073-86F08-66 internalisation is slow relative to other antibodies that target T cell surface receptors.

Figure 7:
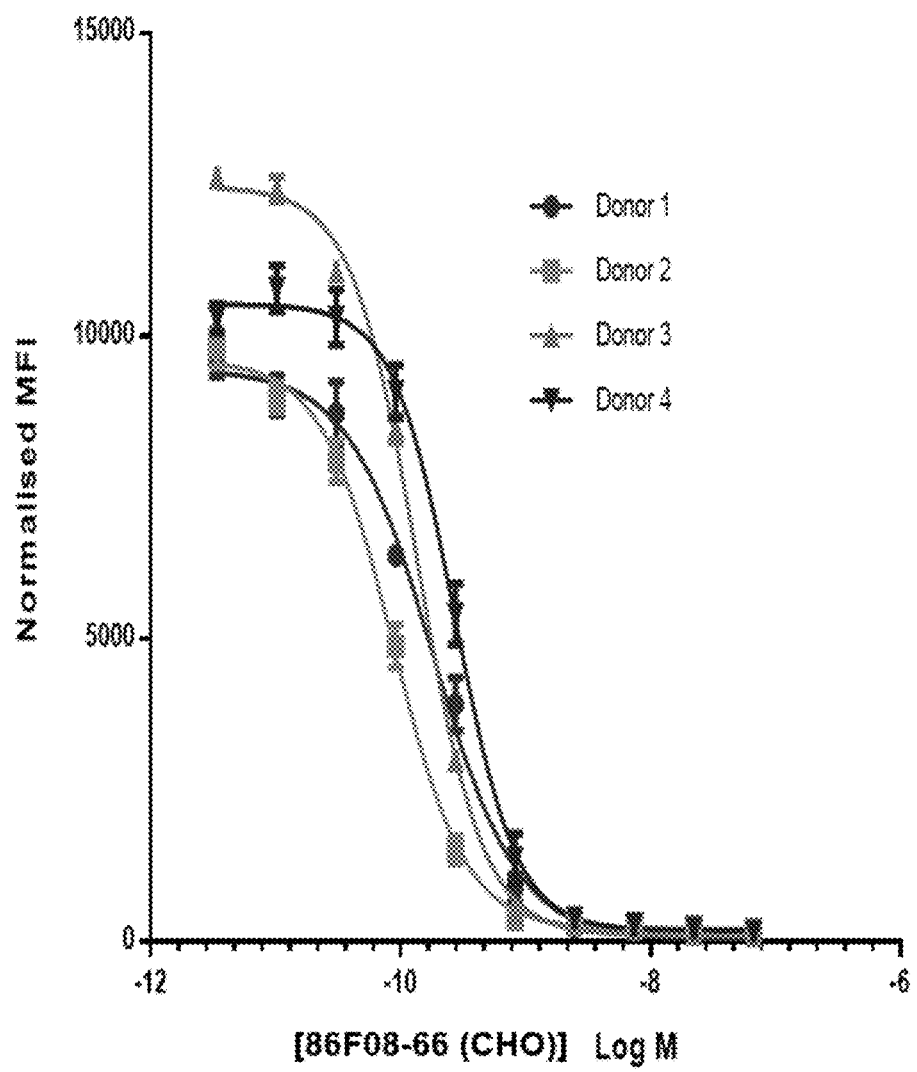
FIG. 7 shows CD96 binding protein, when pre-complexed to membrane CD96 in primary human T cells, preventing the binding of CD155:Fc to said T cells.

CD96 Binding Proteins Inhibits Binding of CD96 Ligand CD155 to CD96-Expressing Cells In primary human T cells it was demonstrated that pre-complexation of 42Y073-86F08-66 to membrane CD96 inhibited the latter from binding to its ligand (recombinant human CD155:Fc) (IC50 0.16 nM) (FIG. 7).

Disruption of Established CD96:CD155 Interactions by CD96 Binding Proteins

Figure 8:
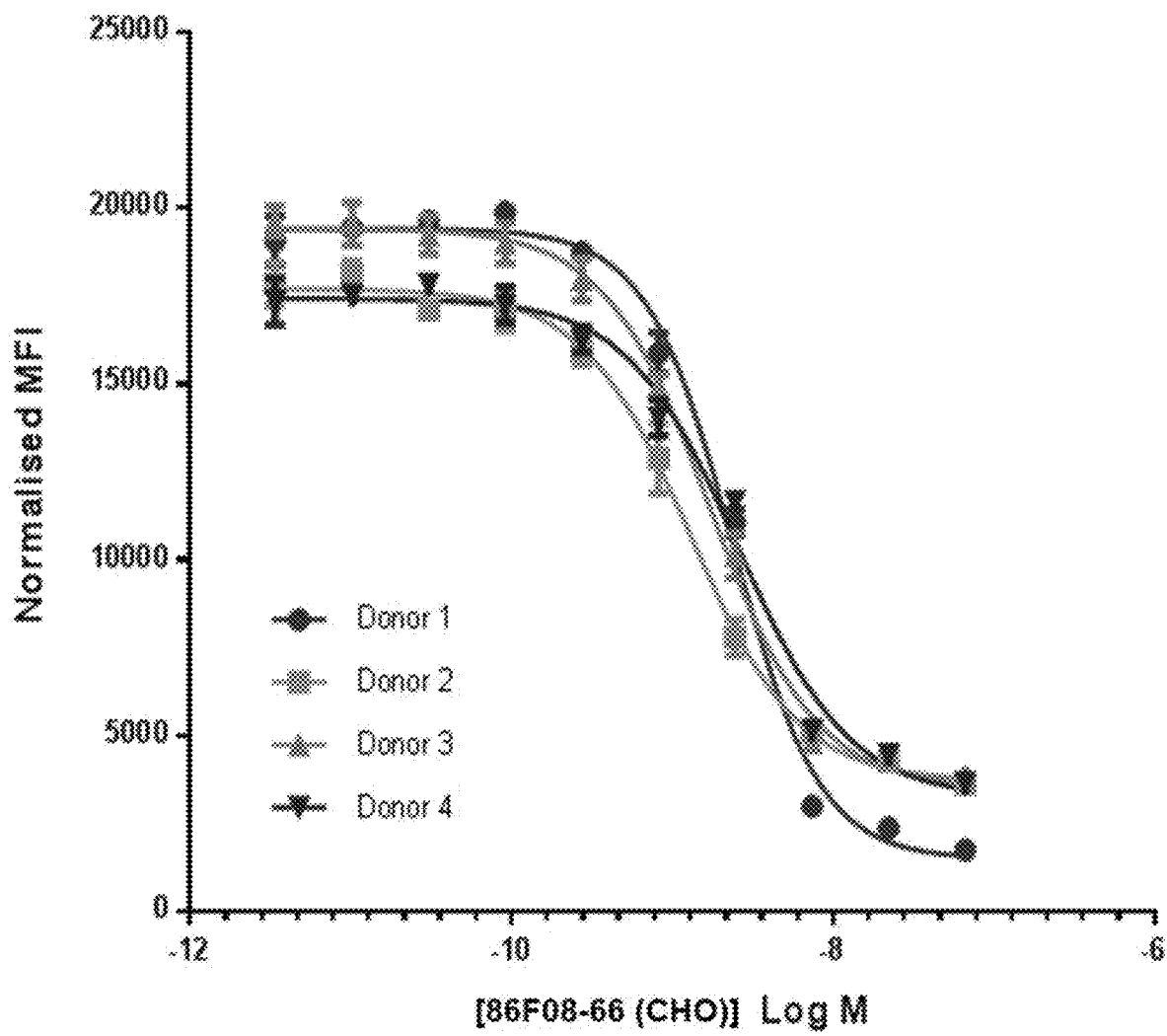
FIG. 8 shows the displacement of CD155:Fc that has been pre-bound to human T cells by CD96 binding protein.

When CD155:Fc was pre-bound to primary human T cells, 42Y073-86F08-66 could compete-off CD155 in a dose-dependent manner (IC50 1.93 nM) (FIG. 8), indicating that 42Y073-86F08-66 can displace CD96-bound CD155, the natural ligand for CD96.

Fc Receptor Engagement by CD96 Binding Proteins

Since 42Y073-86F08-66 is a fully human IgG1 antibody with a WT Fc, it is expected to bind to relevant Fc receptors.

Figure 9:
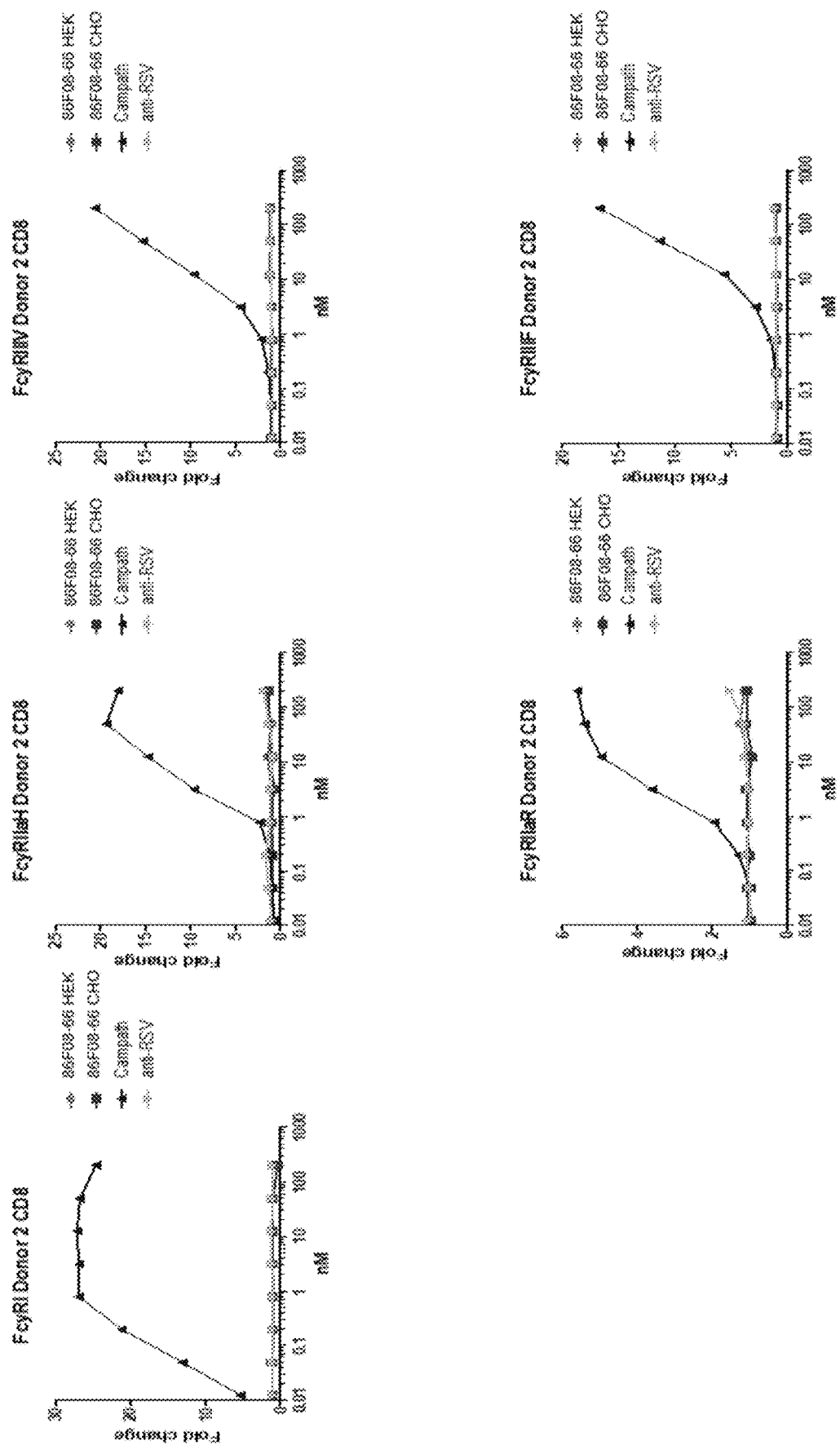
FIG. 9 shows human Fcγ reporter assay data, demonstrating that binding of CD96 binding proteins to CD96 on primary human T cells does not induce cross-linking and/or signaling via Fcγ receptors.

Using a panel of recombinant cell lines (Promega) expressing activatory human Fcγ receptor reporters (FcγRI, FcγRIIa(R), FcγRIIa(H), FcγRIIIa(V) and FcγRIIIa(F)) we demonstrated that the binding of 42Y073-86F08-66 to CD96 on primary human T cells did not result in the activation of human Fcγ receptors (FIG. 9). In contract, a control anti-CD52 antibody (Campath) efficiently elicited FcγR activation signals with all of the Fcγ receptor-expressing cells tested.

Figure 10:
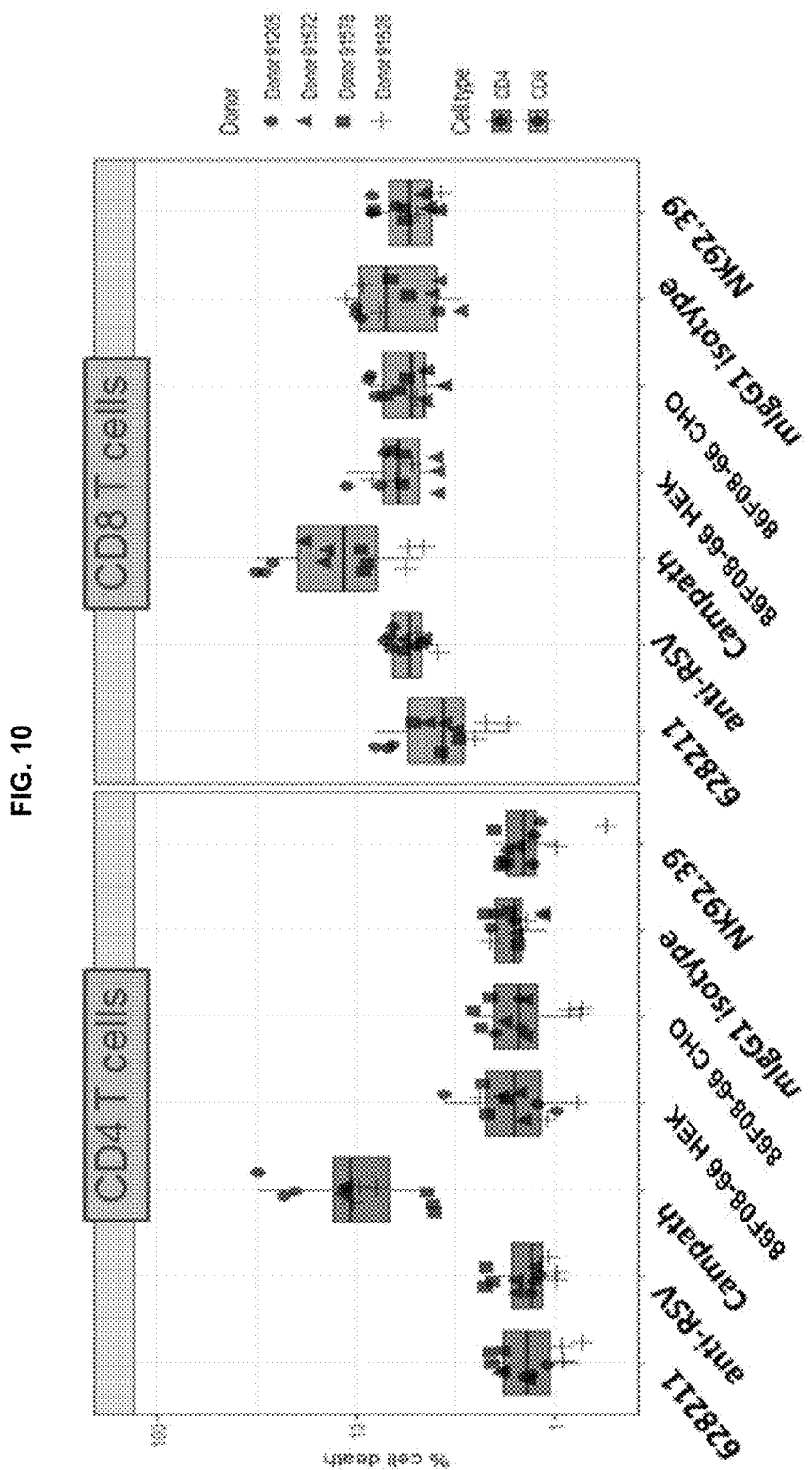
FIG. 10 shows human ADCC target cell killing assay data in $CD4^+$ and $CD8^+$ T cells; no evidence of increased cell death was observed in either $CD4^+$ or $CD8^+$ T cells in the presence of CD96 binding proteins.

It was important to confirm the findings of the reporter assays by cell killing assays using primary human cells. In fresh human PBMC cultures containing NK cells, there was no evidence of increased cell death of either CD4 or CD8 T cells in the presence of 42Y073-86F08-66 (FIG. 10). In the same experiments both CD4 and CD8 T cells were effectively depleted in the presence of the anti-CD52 antibody (Campath).

The first step of the classical pathway of complement activation is mediated by the binding of complement component C1q to cells that are opsonised with antibodies. The affinity of human complement component C1q binding to 42Y073-86F08-66 was determined using SPR and was higher (KD 94.4 nM) than that of the IgG1 WT isotype control (KD 643.5 nM). The potential for 42Y073-86F08-66 to induce complement-dependent cytotoxicity (CDC) was investigated using primary human T cells as targets.

Figure 11:
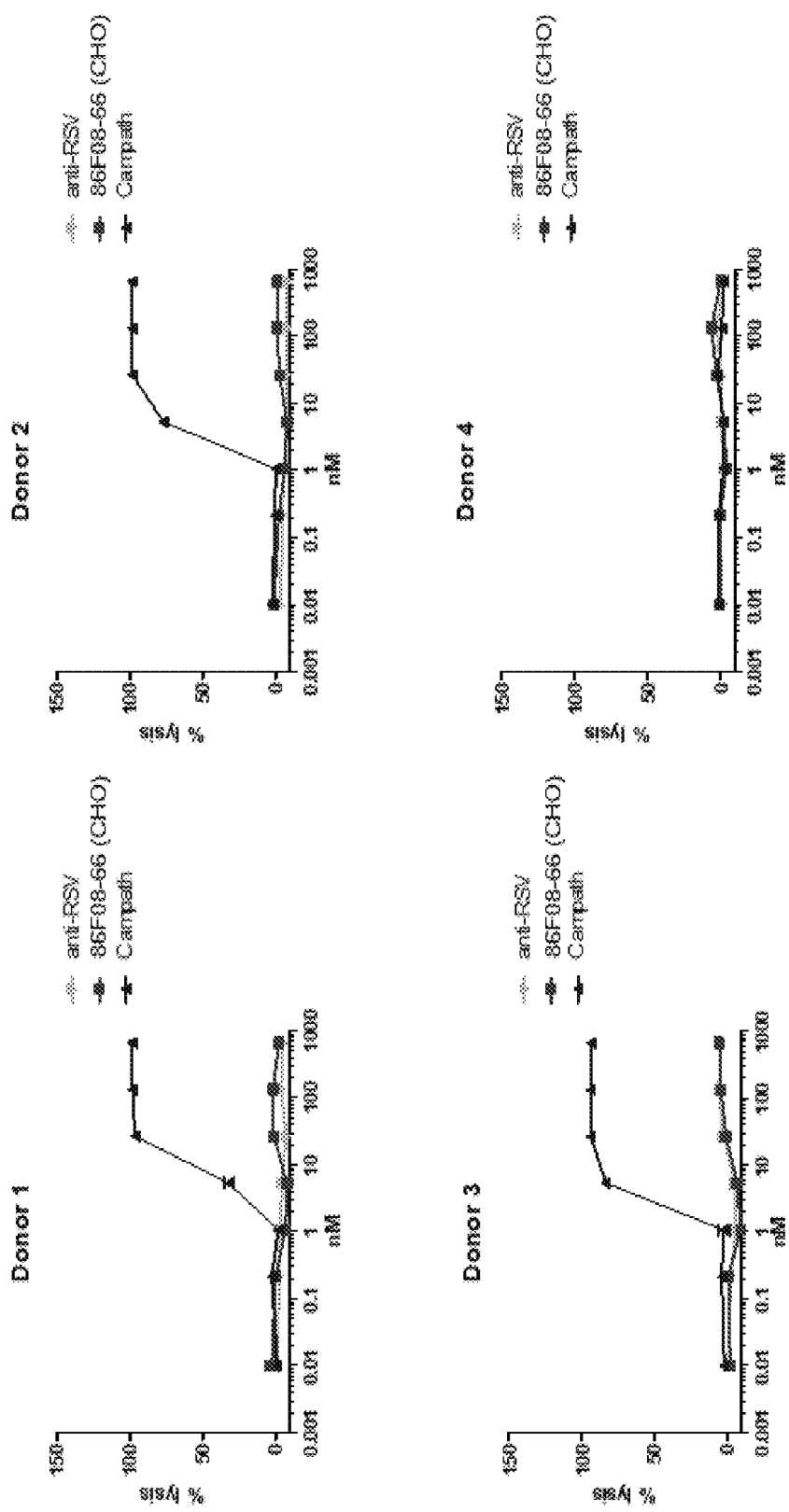
FIG. 11 shows human CDC target cell killing assay in $CD4^+$ T cells; no evidence of induced complement-dependent cellular toxicity is observed from CD96 binding protein.

In CDC assays employing human serum as a source of complement, there was no evidence of depletion of either CD4 or CD8 T cells by 42Y073-86F08-66, whereas a control anti-CD52 antibody efficiently mediated depletion of both subsets (FIG. 11). Taken together these data suggest that the risk of ADCC or CDC-mediated depletion of CD96 expressing T cells decorated with 42Y073-86F08-66 is insignificant.

Example 3

In vitro Efficacy and Mechanism Studies of CD96 Binding Proteins

In vitro Efficacy of 42Y073-86F08-66 in a Primary Mixed Human PBMC-MLR Assay

The effect of 42Y073-86F08-66, expressed and purified from CHO cells, and from HEK cells was tested in a primary PBMC assay with no addition of CD155, anti-CD3 or anti-TIGIT. For this assay, PBMCs from 8 different human donors were mixed together and added to the well with different antibodies in solution. After incubation for 3 days, IFNγ in the supernatant was measured by using the homogenous time resolved fluorescence (HTRF) detection method. In this assay, anti-CD3 was not required as PBMCs were activated by the MHC mismatch among different donors. The potency was similar for both CD96 binding proteins (expressed in CHO or HEK cells) (FIG. 12). Both appeared to be more potent than Tecentriq (EC50 49 pM). In a separate repeat of the same experiment, the EC50s were 22 pM, 10 pM and 140 pM for 42Y073-86F08-66 (HEK), 42Y073-86F08-66 (CHO) and Tecentriq respectively (FIG. 12). The cell viability was also measured at the end of 3 days, and only Tecentriq showed some reduced cell viability. None of the anti-CD96 mAbs or isotype controls reduced cell viability, consistent with the observed lack of cell depletion in the ADCC assays.

Figure 13:
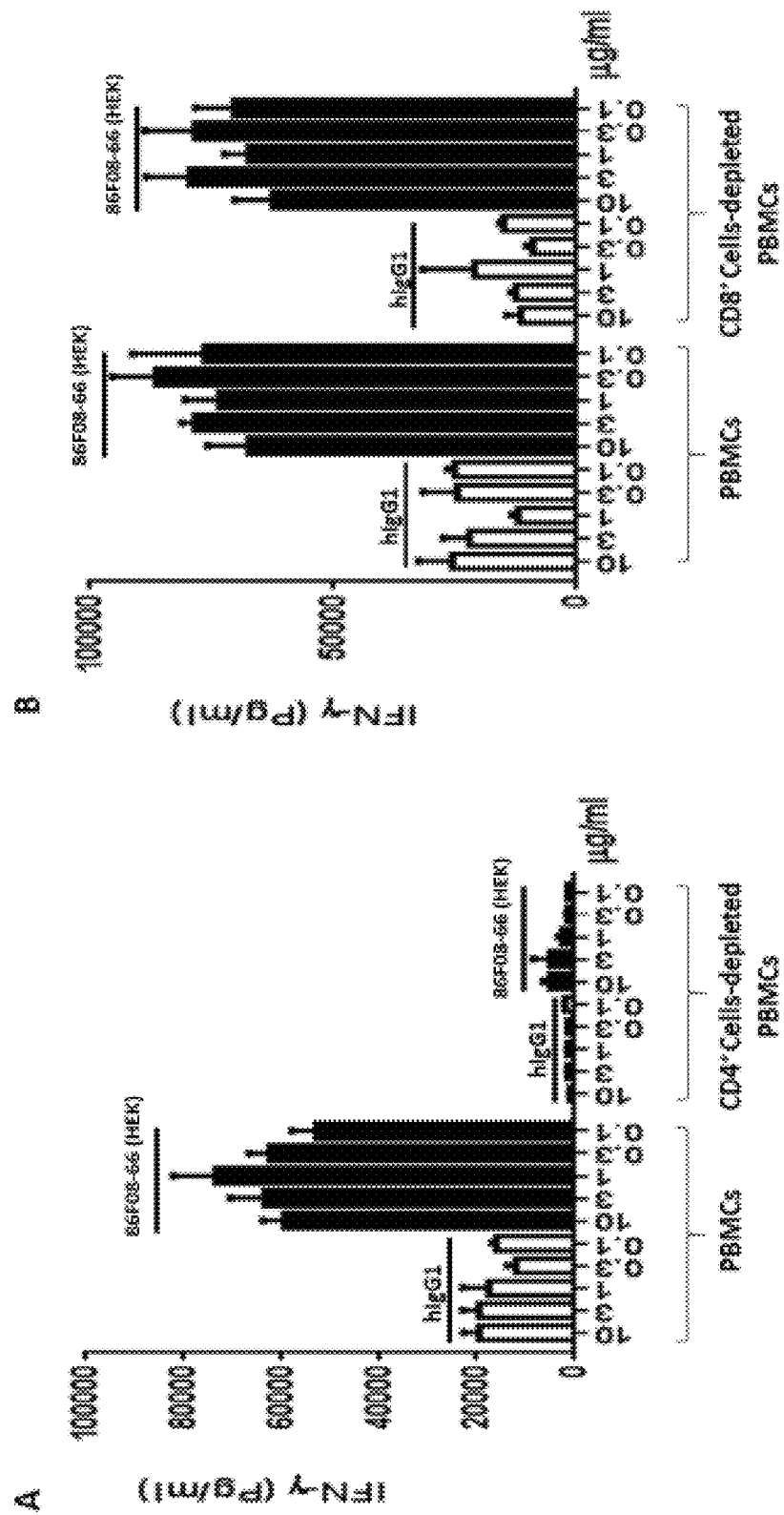
FIG. 13 shows activity of CD96 binding protein (expressed from HEK cells) on IFNγ production in a mixed PBMC-MLR assay, with or without $CD4^+$ (A) or $CD8^+$ (B) T cells.

$CD4^+$ T Cells are the Major Source of 42Y073-86F08-66-Induced IFNγ in the Mixed Human PBMC-MLR Assay To address the question of what cell sub-populations are responsible for the observed increase of secreted IFNγ in the supernatant upon 42Y073-86F08-66 (HEK) and 42Y073-86F08-66 (CHO) treatment in the PBMC assays, cell depletion studies were carried out. PBMCs from 4 different donors were depleted of $CD4^+$ T cells or $CD8^+$ T cells separately before mixing together for lymphocyte activation and antibody treatment. Human CD4 or CD8 MicroBeads (Miltenyi) were used to carry out the depletion, and the purity of $CD4^+$ or $CD8^+$ T cell depletion was validated by flow cytometry. $CD4^+$ cells were depleted from PBMCs by 98.5-99.5%, and $CD8^+$ cells were depleted from PBMCs by 97.2-100%. Compared with the non-depleted cells, the data obtained from mixed PBMC-MLR assay with T cell depletion indicated that $CD4^+$ T cells, but not $CD8^+$ T cells were the major subset responsible for the induction of IFNγ by 42Y073-86F08-66 (HEK) in this assay (FIG. 13).

Figure 14:
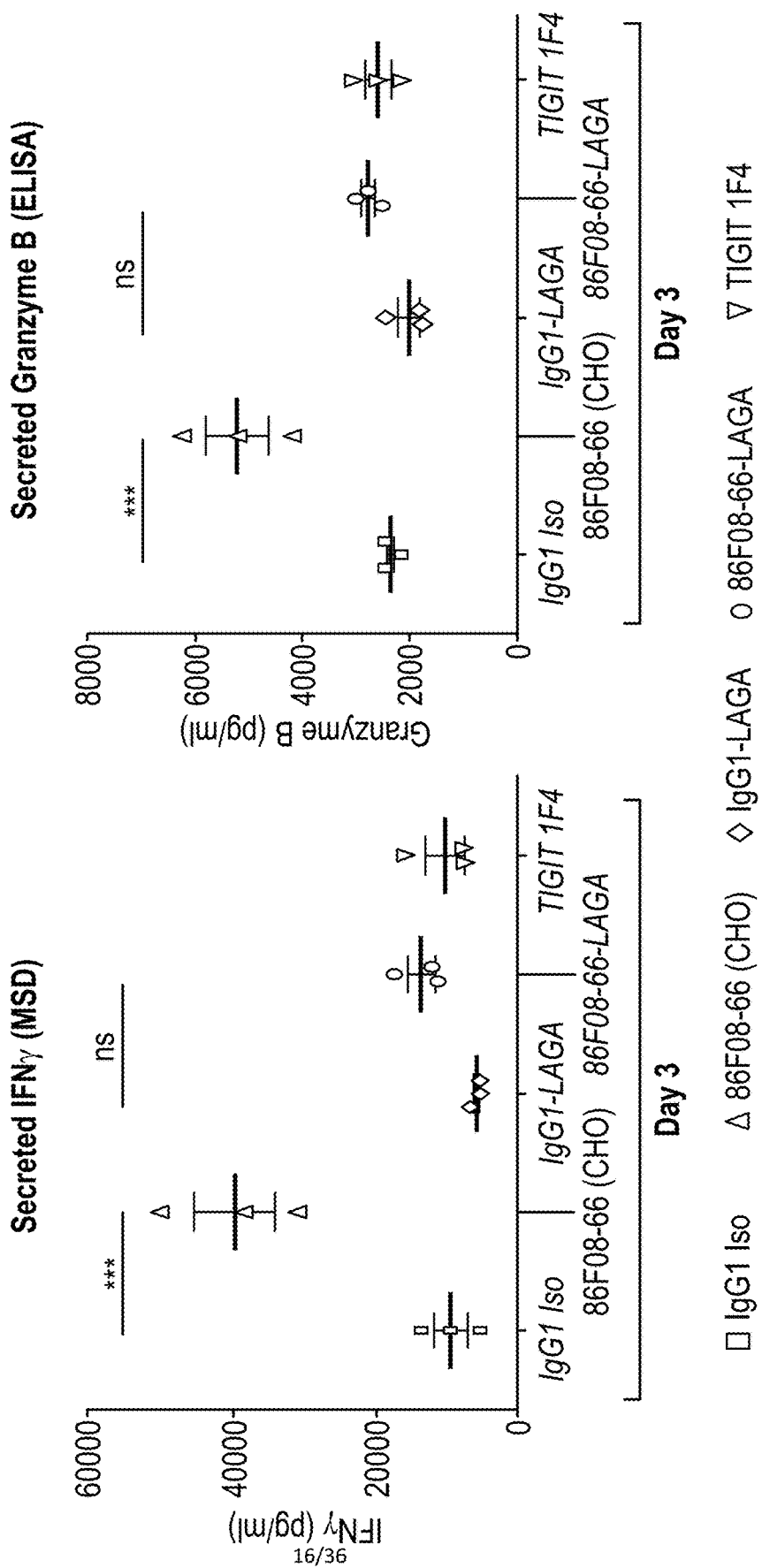
FIG. 14 shows the effect of CD96 binding protein on the secretion of IFNγ and Granzyme B in a mixed PBMC-MLR assay.

Flow Cytometry Study to Understand the Mechanism of Action of CD96 Binding Proteins To further understand the mechanism of action for anti-CD96, flow cytometry studies were carried out to study expression changes of cell surface receptors as well as the intracellular cytokines in different cell populations in human PBMCs. The same mixed PBMC-MLR assay system was used. PBMCs from 8 donors were mixed together for cell activation via MHC-mismatch. After anti-CD96 or isotype control antibodies were added, the PBMCs were incubated for 0 day (baseline) or 3 days, and cells were subsequently fixed and various markers were quantified by flow cytometry. To confirm the activity of 42Y073-86F08-66 in this experiment, secreted IFNγ and Granzyme B in the supernatant were also measured by MSD and ELISA after day 3. As observed before, 42Y073-86F08-66 enhanced IFNγ and Granzyme B release (FIG. 14). No increase of secreted IFNγ or Granzyme B was observed with an anti-TIGIT mAb clone 1F4 (Roche, hIgG1-WT).

To understand what cell populations contributed to the increased IFNγ by 42Y073-86F08-66, intracellular staining of IFNγ was measured in different cell populations by flow cytometry. Even in the IgG1 isotype control treated group, there was a significant increase in the expression (data not shown) as well as the frequency of $IFNγ^+$ $CD4^+$, $CD8^+$ and NK cell subsets at day 3 compared to day 0, indicating lymphocyte activation by mixing the PBMCs from different donors (FIG. 15). Treatment with 42Y073-86F08-66 further significantly increased the frequency of $IFNγ^+$ cells in all three immune subsets, namely, $CD4^+$, $CD8^+$ and NK cells (FIG. 15). Anti-TIGIT antibody (clone 1F4) only increased the frequency of $IFNγ^+$ cells among NK cell population.

Figure 17B:
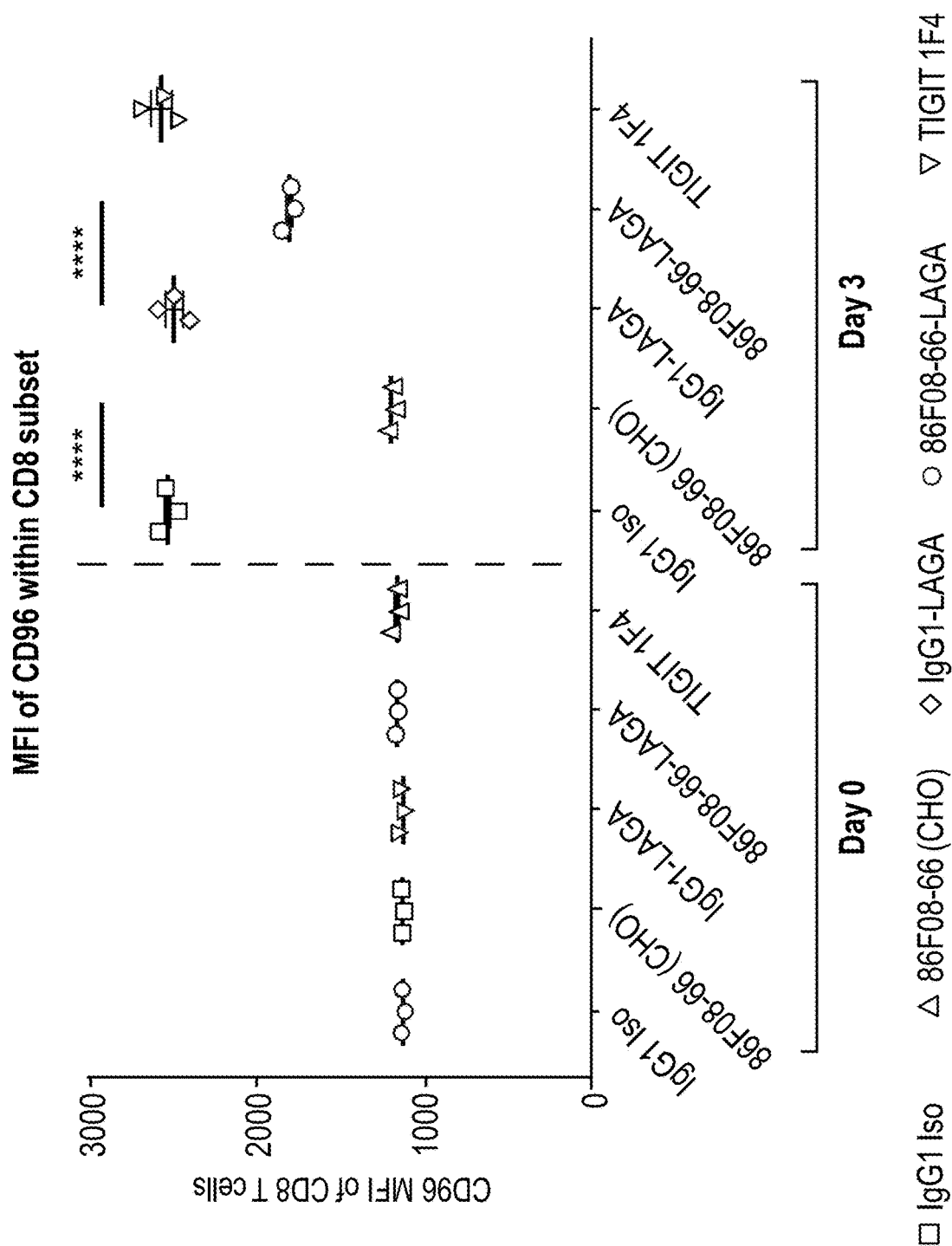

Additionally, CD96 expression was significantly increased in all three cell populations upon cell activation on day 3 comparing to day 0, a profile commonly observed for checkpoint proteins. Anti-CD96 antibody treatment significantly reduced the CD96 MFI and $CD96^+$ cell frequencies in all 3 subsets, $CD4^+$, $CD8^+$ and NK cells, compared to the matched isotype control group. The Fc-disabled 86F08-66-LAGA antibody treatment also led to a reduction in CD96 profile, although the decrease in CD96 expression in the 42Y073-86F08-66 treated group was much more significant (FIGS. 16-17). Anti-TIGIT ab clone 1F4 showed no effect.

This appeared reduction of CD96 expression upon 42Y073-86F08-66 treatment could be due to competition between the anti-CD96 detection antibody and the therapeutic Ab which indicates receptor occupancy by the therapeutic antibody, or it could be due to internalization of CD96 receptor upon binding of 42Y073-86F08-66. The detection antibody used in the analysis is a commercial Ab clone 6F9 (BD Biosciences).

Figure 18:
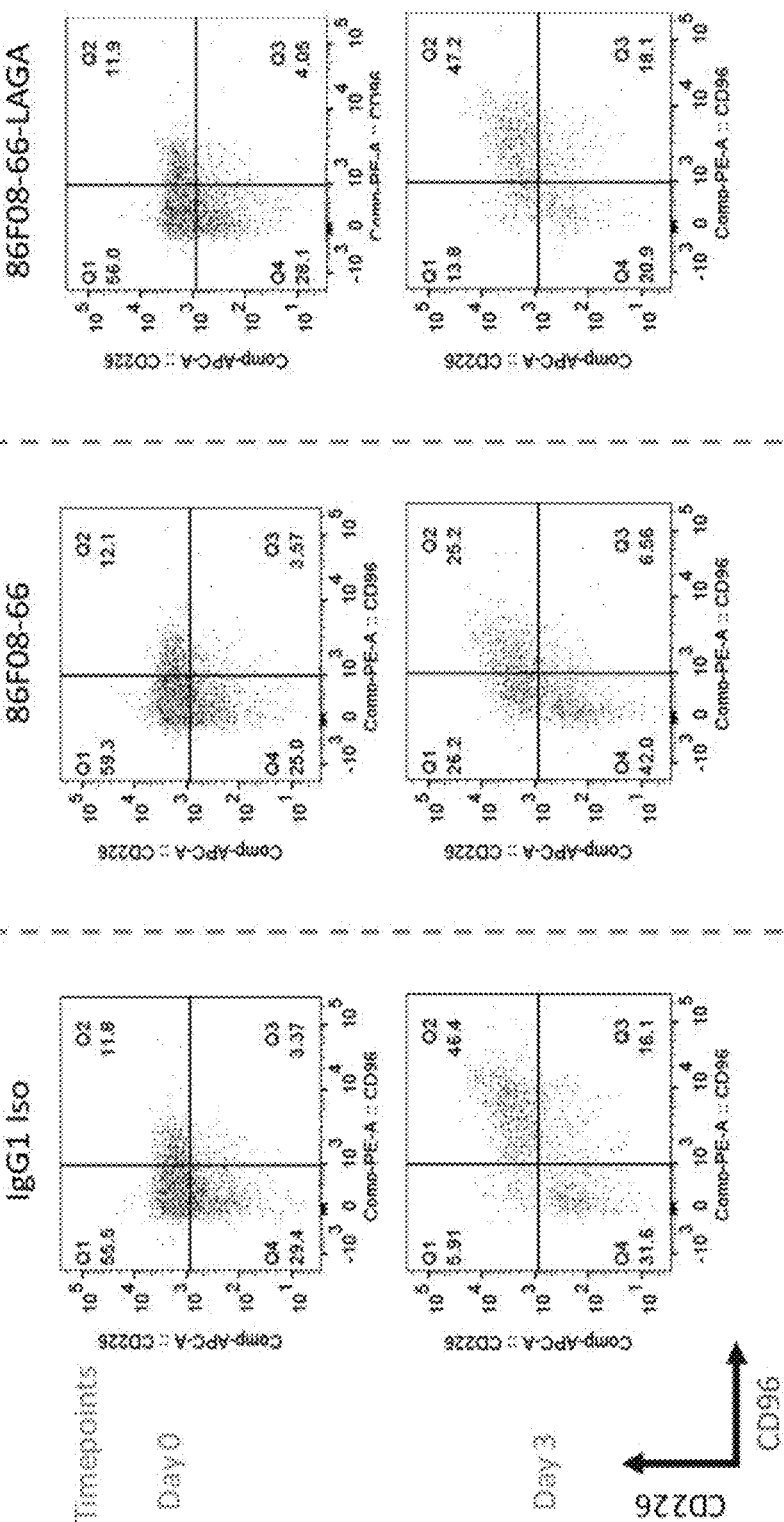
FIG. 18 shows FACs characterization displaying the effect of CD96 binding protein on the ratio of $CD226^+$ single positive vs $CD226^+$ $CD96^+$ double positive NK cells in a mixed PBMC-MLR assay.

CD226 is one of the major activating receptors in NK cells, however, its role in T cells is not as well established. To understand the mechanism of in more detail, we focused on characterizing the CD226$^+$ population of NK cells in the PBMC-MLR assay. Upregulation of CD96 expression upon cell activation on day 3 increased the frequency of CD226$^+$ CD96$^+$ NK cells. Treatment with 42Y073-86F08-66 resulted in higher ratio of CD226$^+$ single positive vs CD226$^+$ CD96$^+$ double positive NK cells on day 3 (26.2%/25.2%=1) compared to both the isotype control (5.91%/46.4%=0.127), as well as the 86F08-66 IgG1 LAGA Fc-disabled antibody (13.8%/47.2%=0.29), potentially through target occupancy and/or internalization of CD96 (FIG. 18). As CD226 is the activating receptor in the axis and CD96 is a putative checkpoint receptor in the same axis, the CD226$^+$ single positive cells may represent more activated NK cells than the CD226$^+$ CD96$^+$ double positive cells.

42Y073-86F08-66 treatment resulted in a higher frequency of IFNγ$^+$ cells and GrzB$^+$ cells among CD226$^+$ NK cells on day 3 after 42Y073-86F08-66 treatment. No effect was observed with the Fc-disabled IgG1-LAGA lead antibody (86F08-66-LAGA).

Figure 19:
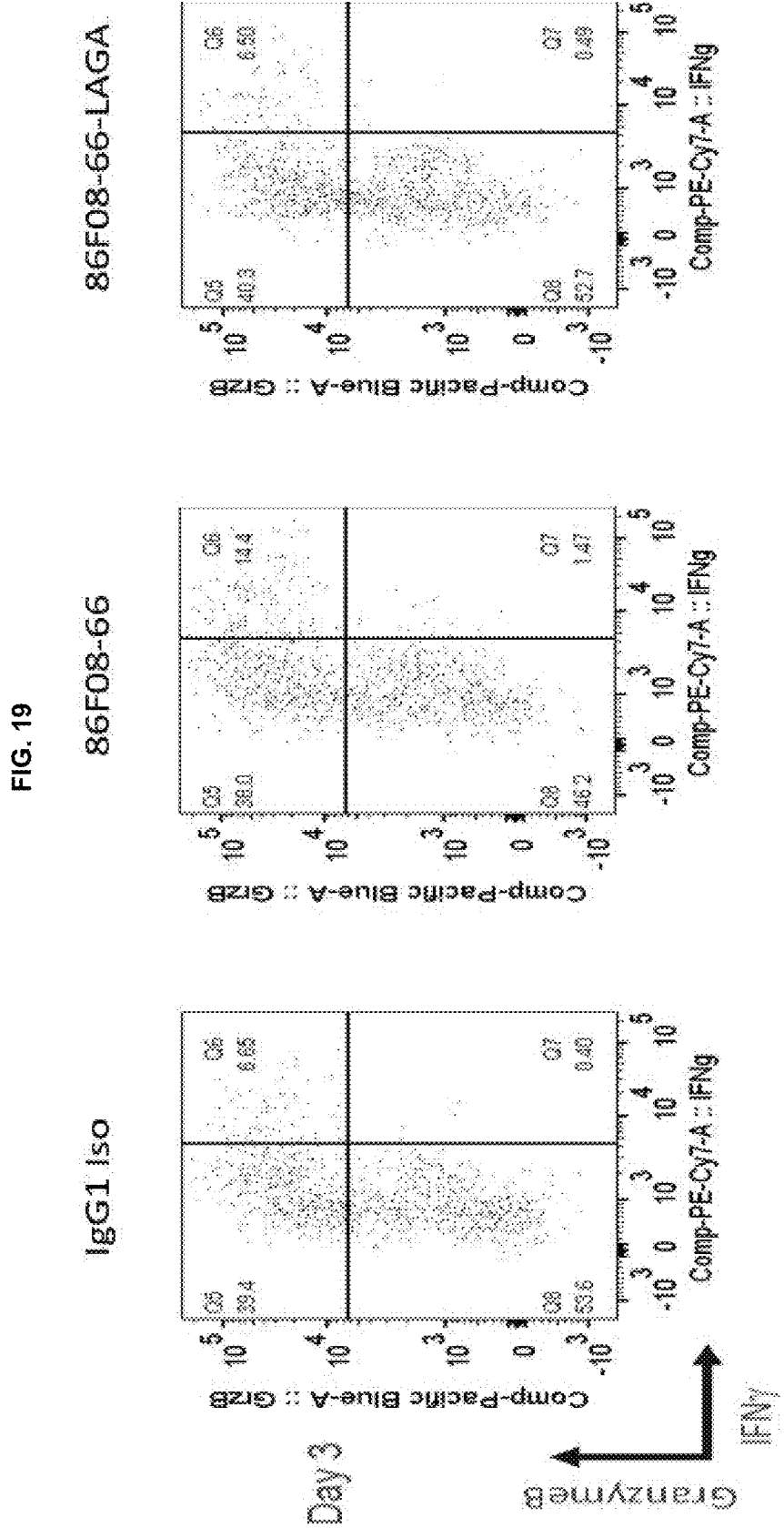
FIG. 19 shows FACs characterization displaying the effect of CD96 binding protein on $IFNγ^+GrzB^+$ double positive cells among NK cell total population in a mixed PBMC-MLR assay.

Overall, 42Y073-86F08-66 treatment resulted in more IFNγ$^+$GrzB$^+$ double positive cells among total NK cells at day 3 comparing to the isotype control Ab or the Fc-disabled IgG1-LAGA lead antibody (86F08-66-LAGA) (FIG. 19).

CD155-PBMC Assay for Screening of CD96 Binding Proteins

Figure 20:
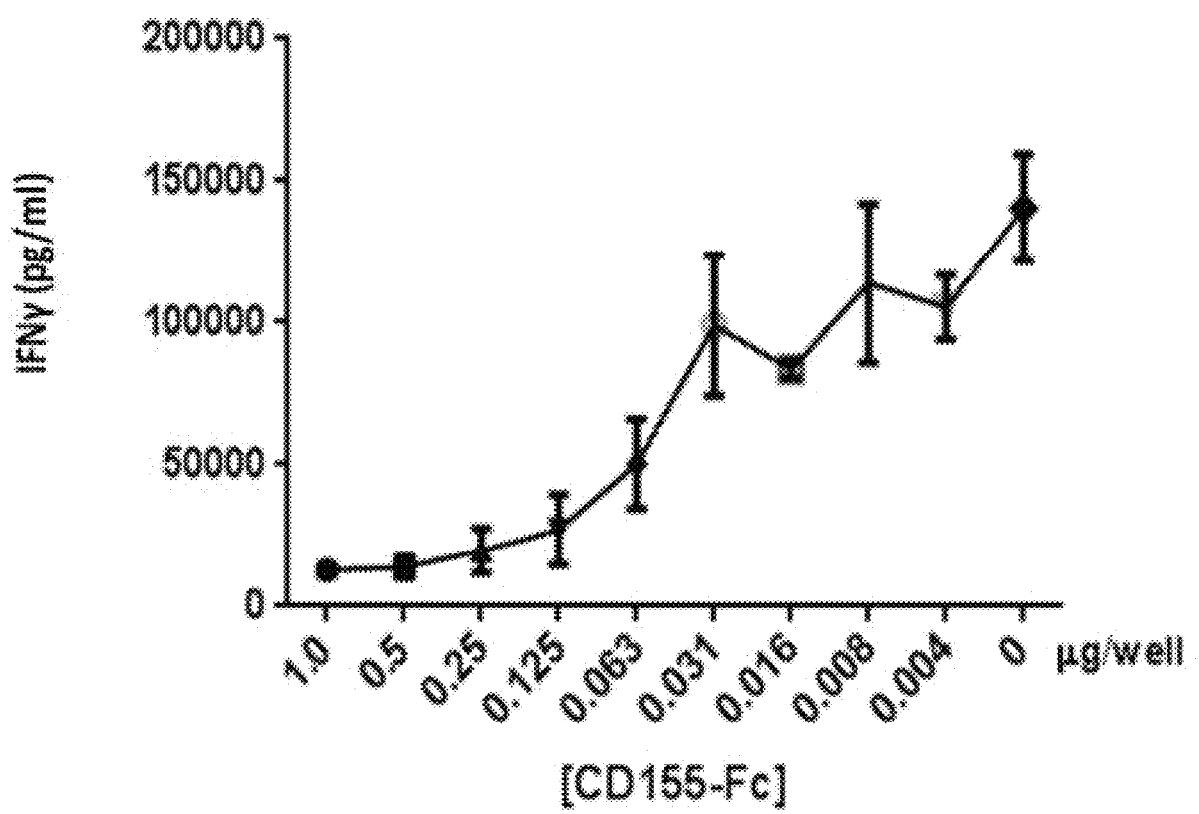
FIG. 20 shows the inhibitory effect of plate-bound CD155-Fc on IFNγ production in a human PBMC assay.
Figure 26:
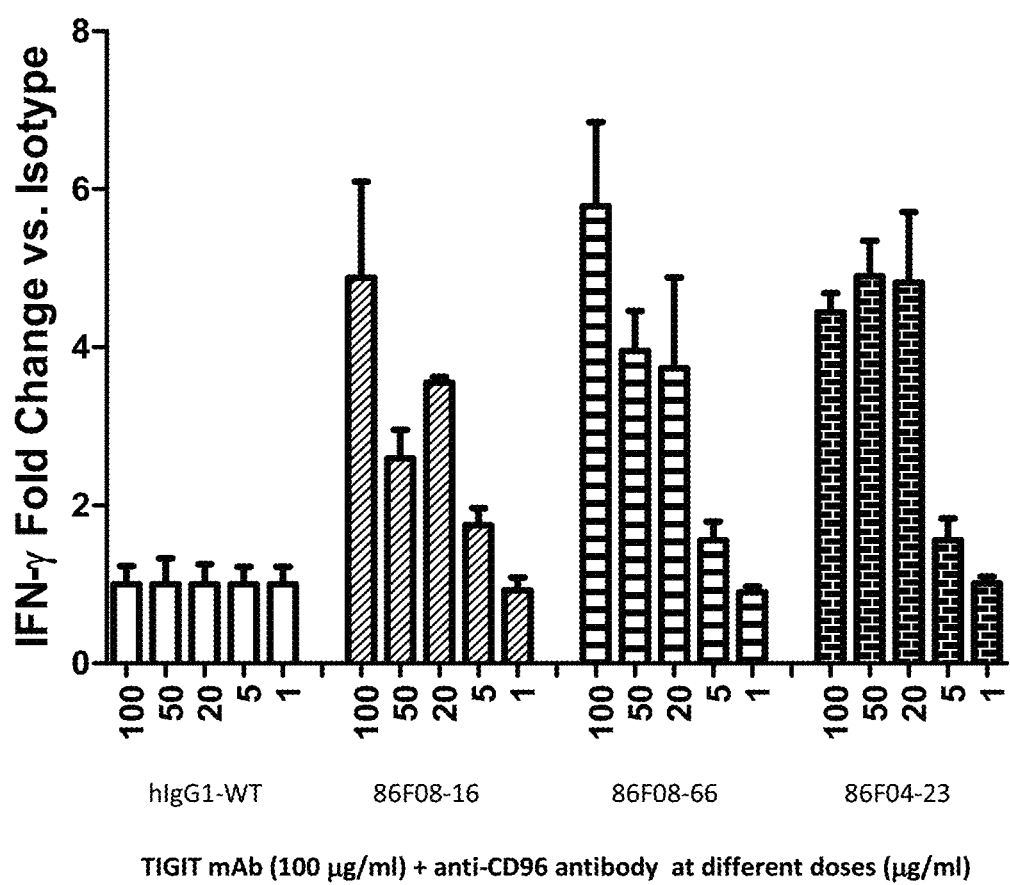
FIG. 26 shows IFNγ production in CD155 coated PBMC assay in the presence of CD96 binding proteins or isotype control in the presence of anti-TIGIT mAb, as evaluate by MSD.
Figure 27:
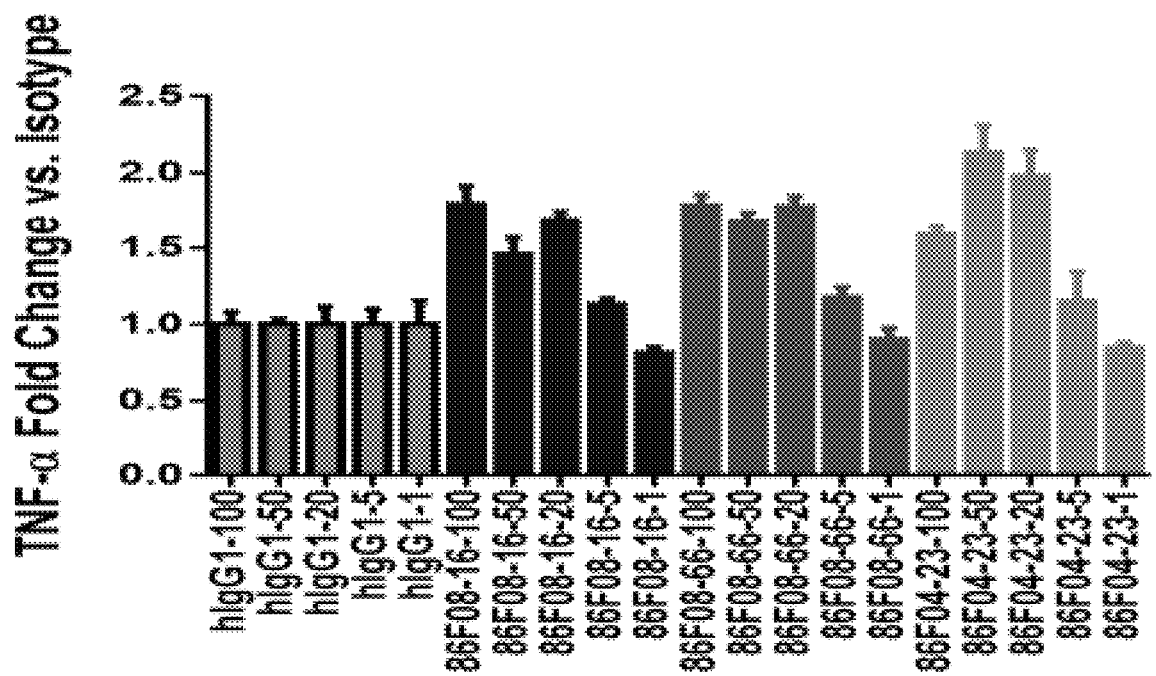
FIG. 27 shows TNFα production in CD155 coated PBMC assay in the presence of CD96 binding proteins or isotype control in the presence of anti-TIGIT mAb, as evaluate by MSD.
Figure 28:
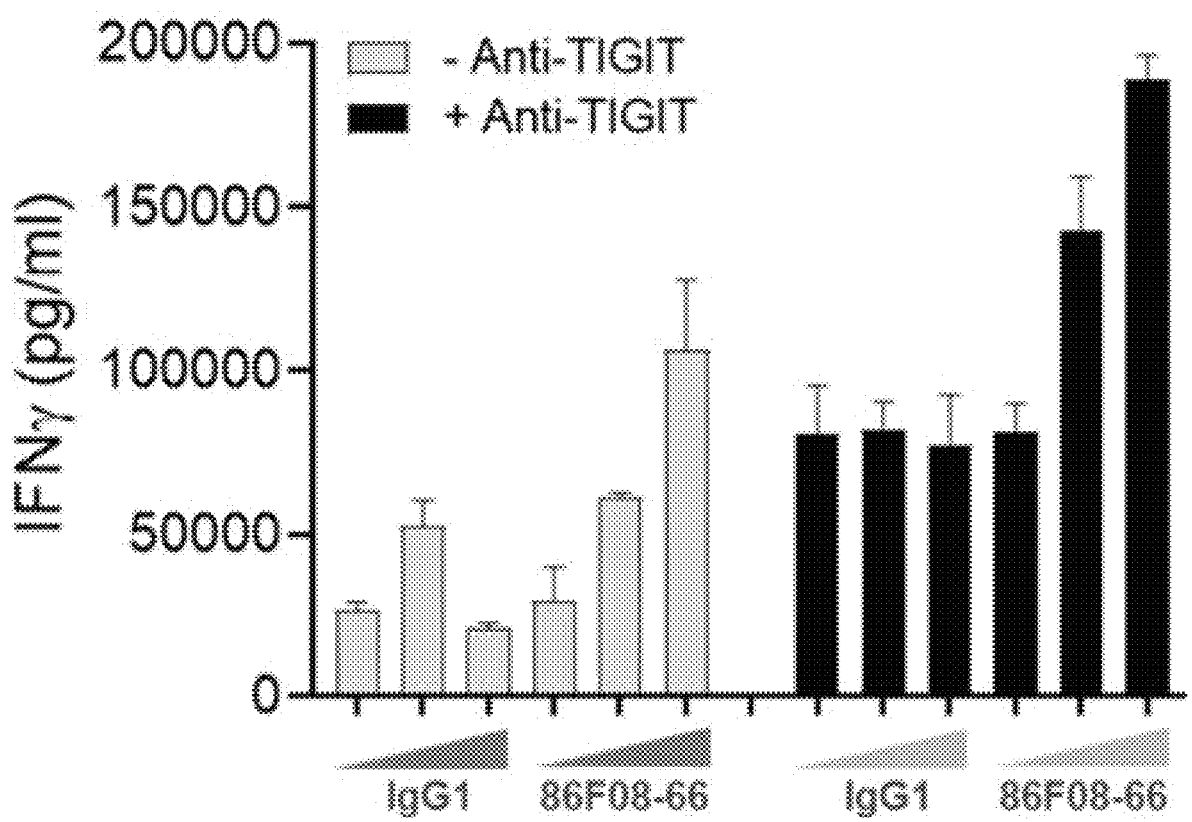
FIG. 28 shows IFNγ production in CD155 coated PBMC assay in the presence of CD96 binding proteins or isotype control in the presence or absence of anti-TIGIT mAb for 3 days, as evaluated by MSD.

To determine the inhibitory effect of plate-bound CD155-Fc on IFNγ production in human PBMCs, round-bottom 96-well non-TC plate (#351177) were coated with rhCD155-Fc (Cat #9174-CD-050, R&D Systems) at different doses overnight at 4° C. and blocked with AIM-V medium (Cat #12055-091, Therrmo Fisher) containing 5% BSA (cat #9576, Sigma) for 30 min at room temperature. PBMCs (Cat #70025, Stemcell Technologies) were pretreated with CD96 binding proteins, anti-TIGIT mAb (Cat #MAB7898, R&D Systems) or isotype control at room temperature for 10 min were added into wells at 2×10$^5$ cells/well in AIM-V medium containing 0.01 μg/ml of anti-CD3 mAb and cultured for 3 days. The supernatants were harvested and stored at −20° C. for measurement of IFNγ and Granzyme B by MSD or ELISA. The inhibitory effect of plate-bound CD155-Fc on IFNγ production in human PMBCs is illustrated in FIG. 20. CD96 binding proteins appear to mitigate CD155-Fc mediated IFNγ inhibition (vs. IgG1-WT isotype control antibody) (FIG. 26). Additional assays were conducted determining the ability of CD96 binding proteins mitigate CD155-Fc mediated TNFα suppression (in the presence of anti-TIGIT mAb) (FIG. 27). Further assays conducted with and without anti-TIGIT mAb indicate that the ability of the CD96 binding proteins to mitigate CD155-Fc inhibition on IFNγ production is apparent both with and without the presence of anti-TIGIT mAb (FIG. 28).

Activity of CD96 Binding Proteins in Human Tumor Infiltrating Lymphocyte (TIL) Assays The tumor microenvironment (TME) is immune-suppressive, and tumor infiltrating lymphocytes (TIL) found in the tumors are often immuno-dysfunctional or 'exhausted'. A primary human TIL assay was developed to evaluate the potential therapeutic effect of 42Y073-86F08-66 in vitro. Fresh, primary resected tumors were mechanically and enzymatically dissociated into single cell suspensions that contain both tumor cells and TILs. The TILs in the cell suspension were mildly activated with a suboptimal dose of soluble anti CD3 (clone HIT3a) and were plated in triplicate into 96 well ultra-low attachment round bottomed spheroid formation plates. The antibodies were then added to the wells, and IFNγ in the supernatant was measured after 6 days. 42Y073-86F08-66 was evaluated in this assay at 3 concentrations (10, 2, and 0.5 μg/mL) alone or in combination with either anti-PD-1 (Keytruda/pembrolizumab) (10 μg/mL) or anti-TIGIT (100 μg/mL). Anti-PD-1 alone was also tested as a positive control for induction of IFNγ above anti-CD3 alone. Appropriate isotype controls were also included.

Figure 21:
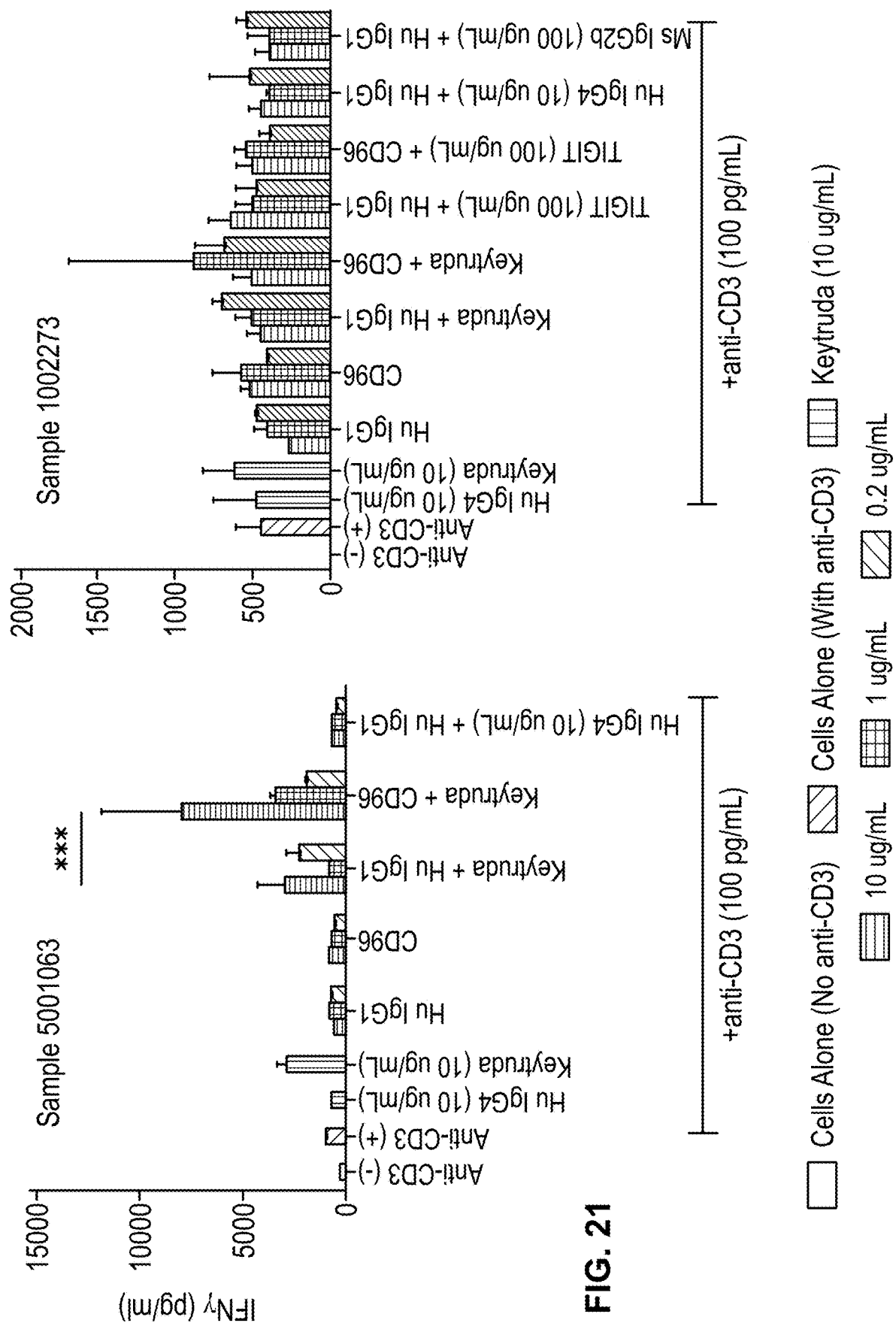
FIG. 21 shows the activity of CD96 binding protein in renal cancer TIL functional assays, alone or in combination with anti-PD1 or anti-TIGIT antibodies.

A total of 6 tumors (4 endometrial and 2 renal) were tested in this assay. For the 4 endometrial tumors, anti-PD-1 together with anti-CD3 treatment induced equivalent IFNγ levels as anti-CD3 alone, indicating that the anti-CD3 stimulation may be too high and further technical development may be necessary. In one of the two renal tumors (Sample 5001063), anti-PD-1 treatment augmented (p<0.05 by 1-way Anova) IFNγ production above anti-CD3 alone. Additionally, anti-PD-1+42Y073-86F08-66 (10 μg/mL) combination treatment significantly (p<0.001 by one-way Anova) enhanced IFNγ levels to 7764 pg/mL, higher than the 10 μg/mL 42Y073-86F08-66 alone (599 pg/ml), anti-PD-1 alone (2692 pg/mL), or a simple additive effect of the two (FIG. 21). For the second renal tumor (Sample 1002273), anti-PD-1 treatment did not enhance IFNγ production above anti-CD3 stimulation alone. These tumors were not prescreened for PD-1 axis expression or CD96-axis expression. The complexity of these TIL assays is broadly recognized and variation in response to anti-PD-1 treatment among patient tumors has been observed. This is not surprising given the overall response rate for anti-PD-1 (Keytruda) in unscreened patients is below 25%.

Example 4

In vivo Efficacy and Mechanism Studies
Bioluminescence Imaging Study of CD96 Binding Protein in a NK Cell Dependent B16F10 Melanoma Lung Colonization Model NK cells are part of the innate lymphocyte family and play a prominent role in controlling early tumor growth and the spread of metastases through cytotoxic activity and the release of inflammatory cytokines. A frequently used in vivo model of studying NK cell-dependent anti-cancer activity is the B16F10 melanoma lung colonization model. This model was also described in the CD96 cancer related publications (Blake S. J., et al. 2016). We decided to use the same model to study 42Y073-86F08-66 (produced in HEK cells) activity in vivo. To measure the efficacy of anti-CD96 mAb in controlling lung metastasis in real time, and in a more quantitative way, instead of using regular B16F10 melanoma cells, B16F10 cells encoding Red Firefly luciferase (RFluc) were used to allow in vivo imaging of the luciferase signal from the lung indicative of tumor burden.

Figure 22A:
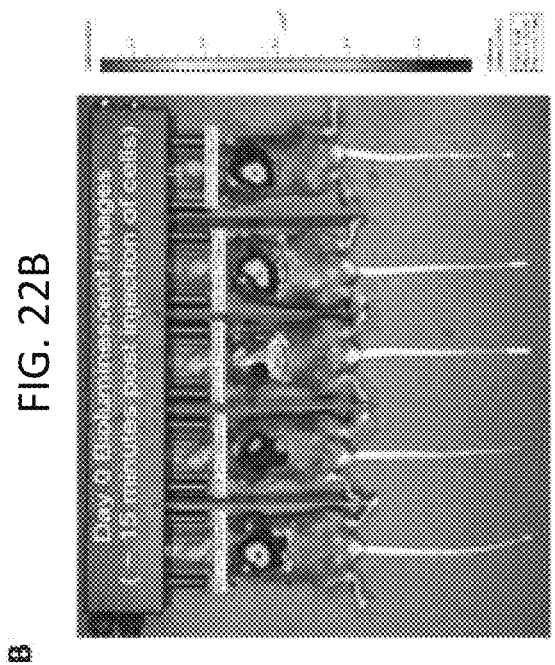
FIGS. 22A and 22B show bioluminescence imaging study data of CD96 binding protein in a NK cell dependent B16F10 melanoma lung colonization model, showing representative bioluminescent images acquired approximately 15 minutes post injection of B16F10 RFluc melanoma cells.
Figure 22B:
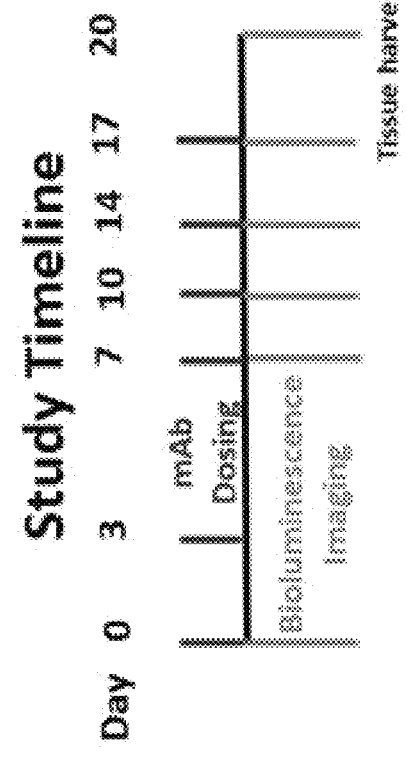

Following the tail vein administration of ~500,000 B16F10 RFluc metastatic melanoma cells, in vivo bioluminescent imaging was performed at Day 0 (~15 minutes post injection of cells), Day 7, 10, 14, 17, and 20. (Initial cell colonization occurs in the lungs as early as 15 minutes post injection from previous model development studies). Dosing frequency was twice per week (FIG. 22). Following in vivo imaging at Day 20, mice were harvested for ex vivo bioluminescent imaging of the mouse lungs.

To further evaluate the role of specific immune cell types (CD4$^+$, CD8$^+$, and NK Cells) in this system, CD4$^+$ cells, CD8$^+$ cells, NK cells or both CD4$^+$ and CD8$^+$ cells were depleted using an established antibody treatment method. Subsequent flow cytometry analysis confirmed the depletion of NK cells as well as T cells in the CD4$^+$/CD8$^+$ depletion group.

Figure 23:
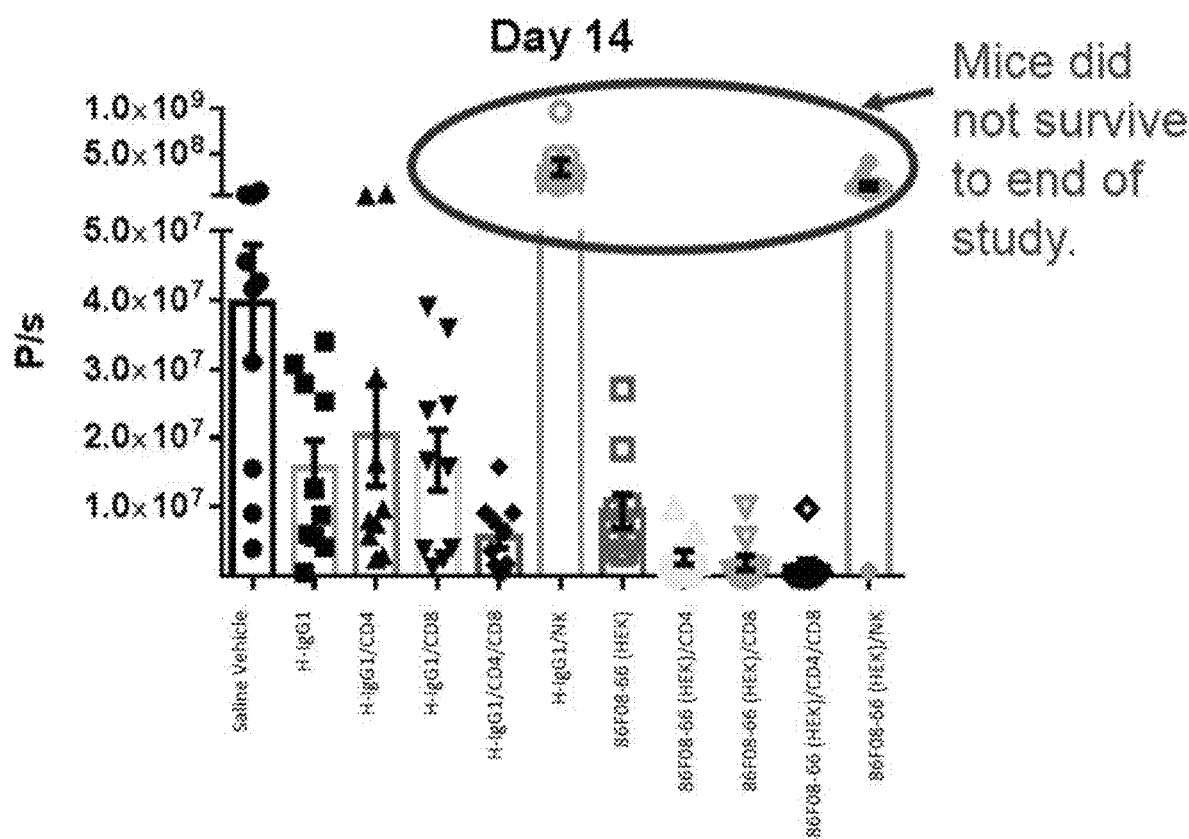
FIG. 23 shows lung bioluminescent signal at Day 14 post B16F10 cell injection in mice without depletion; with CD4, CD8, or NK cell depletion.

Bioluminescent imaging at Day 14 revealed significantly increased signal in the lungs of NK cell depleted groups (FIG. 23). When there is lower lung signal (p/s) there is less metastases. In fact, 19 out of 20 mice did not survive to the end of the study presumably due to heavy lung tumor burden. This data clearly supports the critical role of NK cells as primarily responsible for suppressing lung metastasis in this model.

Figure 24A:
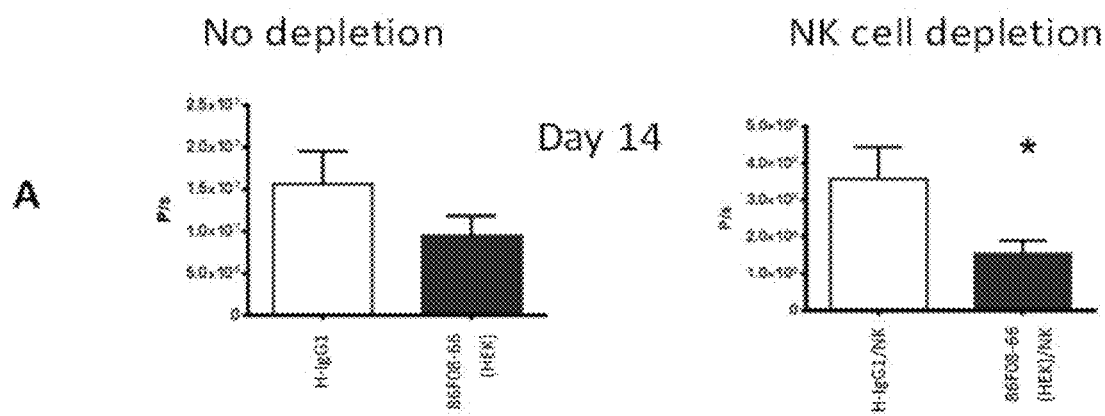
FIGS. 24A and 24B show in vivo bioluminescent lung signals at day 14 and day 20 exhibiting the effect of CD96 binding proteins (vs control) on lung metastasis in various groups.
Figure 24B:
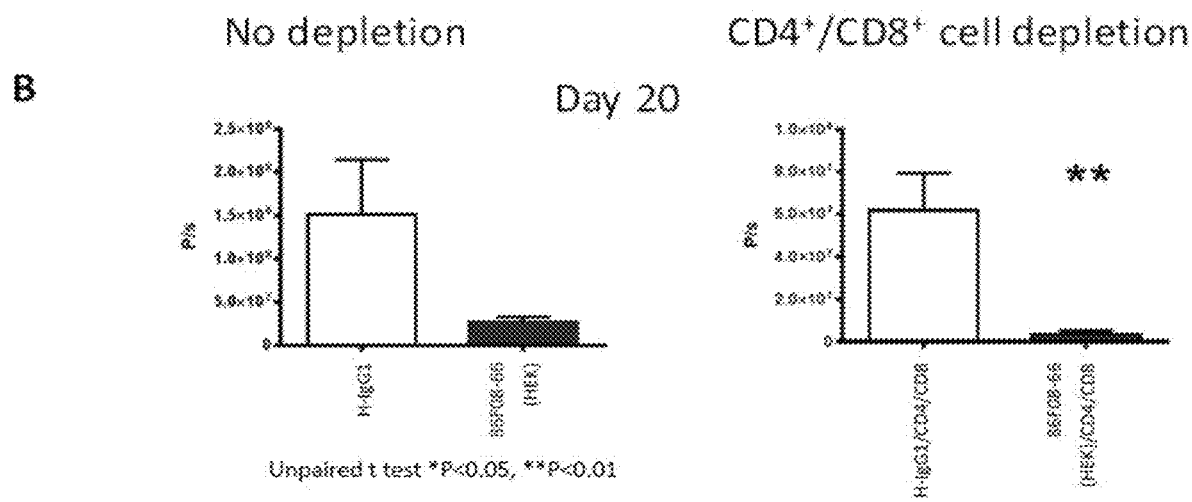

In vivo bioluminescent imaging performed at Day 14 when the NK depleted mice were still alive showed that for NK depleted groups, 42Y073-86F08-66 (produced in HEK cells) treatment significantly reduced lung metastasis (* $P<0.05$) comparing to isotype control treatment (FIG. 24, A). For the undepleted group, the trend was also observed but not statistically significant. At Day 20, for the undepleted groups, lung signal was decreased in 42Y073-86F08-66 treated group but was not statistically significant (ns). For the T cell depleted groups, 42Y073-86F08-66 significantly reduced (** $P<0.01$) lung signal compared to isotype control (FIG. 24, B). When there is lower lung signal (p/s) there is less metastases. The digital picture of the lungs after mice were sacrificed on day 20 confirmed the effect of 42Y073-86F08-66 (FIG. 25).

Example 5

Efficacy Data and Mechanism Summary
Evidence of Activity of 42Y073-86F08-66 on T Cells
Human: CD96 is expressed at readily detectable level on both CD4 and CD8 T cells in PBMCs, as well as in tumor microenvironment. In TILs, besides NK cells, CD96 was found on CD8, CD4 Teff cells as well as Tregs. Consistent with its expression pattern, flow cytometry analysis showed that 42Y073-86F08-66 treatment increased the percentage of IFNγ$^+$ CD4$^+$ and CD8$^+$ T cells in the mixed PBMC-MLR assay. Depletion studies showed a dramatic loss of IFNγ release by 42Y073-86F08-66 in the mixed PBMC-MLR assay when CD4 T cells were depleted. However, CD8 depletion was not very impactful in this particular assay.

Mouse: In the in vivo setting, for the B16F10 lung colorization assay, on day 14 after tumor cell injection when NK depleted mice were still alive, when NK cells were depleted, 42Y073-86F08-66 treatment still showed a statistically significant reduction of lung metastasis comparing to isotype control, presumably through activating T cells.
Evidence of NK Cell Activity
Human: CD96 is expressed at readily detectable level on NK cells in PBMCs, as well as in the tumor microenvironment. In fact, among TIL subpopulations, the highest level of CD96 expression was found on NK cells. CD226 is one of the major activating receptors for NK cells, and strong NK activity target validation data for CD96 was also reported in the literature. In the in vitro setting, intracellular cytokine staining studies using flow cytometry showed increased IFNγ$^+$GrzB$^+$ NK cells upon 42Y073-86F08-66 treatment in the mixed PBMC-MLR assays.

Mouse: In the in vivo setting, using a well-recognized highly NK cell dependent model, the B16F10 lung colonization model, 42Y073-86F08-66 was able to significantly suppress lung metastasis when both CD4 and CD8 T cells were depleted, strongly suggesting through NK activity.

Example 6

Anti-CD96 mAb—Nonclinical Toxicology Studies

GSK6097608B (hereafter referred to as GSK6097608 and which is the same as 42Y073-86F08-66) is a monoclonal antibody (mAb) targeting cluster of differentiation (CD)96 that is being developed for the treatment of cancer. Intravenous (IV) dose-range and 4-week repeat-dose toxicity studies with an anti-CD96 mAb have been conducted in cynomolgus monkeys and BALB/c mice. Additionally, a single-dose PK and PD study was conducted in monkeys. An in vitro CRA in human blood samples and a combination CRA with dostarlimab (anti-PD-1 mAb) have been conducted. An assessment of the binding profile was conducted using a human microarray with follow-up confirmatory binding assays. A preliminary immunohistochemistry (IHC) study was performed using selected human and cynomolgus monkey tissues.

BALB/c mouse and cynomolgus monkey were selected as nonclinical species in which to assess the safety profile of the anti-CD96 mAb. The monkey was considered to be an appropriate nonclinical species in which to assess the potential toxicities of the anti-CD96 mAb because the anti-CD96 mAb cross-reacts with similar affinity to human and monkey CD96 receptors. Additional nonclinical safety studies were performed in BALB/c mice based on initial PK and efficacy study results, as well as in vitro binding of the anti-CD96 mAb to murine splenocytes and cytokine production by murine splenocytes prestimulated with CD3/CD28 and incubated with the anti-CD96 mAb.

The anti-CD96 mAb was well tolerated in monkey toxicology studies following 4 weekly doses up to 100 mg/kg/week. CD96 receptor occupancy (RO) or target engagement on CD8+ T cells, CD4+ T cells, and NK cells was maintained throughout all studies. A low incidence of low titer anti-drug antibodies (ADA) was observed that did not affect receptor binding or systemic exposure. There were no changes in the number of circulating cells expressing CD96 and no histopathology findings in tissues, including primary and secondary immune tissues, suggesting the risk of fragment crystallizable (Fc)-dependent depletion of CD96-expressing effector cells is low. the anti-CD96 mAb was tolerated for 4 weeks at 100 mg/kg/week in mice; however, a lower dose of 10 mg/kg/week caused immune-mediated anaphylaxis due to ADA or circulating immune complexes following the third weekly dose administration.

An in vitro CRA evaluating the anti-CD96 mAb alone, dostarlimab alone, and the combination of the anti-CD96 mAb with dostarlimab was conducted using PBMCs isolated from 5 male and 5 female healthy donors. Compared with media controls, there were minimal increases in interleukin (IL)-10, an immunoregulatory anti-inflammatory cytokine, in most donors with each antibody treatment and mild to moderate treatment-related increases in IL-6 and/or tumor necrosis factor alpha (TNF-α) for 1 donor in each of the anti-CD96 mAb-alone and dostarlimab-alone conditions. These levels were less than the anti-CD3 and anti-CD28 positive controls that induced a pan-cytokine response. Overall, there was no augmentation of cytokine response with the combined treatment; however, the 1 donor with increased IL-6 and TNF-α in the anti-CD96 mAb-alone condition was also more sensitive to the combined treatment. The results indicate an overall low risk for cytokine release syndrome (CRS), but there may be individual participant responses for induction of cytokines.

Based on the tolerability and absence of relevant adverse findings, the no observed adverse effect level (NOAEL) was determined to be 100 mg/kg/week (the highest dose tested) in both monkeys (gender-averaged Week 4 mean area under the curve [AUC]0-168h: 580 mg·h/mL [range: 483 to 647 mg·h/mL] and Cmax: 5.54 mg/mL [range: 5.10 to 6.54 mg/mL]) and mice (gender-averaged Week 4 mean AUC0-168h: 319 mg·h/mL and Cmax: 2.98 mg/mL).

Example 7

First Time in Human Study of Ant-CD96 mAb as a Monotherapy and in Combination with Dostarlimab (Also Known as TSR-042)

GSK6097608B (hereafter referred to as GSK6097608 and which is the same as 42Y073-86F08-66) is a monoclonal antibody (mAb) targeting cluster of differentiation (CD)96 (anti-CD96 mAb) that is being developed for the treatment of cancer. Engagement of CD96 by a related receptor, CD155, functions as an 'off switch,' or immune checkpoint, to downregulate immune responses. This CD96 antagonist antibody was developed to block the CD96:CD155 inhibitory axis and increase T cell and natural killer (NK) cell antitumor activity. This first-time-in-human (FTIH) study will evaluate the safety, tolerability, pharmacokinetics (PK), pharmacodynamics (PD), and preliminary clinical activity of GSK6097608 given as monotherapy and in combination with dostarlimab. Dostarlimab (also known as TSR-042) is an investigational humanized mAb of the immunoglobulin (Ig) G4 (IgG4) isotype; it has a high affinity for binding to programmed cell death protein 1 (PD-1), resulting in inhibition of binding to programmed death ligand (PD-L)1 and PD-L2. Based on the observed antitumor activity of other antibodies in the same class, dostarlimab is expected to exhibit clinical activity in a broad spectrum of cancers.

Based on evidence supporting the molecular interplay between pathways and the utility of addressing diverse immune populations, GSK6097608 may not only work in concert with PD-(L)1 (programmed cell death protein 1 and/or programmed death ligand 1) inhibition, but also benefit patients who are refractory to, or have developed resistance to, current T cell-based therapeutics.

Scientific Rationale for Combination with Anti-PD-1

Despite the therapeutic benefit of blocking the immune-checkpoint pathways PD-(L)1 and CTLA-4 across multiple tumor types, most patients do not respond to monotherapy with checkpoint inhibitors, and strategies to increase their activity by combination approaches are being actively explored. The rationale for combining an anti-CD96 mAb (GSK6097608) with an agent designed to block the PD-(L)1 pathway (dostarlimab, anti-PD-1 mAb) is based on evidence supporting the molecular interplay between pathways, the utility of addressing diverse immune populations, and therapeutic complementarity between intervention strategies.

On a mechanistic level, PD-1 signaling has been shown to dephosphorylate the intracellular domain of CD226, attenuating the potential for co-stimulation following CD96-mediated CD155 redirection. Notably, the expression of CD96 is upregulated in melanoma tumor tissue following nivolumab (anti-PD-1) treatment, implicating the CD96 inhibitory axis as a possible adaptive resistance mechanism to PD-1 blockade. Reciprocal upregulation of pathway components may also be observed with CD96 blockade, as GSK6097608-mediated induction of interferon gamma (IFNγ) has the potential to upregulate PD-L1 expression. Collectively, these observations suggest that co-blockade of CD96 and PD-(L)1 may be necessary to enable effective antitumor immune responses.

Clinical Experience with Dostarlimab

Dostarlimab is currently being developed as a monotherapy for patients with recurrent or advanced solid tumors, including endometrial cancer (microsatellite stable and microsatellite instability-high [MSI-H] tumors), non-small-cell lung cancer (NSCLC), and nonendometrial MSI-H solid tumors and polymerase ε-mutated cancer. In addition, dostarlimab is being developed as a combination therapy with other therapeutic agents for patients with advanced solid tumors (including melanoma, NSCLC, and colorectal cancer) or advanced or metastatic cancer (including endothelial ovarian cancer, triple-negative breast cancer, and urothelial carcinoma).

As of 21 Jan. 2019, there were 4 ongoing Phase 1 studies, 2 ongoing Phase 2 studies, and 1 ongoing Phase 3 study with dostarlimab.

The safety and tolerability of dostarlimab have been evaluated in over 627 participants with advanced cancer who have received at least 1 dose of dostarlimab. Of the 335 participants treated with dostarlimab monotherapy in the FTIH Study 4010-01-001 (GARNET), 93.7% reported at least 1 treatment-emergent adverse event (TEAE), with events of fatigue, nausea, and diarrhea being the most frequently reported. Study intervention-related TEAEs-≥Grade 3 were reported in 36 participants (10.7%). The majority of study intervention-related TEAEs≥Grade 3 occurred in only 2 participants each, with the exception of fatigue (6 participants), alanine aminotransferase (ALT) increased (4 participants), anemia (4 participants), aspartate aminotransferase (AST) increased (3 participants), and lipase increased (3 participants). Serious adverse events (SAEs) occurred in 106 participants (31.6%); in 21 of these participants, these SAEs were considered study-intervention related. All study intervention-related SAEs occurred in 1 participant each, with the exception of pneumonitis (4 participants), dyspnea (2 participants), pyrexia (2 participants), and rash maculopapular (2 participants). Twenty-three participants (6.9%) who received dostarlimab monotherapy experienced at least 1 immune-related adverse event (irAE) with severity of ≥Grade 3; for 18 of 23 participants with ≥Grade 3 irAEs, the adverse event (AE) was assessed as study-intervention related by investigators. The majority of ≥Grade 3 irAEs were reported in ≤participants each. The irAEs≥Grade 3 reported in >2 participants were AST increased (4 participants), ALT increased (4 participants), lipase increased (4 participants), and rash (3 participants).

Of the 292 participants treated with dostarlimab in combination with other therapeutic agents, 94.5% reported at least 1 TEAE, with events of fatigue, nausea, and dyspnea being the most frequently reported. SAEs occurred in 108 participants (37.0%); in 20 of these 108 participants, the SAEs were related to the study intervention.

Based on the safety data from human experience and the available nonclinical pharmacology and toxicology information, dostarlimab has demonstrated an acceptable clinical and nonclinical safety profile that appears to be consistent with the safety experience of approved mAb PD-1 inhibitors, pembrolizumab and nivolumab.

Based on the observed antitumor activity of other antibodies in the same class, dostarlimab is expected to exhibit clinical activity in a broad spectrum of cancers. Preliminary efficacy data from 15 participants with MSI-H endometrial cancer and 24 participants with NSCLC who had at least 1 tumor assessment were presented at the April 2018 annual meeting of the American Association for Cancer Research. Responses were assessed by investigators using immune-related Response Evaluation Criteria in Solid Tumors (irRECIST). Among the 15 participants with MSI-H endometrial cancer, the overall response rate was 47% and consisted of all partial responses (PRs); 20% had stable disease (SD) and 33% had disease progression. Among the 24 participants with NSCLC, the ORR was 29% and consisted of all PRs; 42% had SD, and 17% had disease progression. Thus, preliminary efficacy data from participants with NSCLC treated with dostarlimab appear to be comparable to the reported efficacy of other PD-(L)1 inhibitors, such as pembrolizumab, in participants with advanced and recurrent cancer (ORR: 19%) [Herbst, 2016].

Objectives and Endpoints

This FTIH, open-label, dose-escalation study will assess the safety, tolerability, PK, PD, and preliminary clinical activity of GSK6097608 in participants with locally advanced, recurrent, or metastatic solid tumors as monotherapy (Arm A) or in combination with dostarlimab (Arm B); the study will be used to define the recommended Phase 2 dose (RP2D).

TABLE 10

Study summary:

| Objectives | Endpoints |
|---|---|
| Primary | |
| To determine the safety, tolerability, and the RP2D of GSK6097608 administered IV as monotherapy (Arm A) or in combination with dostarlimab (Arm B) to participants with advanced or recurrent solid tumors | Incidence of DLTs<br>Incidence, duration, and severity of AEs and SAEs |
| Secondary | |
| To further characterize the safety and tolerability of GSK6097608 administered IV as monotherapy (Arm A) or in combination with dostarlimab (Arm B) to participants with advanced or recurrent solid tumors | Changes in safety assessments (eg, laboratory parameters, vital signs, cardiac parameters)<br>Dose modifications (eg, dose reductions or delays)<br>Withdrawals due to AEs |
| To evaluate the antitumor activity of GSK6097608 as monotherapy (Arm A) or in combination with dostarlimab (Arm B) in participants with advanced or recurrent solid tumors | ORR based on RECIST 1.1 criteria |
| To evaluate immunogenicity to GSK6097608 as monotherapy (Arm A) and in combination with dostarlimab (Arm B) | Incidence and titers of ADA to GSK6097608 (Arm A and Arm B) and dostarlimab (Arm B) |
| To characterize the PK properties of GSK6097608 as monotherapy (Arm A) and in combination with dostarlimab (Arm B) | GSK6097608 (Arms A and B): plasma concentrations, PK parameters such as Cmax, Cmin, AUC, t½, as data permit<br>Dostarlimab (Arm B): plasma concentrations, PK parameters such as Cmax, Cmin, AUC, t½, as data permit |
| Exploratory | |
| To further evaluate the clinical activity of GSK6097608 | ORR based on iRECIST criteria<br>DCR, TTR, DoR, and TTP based on RECIST 1.1 and iRECIST, as data permit |
| To evaluate the PD effect of GSK6097608 in blood and tumor when administered as monotherapy (Arm A) or in combination with dostarlimab (Arm B) | PD assessment of blood and tumor biomarkers, which may include the CD96 axis, immune cell phenotypes, gene expression (RNA), genomic DNA, T-cell or B-cell receptor sequences, cell-free tumor nucleic acid, and various measures of immune function |
| To evaluate the exposure-response relationships for GSK6097608 for PD, clinical activity, and safety | Relationships between parameters of PK, clinical activity, safety endpoints, and PD markers, which may include<br>PK (plasma concentrations, PK parameters such as Cmax, Cmin, AUC, t½, as data permit)<br>PD biomarkers (eg, immune cell phenotypes, measures of immune function)<br>ORR based on RECIST 1.1 criteria<br>Safety (eg, laboratory parameters, AEs, and SAEs) |

TABLE 10-continued

Study summary:

| Objectives | Endpoints |
| --- | --- |
| To explore the association between GSK6097608 antitumor activity and biomarkers in tumor and blood as monotherapy (Arm A) and in combination with dostarlimab (Arm B) | Correlation between antitumor activity and baseline biomarkers, which may include the CD96 axis and other immune phenotyping markers by IHC or transcription (RNA) in tumor, soluble serum biomarkers, and germline or tumor DNA characteristics |
| Pharmacogenetics: To investigate the relationship between genetic variations in the germline DNA and response to therapy | Germline genetic evaluations may be conducted for: Response, including GSK6097608 alone or in combination with any concomitant medicines Disease susceptibility, severity, progression, and related conditions |
| To explore the gut microbiome composition and relationship to treatment response | Sequencing of the microbiome from stool samples. Analysis of the data to identify potential selection biomarkers for participant enrichment Correlation between antibiotic/probiotic use prior to treatment and antitumor activity |

Abbreviations: ADA = anti-drug antibodies; AE = adverse event; AUC = area under the curve; Cmax = maximum concentration; Cmin = minimum concentration; DCR = disease control rate; DLT = dose-limiting toxicity; DNA = deoxyribonucleic acid; DoR = duration of response; IHC = immunohistochemistry; iRECIST = modified Response Evaluation Criteria in Solid Tumors, version 1.1 for immune-based therapeutics; IV = intravenous(ly); ORR = overall response rate; PD = pharmacodynamic(s); PK = pharmacokinetic(s); RNA = ribonucleic acid; RECIST 1.1 = Response Evaluation Criteria in Solid Tumors, version 1.1; RP2D = recommended Phase 2 dose; SAE = serious adverse event; t½ = half-life; TTP = time to oroaression; TTR = time to response.

Overall Design

This is a FTIH, open-label, nonrandomized, multicenter study designed to investigate the safety, tolerability, PK, PD, and preliminary clinical activity of escalating doses of GSK6097608 administered IV as monotherapy (Arm A) or in combination with dostarlimab (Arm B) to participants with locally advanced, recurrent, or metastatic solid tumors.

GSK6097608 administered IV every 3 weeks (Q3W) will be evaluated as monotherapy in escalating doses (Arm A) under guidance from a Dose Escalation Committee (DEC). To further evaluate the PK and PD, additional participants will be enrolled in a PK/PD cohort at the RP2D (up to 15 participants) in the following tumor types: non-small-cell lung cancer (NSCLC), head and neck squamous cell carcinoma (HNSCC), or other tumor types defined based on emerging nonclinical and/or clinical data. Additional participants may also be enrolled in PK/PD cohorts at previously cleared dose levels (up to 15 participants per cohort) for dose exploration. These additional participants will contribute to the assessment of safety and preliminary anticancer activity, as well as the overall PK/PD data profile.

Once a dose of GSK6097608 has been identified that is both tolerable and has adequate drug exposure based on PK data, enrollment in the combination arm (Arm B) may begin. In Arm B, escalating doses of GSK6097608 will be evaluated with a fixed dosing regimen of dostarlimab. To further evaluate the PK and PD, additional participants will be enrolled in a PK/PD cohort at the RP2D (up to 15 participants) in the following tumor types: NSCLC, HNSCC, or other tumor types defined based on emerging nonclinical and/or clinical data. In addition to the cohort treated at the RP2D, participants may also be enrolled in PK/PD cohorts at previously cleared dose levels (up to 15 participants per cohort) for dose exploration.

These additional participants will contribute to the assessment of safety and preliminary anticancer activity, as well as the overall PK/PD data profile.

Assessment of disease status at Screening and during study intervention visits will be performed by the investigator in accordance with Response Evaluation Criteria in Solid Tumors, version 1.1 (RECIST 1.1) and a modified RECIST for immune-based therapeutics (iRECIST). A decision to discontinue treatment due to disease progression will be based upon iRECIST; however, some secondary and exploratory anticancer activity analyses will be based on RECIST 1.1. Scans will be collected centrally and stored to allow for the option of central review.

Analysis

After each dosing cohort, the Neuenschwander Continual Reassessment Method (N-CRM) will be used to guide monotherapy and combination-therapy dose escalation. Dose-escalation decisions will be based primarily on dose-limiting toxicities (DLTs); however, the totality of clinical safety assessments, PK, and PD data will be considered. No formal statistical hypotheses will be tested, and analyses will be descriptive.

This is a 2-arm, open-label, intervention study.

Number of Participants

Approximately 100 participants will be enrolled to receive study intervention. The total number of participants to be enrolled is an estimate and will depend on the number needed to adequately characterize the DLT profile and determine the RP2D.

Intervention Groups and Duration

In Arm A (monotherapy), GSK6097608 will be administered IV over approximately 30 minutes to participants under medical supervision of an investigator or appropriately qualified designee.

In Arm B (combination therapy), GSK6097608 will be administered IV first. Dostarlimab will then be administered IV over 30 minutes following the end of the GSK6097608 infusion. Both study interventions will be administered under medical supervision of an investigator or designee.

The study comprises 3 periods: Screening (assessments up to 28 days prior to first dose), Treatment (until disease progression, unacceptable toxicity, death, or withdrawal of consent), and Treatment Discontinuation and Follow-Up (90 days). The total duration of study participation begins with the signing of the informed consent form (ICF) and continues through the final protocol-defined follow-up assessment period. The maximum duration of study participation will depend on the participant's duration of study intervention, with an approximate duration of up to 2 years.

Tumor Imaging and Disease Assessments

Lesion assessment method and timing, evaluation of disease, disease progression, and response criteria will be conducted according to Response Evaluation Criteria in Solid Tumors, version 1.1 (RECIST 1.1). RECIST 1.1 will be used in the assessment of disease burden (target and nontarget lesions determination) at Screening and as the primary measure of tumor response endpoints. iRECIST will be used by investigators to assess tumor response and progression and make treatment decisions.

The invention claimed is:

1. An antibody or antigen binding fragment thereof that specifically binds to CD96, wherein the antibody or antigen binding fragment thereof comprises:
   CDRH1 of SEQ ID NO: 115;
   CDRH2 of SEQ ID NO: 145;
   CDRH3 of SEQ ID NO: 147;
   CDRL1 of SEQ ID NO: 97;
   CDRL2 of SEQ ID NO: 99; and
   CDRL3 of SEQ ID NO: 101.

2. The antibody or antigen binding fragment thereof according to claim 1, wherein the antibody or antigen binding fragment thereof comprises:
   a VH region that is at least 90% identical to SEQ ID NO: 86; and
   a VL region that is at least 90% identical to SEQ ID NO: 85.

3. The antibody or antigen binding fragment thereof according to claim 1, wherein the antibody or antigen binding fragment thereof comprises:
   a VH region that is 100% identical to SEQ ID NO: 86; and
   a VL region that is 100% identical to SEQ ID NO: 85.

4. The antibody or antigen binding fragment thereof according to claim 1, wherein the antibody or antigen binding fragment thereof comprises a humanized sequence or a chimeric sequence.

5. The antibody or antigen binding fragment thereof according to claim 1, which is an antibody.

6. The antibody or antigen binding fragment thereof according to claim 3, which is an antibody.

7. The antibody or antigen binding fragment thereof according to claim 5, wherein the antibody further comprises a human wild-type IgG1 Fc domain.

8. The antibody or antigen binding fragment thereof according to claim 6, wherein the antibody further comprises a human wild-type IgG1 Fc domain.

9. A nucleic acid molecule comprising a nucleic acid sequence encoding the antibody or antigen binding fragment thereof according to claim 1.

10. The nucleic acid molecule according to claim 9, wherein the nucleic acid sequence comprises SEQ ID NO: 87 encoding a VH region and SEQ ID NO: 88 encoding a VL region.

11. An expression vector comprising the nucleic acid molecule according to claim 10.

12. A recombinant host cell comprising the expression vector according to claim 11.

13. A cell line engineered to express the antibody or antigen binding fragment thereof according to claim 1.

14. A pharmaceutical composition comprising the antibody or antigen binding fragment thereof according to claim 1, and a pharmaceutically acceptable carrier.

15. A pharmaceutical composition comprising the antibody or antigen binding fragment thereof according to claim 3, and a pharmaceutically acceptable carrier.

16. A pharmaceutical composition comprising the antibody or antigen binding fragment thereof according to claim 7, and a pharmaceutically acceptable carrier.

17. A pharmaceutical composition comprising the antibody or antigen binding fragment thereof according to claim 8, and a pharmaceutically acceptable carrier.

18. The antibody or antigen binding fragment thereof according to claim 2, which is an antibody.

19. The antibody or antigen binding fragment thereof according to claim 18, wherein the antibody further comprises a human wild-type IgG1 Fc domain.

20. A pharmaceutical composition comprising the antibody or antigen binding fragment thereof according to claim 19, and a pharmaceutically acceptable carrier.

* * * * *